(12) United States Patent
Joo et al.

(10) Patent No.: US 11,878,971 B2
(45) Date of Patent: Jan. 23, 2024

(54) PIPERLONGUMINE-BASED COMPOUND AND IMMUNO REGULATOR COMPRISING THE SAME

(71) Applicant: HUSCION CO., LTD., Seongnam-si (KR)

(72) Inventors: Seong Soo Joo, Yongin-si (KR); Nareum Ha, Yongin-si (KR); Jungmin Yu, Gwangju-si (KR); Youngsoo Gyoung, Gwangju-si (KR); Jonggab Jun, Chuncheon-si (KR); Heonse Jeong, Seoul (KR); Sukil Jang, Gangneung-si (KR)

(73) Assignee: HUSCION CO., LTD., Seongnam-si (KR)

( * ) Notice: Subject to any disclaimer, the term of this patent is extended or adjusted under 35 U.S.C. 154(b) by 0 days.

(21) Appl. No.: 17/525,116

(22) Filed: Nov. 12, 2021

(65) Prior Publication Data
US 2022/0213080 A1 Jul. 7, 2022

(30) Foreign Application Priority Data

Dec. 29, 2020 (KR) .......... 10-2020-0185404
Sep. 29, 2021 (KR) .......... 10-2021-0128774

(51) Int. Cl.

| | | |
|---|---|---|
| C07D 413/12 | (2006.01) | |
| A23L 33/10 | (2016.01) | |
| A23L 33/00 | (2016.01) | |
| A61P 37/06 | (2006.01) | |
| A61K 9/00 | (2006.01) | |
| C07C 235/78 | (2006.01) | |
| C07C 235/88 | (2006.01) | |
| C07D 207/38 | (2006.01) | |
| C07D 211/76 | (2006.01) | |
| C07D 211/86 | (2006.01) | |
| C07D 295/185 | (2006.01) | |
| C07D 405/06 | (2006.01) | |

(52) U.S. Cl.
CPC .......... *C07D 413/12* (2013.01); *A23L 33/10* (2016.08); *A23L 33/40* (2016.08); *A61K 9/0056* (2013.01); *A61P 37/06* (2018.01); *C07C 235/78* (2013.01); *C07C 235/88* (2013.01); *C07D 207/38* (2013.01); *C07D 211/76* (2013.01); *C07D 211/86* (2013.01); *C07D 295/185* (2013.01); *C07D 405/06* (2013.01); *A23V 2002/00* (2013.01)

(58) Field of Classification Search
CPC .............................. C07D 413/12; A61P 37/06
See application file for complete search history.

(56) References Cited

U.S. PATENT DOCUMENTS

| | | |
|---|---|---|
| 5,753,691 A | 5/1998 | Katsuyama et al. |
| 9,108,923 B2 * | 8/2015 | Adams .................. C07C 233/91 |
| 2006/0040966 A1 | 2/2006 | Yuan et al. |
| 2016/0214951 A1 | 7/2016 | Pinkerton et al. |
| 2016/0214998 A1 | 7/2016 | Cocklin |
| 2020/0377510 A1 | 12/2020 | Protter et al. |

FOREIGN PATENT DOCUMENTS

| | | |
|---|---|---|
| CN | 102146054 A | 8/2011 |
| EP | 0412058 A1 | 2/1991 |
| EP | 0720849 A2 | 7/1996 |
| JP | S61245900 A | 11/1986 |
| JP | S61246105 A | 11/1986 |
| JP | H08239322 A | 9/1996 |
| JP | 2008507539 A | 3/2008 |
| WO | 2008026125 A2 | 3/2008 |
| WO | 2015188136 A1 | 12/2015 |
| WO | 2019221755 A1 | 11/2019 |

OTHER PUBLICATIONS

Zhang et al (2017) : STN International CAPLUS database, (Columbus, Ohio), Accession No. 2017: 652688.*
Zheng et al (2019) : STN International CAPLUS database, (Columbus, Ohio), Accession No. 2019: 2194064.*
Wu et al (2014) : STN International CAPLUS database, (Columbus, Ohio), Accession No. 2014: 1049922.*
Puscaru, E. et al., "N-methyl series of piperazine", farmacia, Jun. 20, 2002, pp. 1-1, retrieved on Jul. 26, 2022, XP55946354.
Chemical Library: "piperazine derivative", interchim, May 2, 2012, pp. 1-1, retrieved on Jul. 26, 2022, XP55946373.
Chemical Catalog: "piperazine derivative", ukrorgsyntez ltd, Sep. 29, 2014, pp. 1-1, retrieved on Jul. 26, 2022, XP55946375.
Chemical Catalog: "piperazine derivative", ukrorgsyntez ltd, Sep. 29, 2014, pp. 1-1, retrieved on Jul. 26, 2022, XP55946377.
Chemical Library: "piperazinyl derivative", ChemBridge Corporation, Jun. 20, 2002, pp. 1-1, retrieved on Jul. 26, 2022, XP55946356.
Cui M.-Y., et al., "Bioassay of ferulic acid derivatives as influenza neuraminidase inhibitors", Arch. Pharm. Chern. Life Sci., 2020, Revised Oct. 3, 2019, Accepted Oct. 4, 2019, 13 pages, 353:1900174, XP071648493.
Meegan, M.J., et al., "Piperlongumine (piplartine) and analogues: Antiproliferative microtubule destabilising agents", European Journal of Medicinal Chemistry, Received in revised form Sep. 5, 2016, Accepted Sep. 6, 2016, Available online Sep. 16, 2016, pp. 453-463, vol. 125, XP029842385.

(Continued)

*Primary Examiner* — Golam M Shameem
(74) *Attorney, Agent, or Firm* — Scully, Scott, Murphy & Presser, P.C.

(57) ABSTRACT

Disclosed are a novel piperlongumine-based compound, an immuno regulator containing as an active ingredient the compound, or a pharmaceutically acceptable salt or solvate thereof, and a health functional food for immune regulation.

4 Claims, 14 Drawing Sheets

Specification includes a Sequence Listing.

(56) References Cited

OTHER PUBLICATIONS

Liu, X., et al., "Senolytic activity of piperlongumine analogues: Synthesis and biological evaluation", Bioorganic & Medicinal Chemistry, Received in revised form Jun. 4, 2018, Accepted Jun. 12, 2018, Available online Jun. 18, 2018, pp. 3925-3938, vol. 26, No. 14, XP55946477.

Extended European Search Report dated Aug. 9, 2022 received in European Patent Application No. 21207879.4, 22 pages.

Liu, X., et al., "Senolytic activity of piperlongumine analogues: Synthesis and biological evaluation", Bioorganic & Medicinal Chemistry (2018), Received in revised form Jun. 4, 2018, Accepted Jun. 12, 2018. Available online Jun. 18, 2018, pp. 3925-3938, 26.

Liang, J., et al., "Piperlongumine Acts as an Immunosuppressant by Exerting Prooxidative Effects in Human T Cells Resulting in Diminished TH17 but Enhanced Treg Differentiation", Frontiers in Immunology, Accepted May 12, 2020, Published Jun. 12, 2020, pp. 1-18, vol. 11, Article 1172.

Cui, M.-Y., et al., "Bioassay of ferulic acid derivatives as influenza neuraminidase inhibitors", Arch. Pharm. Chem. Life Sci. 2020, Revised Oct. 3, 2019, Accepted Oct. 4, 2019, pp. 1-13, 353:1900174.

Sivaraj, S., et al., "Piper Longum Linn.—A Fruit Contains Potential Inhibitors of Covid-19 Main Protease Based on Molecular Docking", World Journal of Pharmaceutical Research, Article Revised on May 23, 2020, Accepted on Jun. 12, 2020, pp. 1865-1876, vol. 9, Issue 7.

Peng, S., et al., "Synthesis of Piperlongumine Analogues and Discovery of Nuclear Factor Erthyroid 2-Related Factor 2 (Nrf2) Activators as Potential Neuroprotective Agents", J. Med. Chem 2015, Published Jun. 16, 2015, pp. 5242-5255, 58.

Thai, K., et al., "Design, synthesis, and application of chiral electron-poor guanidines as hydrogen-bonding catalysts for the Michael reaction", Tetrahedron: Asymmetry (2010), Accepted Apr. 20, 2010, Available online May 18, 2010, pp. 751-755, 21.

Nagasaka, T., et al., "Synthesis of 1-trans-Cinnamoyl and 1-[trans-3-(Pyridyl)acryloyl]-2-pyrrolidinone Derivatives and Their Effect on Hemicholinium-Induced Impairment of Water Maze Learning in Mice", Yakugaku Zasshi—Japan, pp. 100-107, 112 (2), with English Language abstract.

Pineschi, M., et al., "Highly Enantioselective Copper-Phosphoramidite-Catalyzed Conjugate Addition of Dialkylzinc Reagents to Acyclic a,β-Unsaturated Imides", Adv. Synth. Catal. 2006, Accepted Nov. 28, 2005, pp. 301-304, 348.

Sibi, M.P., et al., "N-Benzylhydroxylamine Addition to β-Aryl Enoates Enantioselective Synthesis of β-aryl-β-Amino Acid Precursors", Organic Letters, Oct. 1, 2000, pp. S1-S12, vol. 2, No. 21.

Balint, R., et al., "N-Caffeoyl-4-amino-n-butyric Acid, a New Flower-specific Metabolite in Cultured Tobacco Cells and Tobacco Plants", The Journal of Biological Chemistry, Received for publication Mar. 9, 1987, Issue of Aug. 15, pp. 11026-11031, vol. 262, No. 23.

Gessier, F., et al., "Identification and characterization of small molecule modulators of the Epstein-Barr virus-induced gene 2 (EBI2) receptor", Journal of Medicinal Chemistry 2014, Published Mar. 28, 2014, pp. 3358-3368, 57.

Partial European Search Report dated Mar. 29, 2022 issued in EP 21207879.4, 15 pages.

CAS No. 1372394-60-9, Database Registry [Online], Retrieved from STN May 2, 2012.

CAS No. 1627455-38-2, Database Registry [Online], Retrieved from STN Sep. 29, 2014.

CAS No. 432529-28-7, Database Registry [Online], Retrieved from STN Sep. 29, 2014.

CAS No. 1627406-19-2, Database Registry [Online], Retrieved from STN Jun. 20, 2002.

CAS No. 290839-93-9, Database Registry [Online], Retrieved from STN Sep. 26, 2000.

\* cited by examiner

```
                             SEQUENCE LISTING

<160> NUMBER OF SEQ ID NOS: 18

<210> SEQ ID NO 1
   <211> LENGTH: 20
   <212> TYPE: DNA
   <213> ORGANISM: Artificial Sequence
   <220> FEATURE:
   <223> OTHER INFORMATION: beta-actin forward

<400> SEQUENCE: 1
tacagcttca ccaccacagc                                                  20

<210> SEQ ID NO 2
   <211> LENGTH: 20
   <212> TYPE: DNA
   <213> ORGANISM: Artificial Sequence
   <220> FEATURE:
   <223> OTHER INFORMATION: beta-actin reverse

<400> SEQUENCE: 2
aaggaaggct ggaaaagagc                                                  20

<210> SEQ ID NO 3
   <211> LENGTH: 20
   <212> TYPE: DNA
   <213> ORGANISM: Artificial Sequence
   <220> FEATURE:
   <223> OTHER INFORMATION: IL-1beta forward

<400> SEQUENCE: 3
agctgtggca gctacctgtg                                                  20

<210> SEQ ID NO 4
   <211> LENGTH: 20
   <212> TYPE: DNA
   <213> ORGANISM: Artificial Sequence
   <220> FEATURE:
   <223> OTHER INFORMATION: IL-1beta reverse

<400> SEQUENCE: 4
gctctgcttg tgaggtgctg                                                  20

<210> SEQ ID NO 5
   <211> LENGTH: 20
   <212> TYPE: DNA
   <213> ORGANISM: Artificial Sequence
   <220> FEATURE:
   <223> OTHER INFORMATION: IL-2 forward

<400> SEQUENCE: 5
cacttcaagc tccacttcaa                                                  20

<210> SEQ ID NO 6
   <211> LENGTH: 20
   <212> TYPE: DNA
   <213> ORGANISM: Artificial Sequence
   <220> FEATURE:
   <223> OTHER INFORMATION: IL-2 reverse
```

<400> SEQUENCE: 6
agtcaaatcc agaacatgcc                                          20

<210> SEQ ID NO 7
<211> LENGTH: 20
<212> TYPE: DNA
<213> ORGANISM: Artificial Sequence
<220> FEATURE:
<223> OTHER INFORMATION: IL-4 forward

<400> SEQUENCE: 7
cctccaagaa cacaactgag                                          20

<210> SEQ ID NO 8
<211> LENGTH: 20
<212> TYPE: DNA
<213> ORGANISM: Artificial Sequence
<220> FEATURE:
<223> OTHER INFORMATION: IL-4 reverse

<400> SEQUENCE: 8
tccttcacag gacaggaatt                                          20

<210> SEQ ID NO 9
<211> LENGTH: 20
<212> TYPE: DNA
<213> ORGANISM: Artificial Sequence
<220> FEATURE:
<223> OTHER INFORMATION: IL-6 forward

<400> SEQUENCE: 9
ttccatccag ttgccttctt                                          20

<210> SEQ ID NO 10
<211> LENGTH: 20
<212> TYPE: DNA
<213> ORGANISM: Artificial Sequence
<220> FEATURE:
<223> OTHER INFORMATION: IL-6 reverse

<400> SEQUENCE: 10
gttgggagtg gtatcctctg                                          20

<210> SEQ ID NO 11
<211> LENGTH: 20
<212> TYPE: DNA
<213> ORGANISM: Artificial Sequence
<220> FEATURE:
<223> OTHER INFORMATION: IL-10 forward

<400> SEQUENCE: 11
acaataactg cacccacttc                                          20

<210> SEQ ID NO 12
<211> LENGTH: 20
<212> TYPE: DNA
<213> ORGANISM: Artificial Sequence
<220> FEATURE:
<223> OTHER INFORMATION: IL-10 reverse

<400> SEQUENCE: 12
ccactgcctt gctcttattt                                          20

```
<210> SEQ ID NO 13
<211> LENGTH: 20
<212> TYPE: DNA
<213> ORGANISM: Artificial Sequence
<220> FEATURE:
<223> OTHER INFORMATION: IL-17alpha forward

<400> SEQUENCE: 13
ctccagaatg tgaaggtcaa                                          20

<210> SEQ ID NO 14
<211> LENGTH: 20
<212> TYPE: DNA
<213> ORGANISM: Artificial Sequence
<220> FEATURE:
<223> OTHER INFORMATION: IL-17alpha reverse

<400> SEQUENCE: 14
aacagaattc atgtggtggt                                          20

<210> SEQ ID NO 15

<400> SEQUENCE: 15

000

<210> SEQ ID NO 16
<211> LENGTH: 20
<212> TYPE: DNA
<213> ORGANISM: Artificial Sequence
<220> FEATURE:
<223> OTHER INFORMATION: IFNgamma reverse

<400> SEQUENCE: 16
tggacctgtg ggttgttgac                                          20

<210> SEQ ID NO 17
<211> LENGTH: 20
<212> TYPE: DNA
<213> ORGANISM: Artificial Sequence
<220> FEATURE:
<223> OTHER INFORMATION: TNFalpha forward

<400> SEQUENCE: 17
gattatggct cagggtccaa                                          20

<210> SEQ ID NO 18
<211> LENGTH: 20
<212> TYPE: DNA
<213> ORGANISM: Artificial Sequence
<220> FEATURE:
<223> OTHER INFORMATION: TNFalpha reverse

<400> SEQUENCE: 18
gagacagagg caacctgacc                                          20
```

PIPERLONGUMINE-BASED COMPOUND AND IMMUNO REGULATOR COMPRISING THE SAME

CROSS-REFERENCE TO RELATED APPLICATION

This application claims priority under 35 U.S.C. § 119 to Korean Patent Application No. 10-2020-0185404, filed on Dec. 29, 2020, and Korean Patent Application No. 10-2021-0128774, filed on Sep. 29, 2021, in the Korean Intellectual Property Office (KIPO), the disclosure of which is incorporated by reference herein in its entirety.

INCORPORATION BY REFERENCE OF SEQUENCE LISTING

The Sequence Listing in an ASCII text file, named as 40262_SequenceListing.txt of 4 KB, created on Nov. 9, 2021, and submitted to the United States Patent and Trademark Office via EFS-Web, is incorporated herein by reference.

BACKGROUND OF THE INVENTION

1. Field of the Invention

The present disclosure relates to a novel piperlongumine-based compound, an immuno regulator containing the same, and a health functional food for immune regulation.

2. Description of the Prior Art

Immunity refers to a response that maintains bodily homeostasis by distinguishing between self and non-self in the human body to recognize and remove harmful substances that naturally occur or enter from the outside. Immune responses are significant for resisting harmful pathogens, such as viruses, bacteria, and parasites, which invade the human body from the outside, and resisting cancer cells generated inside, or clearing these materials.

However, the defects occurring in some components of the immune system causes no immune response even by harmful substances, and these immunodeficiencies are divided into congenital immunodeficiency and acquired immunodeficiency. Congenital immunodeficiency is a disease caused by the innate absence of immune cells, such as B cells or T cells, and can be treated by only treatments, such as gene therapy, antibody injection, or bone marrow transplantation. Acquired immunodeficiency is caused by abnormalities in the immune responses occurring by immune components in spite of the presence of the immune components per se, and the condition of a disease can be improved by enhancing functions of the immune components.

The abnormal enhancement of immune functions has been treated using immunosuppressants. However, the immunosuppressants have a problem in that they often decrease the body immunity to cause other side effects.

Recently, there are increasing immune diseases caused by such abnormal immune functions, and therefore, the development of immuno regulatory substances capable of enhancing or suppressing immune functions is being actively conducted. These immuno regulatory substances stimulate immune cells to enhance or suppress immune functions in the body, and in this regard, Korean Patent Publication No. 10-2006-0047447 discloses that a monoacetyl diacylglycerol compound represented by a specific chemical formula can be used for the treatment of various diseases, such as disorders caused by malfunctions of various immune systems, cancer, arthritis, atopy, and dementia.

SUMMARY OF THE INVENTION

The present inventors synthesized a novel piperlongumine-based compound having a predetermined chemical structure, and found that such a novel compound has excellent antioxidative activity, cytokine production inhibitory ability, and/or intracytoplasmic signaling inhibitory ability on immune cells, and thus the present inventors completed the present disclosure.

An aspect of the present disclosure is to provide a novel piperlongumine-based compound and a derivative thereof, or a pharmaceutically acceptable salt or solvate thereof.

Another aspect of the present disclosure is to provide an immuno regulator and a health functional food for immune regulation each containing the foregoing novel piperlongumine-based compound as an active ingredient.

Other purposes and advantages of the present disclosure will be clarified by following detailed description and claims.

In accordance with an aspect of the present disclosure, there is provided a compound represented by chemical formula 1 below, or a pharmaceutically acceptable salt or solvate thereof:

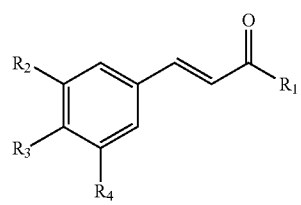

[Chemical Formula 1]

wherein, in chemical formula 1, $R_2$ to $R_4$ are the same or different from each other and are each independently selected from the group consisting of hydrogen, deuterium, halogen, a nitro group, a hydroxyl group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 ring atoms, a $C_1$-$C_{20}$ alkoxy group, a $C_1$-$C_{20}$ ketone group, a $C_1$-$C_{20}$ ester group, a $C_6$-$C_{20}$ aryl group, a heteroaryl group having 5 to 20 ring atoms, and a $C_6$-$C_{20}$ aryloxy group, or may form a $C_6$-$C_{20}$ aryl or heteroaryl ring having 5 to 20 ring atoms, except that $R_2$ to $R_4$ are the same; and $R_1$ is a substituent selected from the following structures:

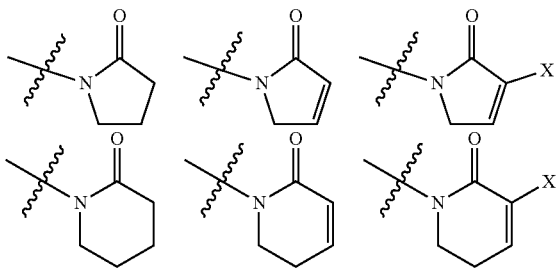

-continued

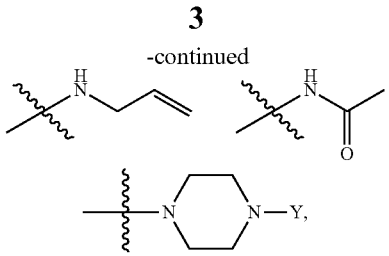

wherein,
X is a halogen atom selected from the group consisting of F, Cl, Br, and I, and
Y is a $C_1$-$C_{10}$ alkyl group,
wherein the alkyl group, ketone group, ester group, aryl group, and heteroaryl group of $R_2$ to $R_4$ may be each independently substituted with at least one substituent selected from the group consisting of deuterium, halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{40}$ aryl group, a heteroaryl group having 5 to 40 ring atoms, a $C_6$-$C_{40}$ aryloxy group, a $C_1$-$C_{40}$ alkyloxy group, a $C_6$-$C_{40}$ aryl amine group, a $C_3$-$C_{40}$ cycloalkyl group, a heterocycloalkyl group having 3 to 40 ring atoms, a $C_1$-$C_{40}$ alkyl silyl group, a $C_1$-$C_{40}$ alkylboron group, a $C_6$-$C_{40}$ arylboron group, a $C_6$-$C_{40}$ aryl phosphine group, a $C_6$-$C_{40}$ aryl phosphine oxide group, and a $C_6$-$C_{40}$ aryl silyl group, and when the number of substituents is plural, the substituents may be the same or different from each other.

In accordance with another aspect of the present disclosure, there is provided an immuno regulator containing, as an active ingredient, the foregoing compound represented by chemical formula 1, or a pharmaceutically acceptable salt or solvate thereof.

In accordance with still another aspect of the present disclosure, there is provided a health functional food for immune regulation containing, as an active ingredient, the foregoing compound represented by chemical formula 1, or a pharmaceutically acceptable salt or solvate thereof.

In accordance with still another aspect of the present disclosure, there is provided a method of immune regulation, including administering to a subject the foregoing compound represented by chemical formula 1, or a pharmaceutically acceptable salt or solvate thereof.

According to embodiments of the present disclosure, the compound represented by chemical formula 1, which is a novel piperlongumine-based derivative that has not been known in the conventional art, exhibits all of excellent antioxidative activity, cytokine production inhibitory ability, and/or intracytoplasmic signaling inhibitory ability on immune cells and thus can be helpfully used as an immuno regulator.

The advantageous effects according to the present disclosure are not limited by the contents exemplified above, and other advantageous effects are included herein.

DETAILED DESCRIPTION OF THE EXEMPLARY EMBODIMENTS

Figure 1:
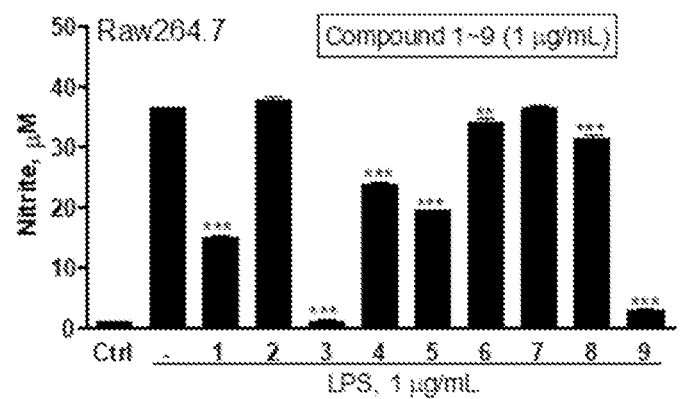
FIG. 1 shows graphs of the results of nitrogen monoxide production inhibitory ability through the use of piperlongumine-based compounds according to the present disclosure.
Figure 1:
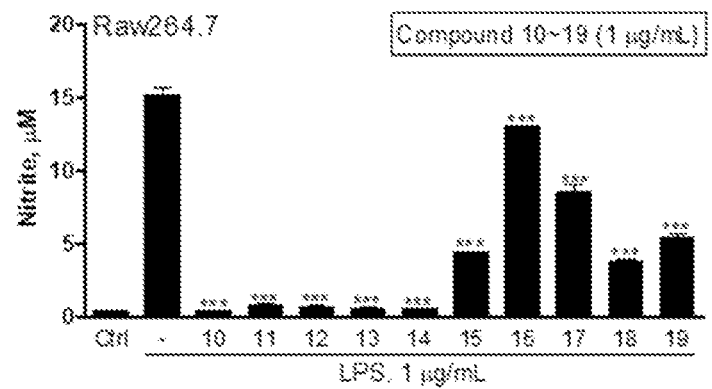

Hereinafter, the present disclosure will be described in detail.

All terms (including technical and scientific terms) used herein will be used with the same meaning as commonly understood by a person skilled in the art to which the present disclosure pertains. Terms that are commonly used and defined in dictionaries will not be interpreted in an idealized or overly formal sense unless expressly so defined herein.

Throughout the specification, when a part "includes", "contains", or "comprises" an element, it may indicate that the part does not exclude another element but can further include another element, unless otherwise stated. Herein, the term "prevention" or the like refers to suppressing or delaying the occurrence of a disease from causes thereof, and the term "treatment" or the like refers to suppressing the progression and/or aggravation of a symptom to stop the progression of a damage or alleviating some or all of symptoms to lead to a direction of healing, even without completely curing.

<Piperlongumine-Based Compound>

An embodiment of the present disclosure is directed to a compound represented by chemical formula 1 below, specifically a novel piperlongumine-derived compound and a derivative thereof, or a pharmaceutically acceptable salt or solvate thereof:

[Chemical Formula 1]

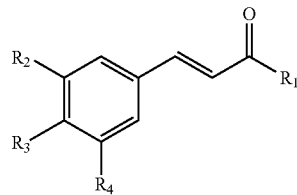

wherein, in chemical formula 1,
$R_2$ to $R_4$ are the same or different from each other and are each independently selected from the group consisting of hydrogen, deuterium, halogen, a nitro group, a hydroxyl group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 ring atoms, a $C_1$-$C_{20}$ alkoxy group, a $C_1$-$C_{20}$ ketone group, a $C_1$-$C_{20}$ ester group, a $C_6$-$C_{20}$ aryl group, a heteroaryl group having 5 to 20 ring atoms, and a $C_6$-$C_{20}$ aryloxy group, or adjacent ones of $R_2$ to $R_4$ are optionally respectively to each other to form a $C_6$-$C_{20}$ aryl or heteroaryl ring having 5 to 20 ring atoms, except that $R_2$ to $R_4$ are the same; and
$R_1$ is a substituent selected from the following structures:

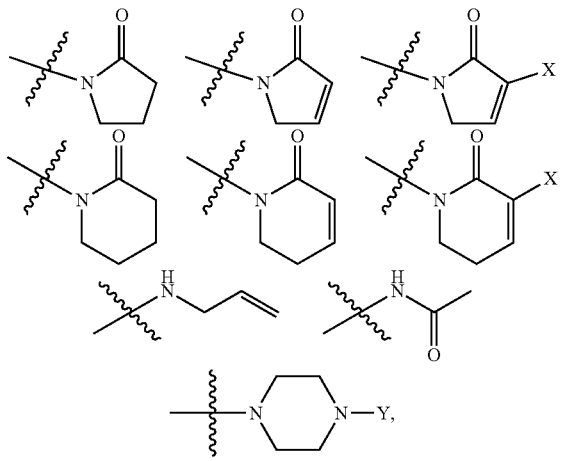

wherein,
the wave lines represent a portion binding with chemical formula 1,
X is a halogen atom selected from the group consisting of F, Cl, Br, and I, and
Y is a $C_1$-$C_{10}$ alkyl group,
wherein the alkyl group, ketone group, ester group, aryl group, and heteroaryl group of $R_2$ to $R_4$ may be each independently substituted with at least one substituent selected from the group consisting of deuterium, halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{40}$ aryl group, a heteroaryl group having 5 to 40 ring atoms, a $C_6$-$C_{40}$ aryloxy group, a $C_1$-$C_{40}$ alkyloxy group, a $C_6$-$C_{40}$ aryl amine group, a $C_3$-$C_{40}$ cycloalkyl group, a heterocycloalkyl group having 3 to 40 ring atoms, a $C_1$-$C_{40}$ alkyl silyl group, a $C_1$-$C_{40}$ alkylboron group, a $C_6$-$C_{40}$ arylboron group, a $C_6$-$C_{40}$ aryl phosphine group, a $C_6$-$C_{40}$ aryl phosphine oxide group, and a $C_6$-$C_{40}$ aryl silyl group, and when the number of substituents is plural, the substituents may be the same or different from each other.

Conventional piperlongumine is a compound in the form of a chalcone in which two rings are linked to an α,β-unsaturated carbonyl chain, wherein one of the two rings is a benzene ring with three methoxy groups (—OMe) connected thereto and the other ring has a 2-piperidone structure. By comparison, the compound of chemical formula 1 according to the present disclosure has a structure of piperlongumine in which a nitro group or another substituent is changed at the 3- and 4-positions of the benzene ring and 2-pyrrolidone and/or various forms of nitrogen compounds are synthesized as the other ring, these rings being inked to an α,β-unsaturated carbonyl chain.

In a specific embodiment of chemical formula 1, $R_1$ may be a moiety selected from the following structures:

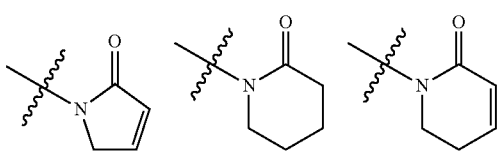

-continued

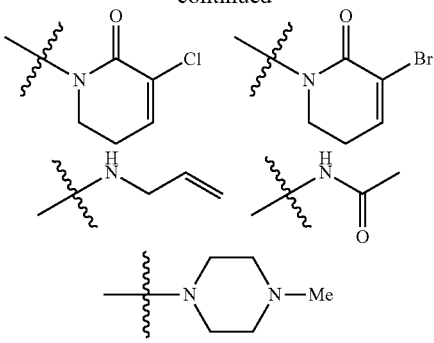

In addition, $R_2$ to $R_4$ are the same or different from each other and are each independently selected from the group consisting of hydrogen, a nitro group, a hydroxyl group, an ester group containing $C_1$-$C_6$ alkyl, and a $C_1$-$C_6$ alkoxy group, or two adjacent substituents may bind to each other to form a $C_6$-$C_{10}$ aryl group or a hetero ring having 5 to 10 ring atoms including at least one of nitrogen and oxygen atoms.

In the present disclosure, the alkyl group, ketone group, ester group, aryl group, and heteroaryl group of $R_2$ to $R_4$ may be each independently substituted with at least one substituent selected from the group consisting of deuterium, halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{40}$ aryl group, a heteroaryl group having 5 to 40 ring atoms, a $C_6$-$C_{40}$ aryloxy group, a $C_1$-$C_{40}$ alkyloxy group, a $C_6$-$C_{40}$ aryl amine group, a $C_3$-$C_{40}$ cycloalkyl group, a heterocycloalkyl group having 3 to 40 ring atoms, a $C_1$-$C_{40}$ alkyl silyl group, a $C_1$-$C_{40}$ alkylboron group, a $C_6$-$C_{40}$ arylboron group, a $C_6$-$C_{40}$ aryl phosphine group, a $C_6$-$C_{40}$ aryl phosphine oxide group, and a $C_6$-$C_{40}$ a aryl silyl group, and when the number of substituents is plural, the substituents may be the same or different from each other.

In a preferable embodiment, the compound of chemical formula 1 may be further embodied to any one of chemical formulas 2 to 5 according to the types of $R_2$ to $R_4$. However, the compound is not limited thereto.

[Chemical Formula 2]

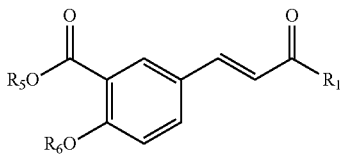

[Chemical Formula 3]

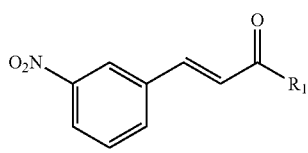

[Chemical Formula 4]

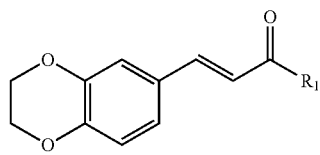

[Chemical Formula 5]

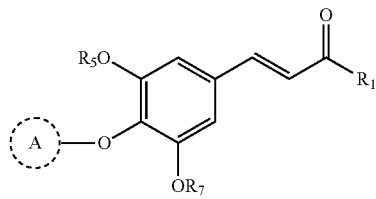

wherein, in chemical formulas 2 to 5, $R_1$ is defined as in chemical formula 1 above.

$R_5$ to $R_7$ are the same or different from each other and are each independently selected from the group consisting of hydrogen, a hydroxyl group, a $C_1$-$C_6$ alkyl group, a $C_1$-$C_6$ alkoxy group, a $C_1$-$C_6$ ketone group, and a $C_1$-$C_6$ ester group.

Ring A may be a monocyclic or polycyclic hydrocarbon ring having 20 or less carbon atoms, and specifically may be selected from the group consisting of a cycloalkyl ring, a heterocycloalkyl ring, an aryl ring, and a heteroaryl ring. At least one carbon constituting such ring A may be substituted with at least one substituent selected from the group consisting of deuterium, halogen, a cyano group, a nitro group, a $C_1$-$C_{40}$ alkyl group, a $C_6$-$C_{40}$ aryl group, and a heteroaryl group having 5 to 40 ring atoms.

The compound represented by chemical formula 1 of the present disclosure described above may be further embodied as the compounds exemplified below. However, the compound represented by chemical formula 1 of the present disclosure is not limited to those exemplified below.

1
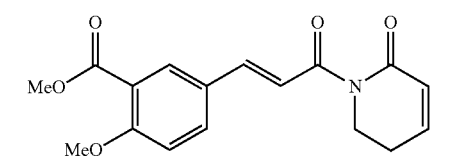

2
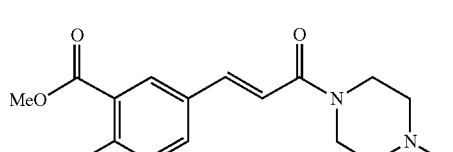

3
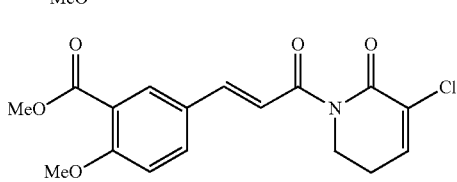

4
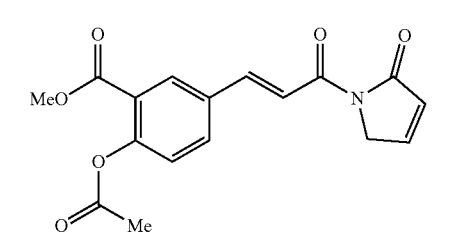

5
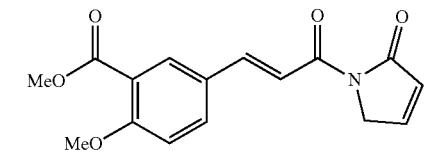

6
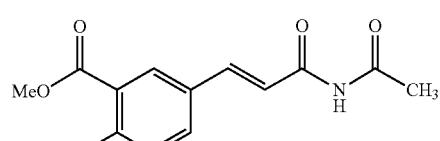

7
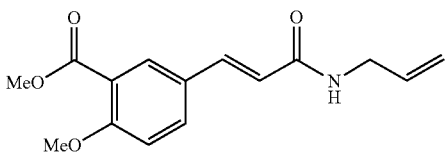

8
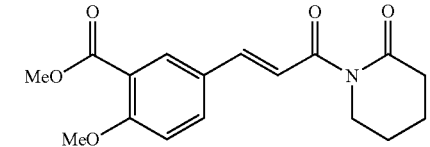

9
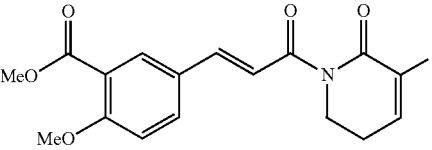

10
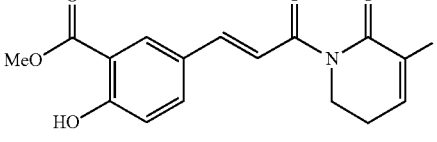

11
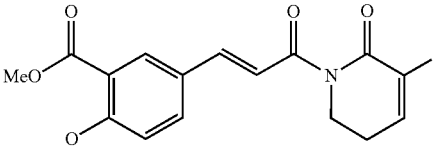

12
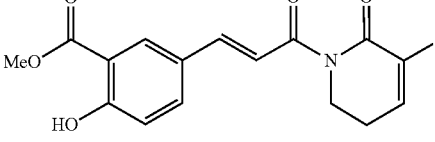

13

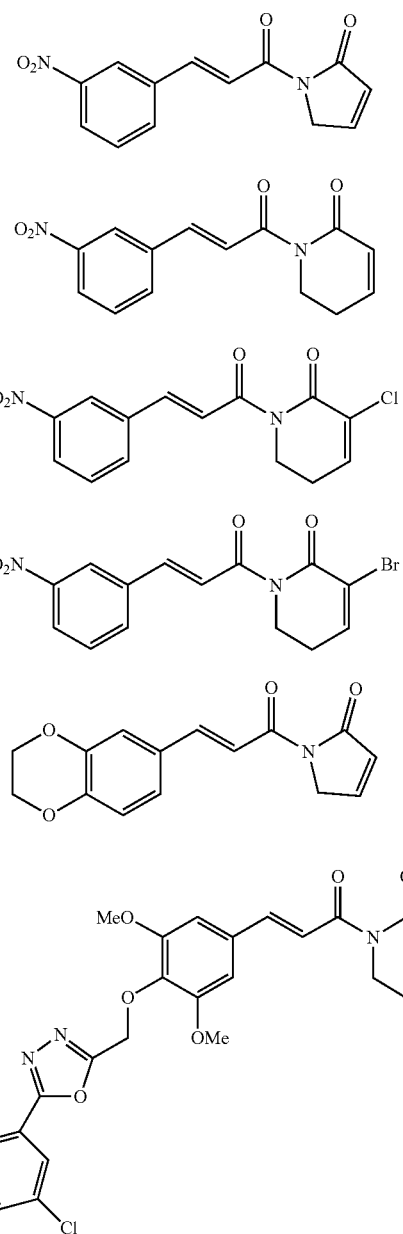

As used herein, the term "alkyl" refers to a monovalent substituent derived from a linear or branched, saturated hydrocarbon having 1 to 40 carbon atoms. Examples thereof may include, but are not limited to, methyl, ethyl, propyl, isobutyl, sec-butyl, pentyl, iso-amyl, hexyl, and the like.

As used herein, the term "alkenyl" refers to a monovalent substituent derived from a linear or branched, unsaturated hydrocarbon having 2 to 40 carbon atoms having one or more carbon-carbon double bonds. Examples thereof may include vinyl, allyl, isopropenyl, 2-butenyl, and the like, but are not limited thereto.

As used herein, the term "alkynyl" refers to a monovalent substituent derived from a linear or branched, unsaturated hydrocarbon having 2 to 40 carbon atoms and one or more carbon-carbon triple bonds. Examples thereof may include ethynyl, 2-propynyl, and the like, but are not limited thereto.

As used herein, the term "aryl" refers to a monovalent substituent derived from an aromatic hydrocarbon having 6 to 40 carbon atoms and having a single ring or two or more rings combined. In addition, the aryl may also include a form in which two or more rings are simply pendant to each other or fused to each other. Specific examples of such aryl may include phenyl, naphthyl, phenanthryl, anthryl, and the like, but are not limited thereto.

As used herein, the term "heteroaryl" refers to a monovalent substituent derived from a monoheterocyclic or polyheterocyclic aromatic hydrocarbon having 5 to 40 ring atoms. In such a case, at least one carbon, preferably one to three carbon atoms in the ring are substituted with a heteroatom, such as N, O, S, or Se. In addition, the heteroaryl may include a form in which two or more rings may be simply pendant to each other or fused to each other, and may furthermore include a form of being fused with an aryl group. Examples of the heteroaryl may include: 6-membered monocyclic rings, such as pyridyl, pyrazinyl, pyrimidinyl, pyridazinyl, and triazinyl; polycyclic ring, such as phenoxathienyl, indolizinyl, indolyl, purinyl, quinolyl, benzothiazole, and carbazolyl; and 2-furanyl, N-imidazolyl, 2-isoxazolyl, 2-pyridinyl, 2-pyrimidinyl, and the like, but are not limited thereto.

As used herein, the term "alkyloxy" refers to a monovalent substituent represented by R'O—, wherein R' is alkyl having 1 to 40 carbon atoms and may include a linear, branched, or cyclic structure. Examples of the alkyloxy may include methoxy, ethoxy, n-propoxy, 1-propoxy, t-butoxy, n-butoxy, pentoxy, and the like, but are not limited thereto.

As used herein, the term "cycloalkyl" refers to a monovalent substituent derived from a monocyclic or polycyclic non-aromatic hydrocarbon having 3 to 40 carbon atoms. Examples of the cycloalkyl may include cyclopropyl, cyclopentyl, cyclohexyl, norbornyl, adamantine, and the like, but are not limited thereto.

As used herein, the term "heterocycloalkyl" refers to a monovalent substituent derived from a non-aromatic hydrocarbon having 3 to 40 ring atoms, wherein one or more carbon atoms, preferably 1 to 3 carbon atoms, in the ring, are substituted with a heteroatom, such as N, O, Se, or S. Examples of the heterocycloalkyl may include morpholine, piperazine, and the like, but are not limited thereto.

As used herein, the term "fused ring" refers to a fused aliphatic ring, a fused aromatic ring, a fused heteroaliphatic ring, a fused heteroaromatic ring, or a combined form thereof.

Furthermore, the present disclosure provides a salt, preferably a pharmaceutically acceptable salt of the compound represented by chemical formula 1.

Herein, the term "pharmaceutically acceptable salt" refers to a salt suitable for use in contact with tissues of humans and lower animals without causing undue toxicity, irritation, allergic responses, or the like within the scope of sound medical judgment. Pharmaceutically acceptable salts have been well known in the art and, for example, are described in detail in literature (S. M. Berge et al., J. Pharmaceutical Sciences, 66, 1, 1977). During the final isolation and purification of the compound of the present disclosure, the salt may be prepared in the same reaction system or may be prepared by a separate reaction with an inorganic or organic base. Preferred examples of the base addition salt form may include: ammonium salts, alkali and earth alkaline metal salts, for example, salts of lithium, sodium, potassium, magnesium, calcium, and the like, salts with organic bases, for example, primary, secondary and tertiary aliphatic and aromatic amines, such as methylamine, ethylamine, propylamine, isopropylamine, four types of butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, benzathine, N-methyl-D-glucamine, 2-amino-2-(hydroxymethyl)-1,3-propanediol, hydrabamine salts, and salts with amino acids, such as, arginine, lysine and the like.

Furthermore, the present disclosure may include a hydrate or solvate of the compound represented by chemical formula 1, or derivative compounds thereof. Of the solvates, the solvent is not particularly limited, and may include all the conventional solvents known in the art.

<Immuno Regulator>

In accordance with another aspect of the present disclosure, there is provided an immuno regulator or immunomodulator containing as an active ingredient a compound represented by chemical formula 1, or a pharmaceutically acceptable salt or solvate thereof. Specifically, the immuno regulator may be an immunosuppressant that inhibits an immune response.

As used herein, the term "active ingredient" refers to an ingredient that can exhibit the desired activity alone or the activity together with a carrier that is not active per se, and a specific content value thereof is not particularly limited.

The immuno regulator according to the present disclosure may contain 0.01 to 99 wt %, specifically, 0.1 to 95 wt % of a compound of chemical formula 1, as an active ingredient, relative to the total weight of the composition. The immuno regulator of the present disclosure may further contain, in addition to the foregoing active ingredient, at least one type of active ingredient exhibiting the same or similar function.

The immuno regulator of the present disclosure may contain a carrier, a diluent, an excipient, or a mixture thereof that is commonly used for pharmaceutically suitable and physiologically acceptable formulations. Any pharmaceutically acceptable carrier may be used as long as the carrier is suitable for in vivo delivery of the composition. Specifically, the carrier may be a compound described in Merck Index, 13th ed., Merck & Co. Inc., saline, sterile water, Ringer's solution, a dextrose solution, a maltodextrin solution, glycerol, ethanol, or a mixture thereof. If necessary, common additives, such as an antioxidant, a buffer, and a bacteriostatic agent, may be added.

The composition may be prepared into formulations by addition of a diluent or an excipient, such as a filler, an extender, a binder, a wetting agent, a disintegrant, or a surfactant that is commonly used.

The immuno regulator of the present disclosure may be prepared as an oral formulation or a parenteral formulation. The oral formulation may include a solid formulation and a liquid formulation. The solid formulation may be a tablet, a pill, a powder, granules, a capsule, or troche, and these solid formulations may be prepared by addition of at least one excipient to the composition. The excipient may be starch, calcium carbonate, sucrose, lactose, gelatin, or a mixture thereof. The solid formulation may contain a lubricant, and examples thereof may be magnesium stearate, talc, and the like. The liquid formulation may be a suspension, a liquid for internal use, an emulsion, or a syrup. The liquid formulation may contain an excipient, such as a wetting agent, a sweetener, an aromatic agent, or a preservative.

The parenteral formulation may include an injection, a suppository, a respiratory inhalation powder, a spray aerosol, a powder, a cream, and the like. The injection can include a sterile aqueous solution, a non-aqueous solvent, a suspending solvent, an emulsion, and the like. Examples of the non-aqueous solvent and suspending solvent may include propylene glycol, polyethylene glycol, a vegetable oil such as olive oil, an injectable ester such as ethyl oleate, and the like.

The immuno regulator of the present disclosure may be administered orally or parenterally according to the desired method. The parenteral administration may include an intraperitoneal, rectal, subcutaneous, intravenous, intramuscular, or intrathoracic injection.

The immuno regulator may be administered at a pharmaceutically effective amount. The pharmaceutically effective amount may depend on the type or severity of disease, the activity of a drug, the sensitivity of a patient to a drug, the time of administration, the route of administration, the duration of treatment, a drug to be used in combination, and the like. However, for preferable effects, the amount of the active ingredient contained in the pharmaceutical composition according to the present disclosure may be 0.0001 to 1,000 mg/kg, specifically 0.001 to 500 mg/kg. The administration frequency may be once or several times a day.

The immuno regulator of the present disclosure may be administered alone or in combination with other therapeutic agents. In the combination administration, the administration may be sequential or simultaneous.

<Health Functional Food for Immune Regulation>

In accordance with another aspect of the present disclosure, there is provided a health functional food for immune regulation containing as an active ingredient a compound represented by chemical formula 1, or a pharmaceutically acceptable salt or solvate thereof.

As used herein, the term "health functional food" refers to a food that is prepared and processed, for the purpose of health support, by using as a raw material a specific ingredient having functionality useful for the human body or by a method of extraction, concentration, purification, mixing, or the like of a specific ingredient contained in a food raw material. The health functional food may have functions associated with the prevention of diseases, the recovery from diseases, and the like.

In the health functional food according to the present disclosure, the compound may be added as it is or may be used together with other foods or food compositions. The amount of the active ingredient used may be appropriately determined according to the purpose of use of the active ingredient, and is not particularly limited. Typically, the compound of chemical formula 1 according to the present disclosure, or an isomer, pharmaceutically acceptable salt, or solvate thereof, may be added in an amount of 0.001 to 99 wt %, specifically, 0.1 to 95 wt %, relative to the total weight of raw materials of a food or beverage when manufactured into the corresponding food or beverage.

The health functional food of the present disclosure may contain ingredients commonly used in food compositions in the art, in addition to the foregoing compound of chemical formula 1, or an isomer, pharmaceutically acceptable salt, or solvate thereof. For example, the health functional food may further contain at least one additive selected from the group consisting of an organic acid, a phosphate salt, an antioxidant, lactose casein, dextrin, glucose, sugar, and sorbitol. In addition, the health functional food may further contain several nutrients, vitamins, minerals (electrolytes), flavoring agents such as synthetic flavoring agents and natural flavoring agents, coloring agents, extenders, pectic acid and salts thereof, alginic acid and salts thereof, organic acids, protective colloid thickeners, PH adjusters, stabilizers, preservatives, glycerin, alcohol, carbonating agents used for carbonated drinks, and the like.

The health functional food of the present disclosure may be prepared in any formulation that is conventionally prepared in the art, and for example, the feature of providing the health functional food in the form of a tablet, granules, a pill, a capsule, a liquid preparation, a syrup, or a beverage is also within the scope of the present disclosure.

As for the health functional food according to the present disclosure, the type of food to which the compound of chemical formula 1, or an isomer, pharmaceutically acceptable salt, or solvate thereof can be added is not particularly limited. Examples thereof include various types of foods, powders, granules, tablets, capsules, syrups, beverages, gums, teas, vitamin complexes, health functional foods, and the like. Specific examples thereof may include meat, sausage, bread, chocolate, candies, snacks, cookies, pizza, ramen, other noodles, gums, dairy products including ice cream, various types of soups, beverages, teas, drinks, alcoholic beverages, vitamin complexes, other nutrients, and the like, but are not limited to these types of foods.

Furthermore, the present disclosure provides a method of immune regulation, comprising administering to a subject the foregoing compound represented by chemical formula 1, or a pharmaceutically acceptable salt or solvate thereof.

The subject may be a mammalian animal, specifically a human.

The administration may be oral or parenteral administration according to the desired method. The parenteral administration may include an intraperitoneal, rectal, subcutaneous, intravenous, intramuscular, or intrathoracic injection. The administration may be conducted at a pharmaceutically effective amount. The pharmaceutically effective amount may depend on the type or severity of disease, the activity of a drug, the sensitivity of a patient to a drug, the time of administration, the route of administration, the duration of treatment, a drug to be used in combination, and the like.

However, for preferable effects, the amount of the active ingredient contained in the pharmaceutical composition according to the present disclosure may be 0.0001 to 1,000 mg/kg, specifically 0.001 to 500 mg/kg. The administration frequency may be once or several times a day.

The administration may be conducted alone or in combination with other therapeutic agents. In the combination administration, the administration may be sequential or simultaneous.

Hereinafter, the present disclosure will be described in more detail with reference to exemplary embodiments. These exemplary embodiments are provided only for the purpose of illustrating the present disclosure in more detail, and therefore, according to the purpose of the present disclosure, it would be apparent to a person skilled in the art that these examples are not construed to limit the scope of the present disclosure.

Preparative Example 1: Synthesis of Compound 1

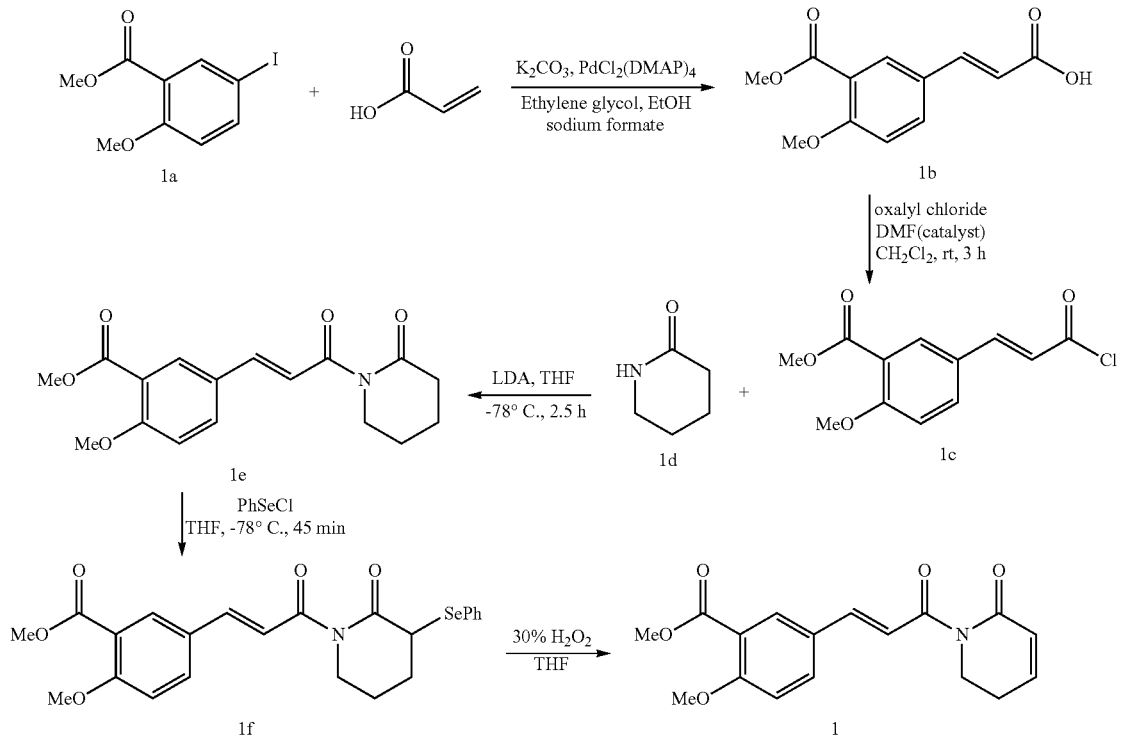

1-1: Preparation of (E)-methyl-2-methoxy-5-(3-oxo-3-(2-oxo-3-(phenylselanyl)piperidin-1-yl)prop-1-en-1-yl)benzoate (Compound 1f)

(E)-methyl-2-methoxy-5-(3-oxo-3-(2-oxopiperidin-1-yl) prop-1-en-1-yl (Compound 1e) (0.22 g, 0.68 mmol) was added into a 25-mL round-bottom flask under argon atmosphere, and charged with tetrahydrofuran (3.70 mL). Then, the temperature was lowered to −78° C., and LDA (0.45 mL, 0.88 mmol, 2.0 M solution) was added dropwise, followed by stirring for 45 minutes. Phenylselenyl chloride (0.14 g, 0.75 mmol) dissolved in tetrahydrofuran (3.75 mL) was slowly added at −78° C., followed by stirring for 4.5 hours. Upon the completion of the reaction, the remaining LDA was decomposed by addition of water, followed by further stirring at 0° C. for 15 minutes and extraction twice with dichloromethane. The organic layer was washed once with a saturated sodium chloride solution, dried over anhydrous sodium sulfate, evaporated under reduced pressure, and then separated by silica gel chromatography (ethyl acetate/hexane=1/4 to 1/3), to give (E)-methyl-2-methoxy-5-(3-oxo-3-(2-oxo-3-(phenylselanyl)piperidin-1-yl)prop-1-en-1-yl)benzoate (Compound 1f) (100 mg, 31.2%) as a white solid.

1H NMR (400 MHz, Chloroform-d) δ 7.95 (d, J=2.3 Hz, 1H), 7.72-7.68 (m, 2H), 7.67-7.60 (m, 2H), 7.38-7.31 (m, 3H), 7.05 (d, J=15.6 Hz, 1H), 6.98 (d, J=8.8 Hz, 1H), 4.11 (t, J=5.3 Hz, 1H), 3.95 (s, 3H), 3.92 (s, 3H), 3.71 (ddd, J=13.7, 9.2, 4.6 Hz, 1H), 2.32 (tq, J=10.5, 5.4 Hz, 1H), 2.19-2.05 (m, 2H), 1.26 (d, J=2.7 Hz, 2H).

1-2: (E)-methyl-2-methoxy-5-(3-oxo-3-(2-oxo-5,6-dihydropyridin-1(2H)-yl)prop-1-en-1-yl)benzoate (Compound 1)

(E)-methyl-2-methoxy-5-(3-oxo-3-(2-oxo-3-phenylselanyl)piperidin-1-yl)prop-1-en-1-yl)benzoate (Compound 1f) (0.10 g, 0.21 mmol) prepared in 1-1 above was added into a 25-mL round-bottom flask under argon atmosphere, and charged with tetrahydrofuran (2.00 mL). Then, the temperature was lowered to −0° C., and hydrogen peroxide (0.05 mL, 0.59 mmol, 30% solution) was added dropwise, followed by stirring for 15 minutes. Thereafter, the temperature was raised to room temperature, followed by further stirring for 30 minutes. Upon the completion of the reaction, a saturated sodium bicarbonate solution was added, followed by extraction twice with dichloromethane. The organic layer was washed once with a saturated sodium chloride solution, dried over anhydrous sodium sulfate, evaporated under reduced pressure, and then separated by silica gel chromatography (ethyl acetate/hexane=1/1.5), to give (E)-methyl-2-methoxy-5-(3-oxo-3-(2-oxo-5,6-dihydropyridin-1(2H)-yl)prop-1-en-1-yl)benzoate (Compound 1) (40 mg, 60.6%) as a white solid.

1H NMR (400 MHz, Chloroform-d) δ 8.01 (d, J=2.4 Hz, 1H), 7.74-7.66 (m, 2H), 7.43 (d, J=15.7 Hz, 1H), 7.00-6.92 (m, 2H), 6.05 (dt, J=9.6, 1.8 Hz, 1H), 4.04 (t, J=6.5 Hz, 2H), 3.94 (s, 3H), 3.90 (s, 3H), 2.48 (tdd, J=6.3, 4.2, 1.9 Hz, 2H).

13C NMR (101 MHz, Chloroform-d) δ 168.92, 166.08, 165.86, 160.38, 145.51, 142.33, 133.42, 131.75, 127.39, 125.87, 120.69, 120.48, 112.24, 56.22, 52.20, 41.65, 24.81.

Preparative Example 2: Synthesis of (E)-methyl-2-methoxy-5-(3-(4-methylpiperazin-1-yl)-3-oxoprop-1-en-1-yl)benzoate (Compound 2)

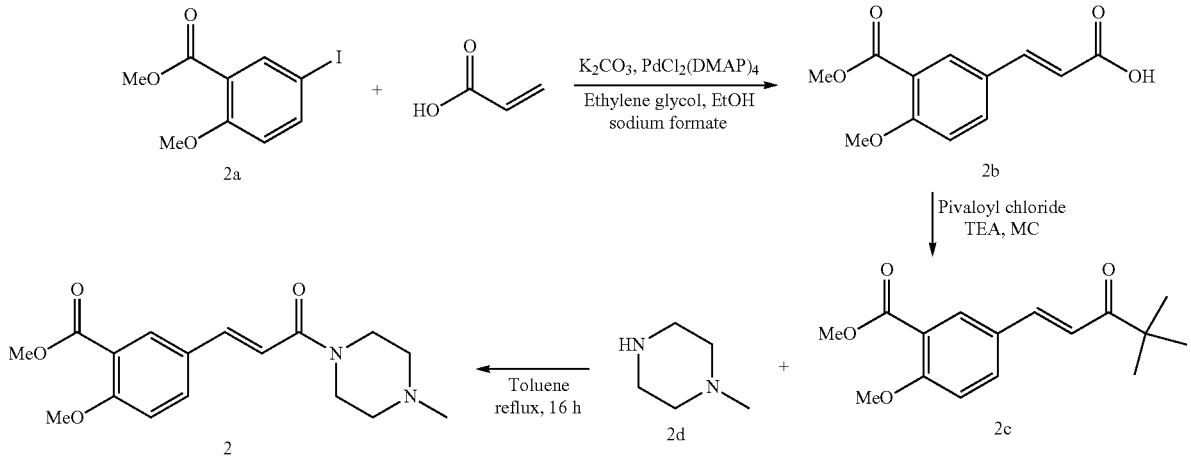

(E)-3-(4-methoxy-3-(methoxycarbonyl)phenyl)acrylic acid (Compound 2b) (0.20 g, 0.85 mmol) was added into a 25-mL round-bottom flask under argon atmosphere, and charged with dichloromethane (12.0 mL). Then, the temperature was lowered to 0° C., and triethyl amine (0.18 mL, 1.28 mmol) and pivaloyl chloride (0.12 mL, 0.94 mmol) were slowly added, followed by stirring at the same temperature for 45 minutes. Thereafter, methyl piperazine (2d) (0.15 mL, 1.28 mmol) was slowly added to the reaction mixture, followed by stirring at room temperature for 2 hours. Upon the completion of the reaction, a saturated sodium bicarbonate solution was added to the mixture to terminate the reaction, and the mixture was diluted by the addition of water. The aqueous solution layer was extracted three times with dichloromethane. The organic layer was washed twice with a saturated sodium chloride solution, dried over anhydrous sodium sulfate, evaporated under reduced pressure to remove the solvent of the mixture, and then separated by silica gel chromatography (methanol/dichloromethane=1/25), to give (E)-methyl-2-methoxy-5-(3-(4-methylpiperazin-1-yl)-3-oxoprop-1-en-1-yl)benzoate (Compound 2) (250 mg, 61.4%) as a pale yellow oil.

1H NMR (400 MHz, Chloroform-d) δ 8.00 (d, J=2.3 Hz, 1H), 7.66-7.56 (m, 2H), 6.98 (d, J=8.7 Hz, 1H), 6.80 (d, J=15.4 Hz, 1H), 3.94 (s, 3H), 3.92 (s, 3H), 3.73-3.62 (m, 4H), 2.45 (t, J=5.1 Hz, 4H), 2.33 (s, 3H).

Preparative Example 3: Synthesis of Compound 3

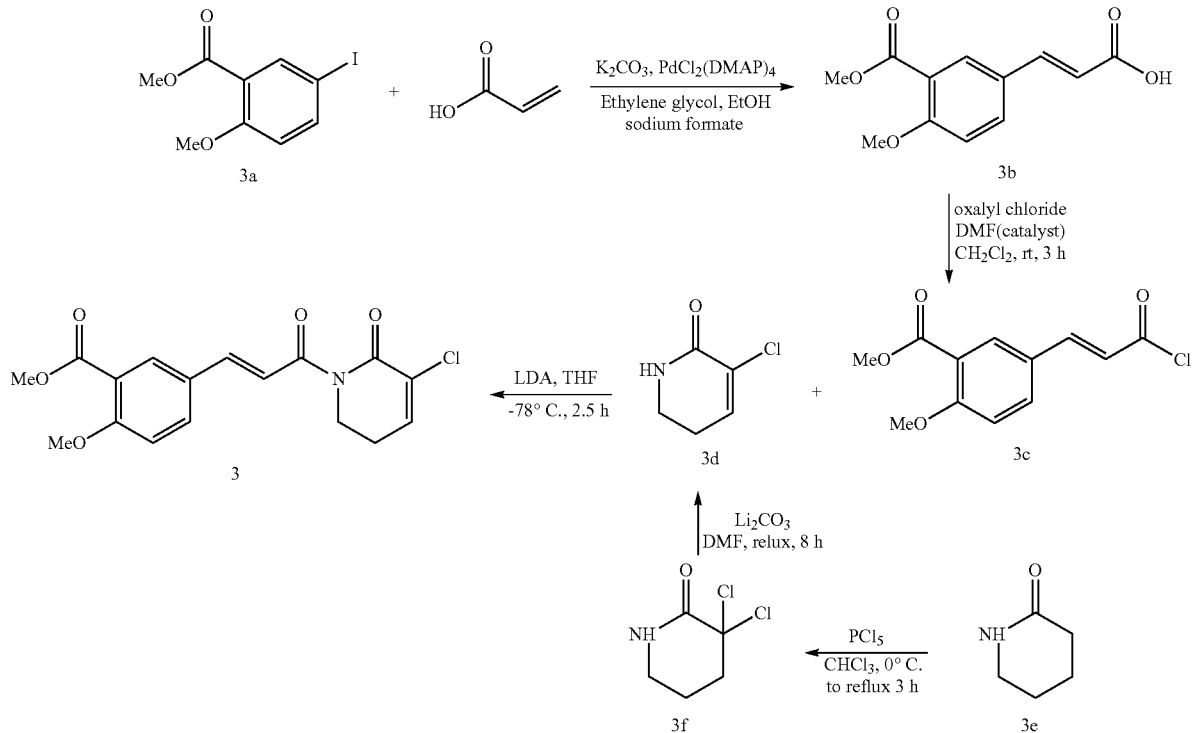

3-1: Preparation of 3,3-dichloropiperidin-2-one (Compound 3f)

Piperidin-2-one (Compound 3e) (2.00 g, 20.18 mmol) was added into a 100-mL round-bottom flask under argon atmosphere, and charged with chloroform (20.00 mL). Then, the temperature was lowered to 0° C., and phosphorus pentachloride (12.80 g, 61.33 mmol) was slowed added for 10 minutes, followed by stirring under reflux at 60° C. Upon the completion of the reaction, the temperature was lowered to room temperature, and then the mixture was added to ice water. The aqueous solution layer was extracted three times with dichloromethane. The organic layer was washed once with a saturated sodium chloride solution, dried over anhydrous magnesium sulfate, and then evaporated under reduced pressure, to give, without an additional purification process, 3.3-dichloropiperidin-2-one (Compound 3f) (4.00 g).

1H NMR (400 MHz, Chloroform-d) δ 6.18 (s, 1H), 3.44 (td, J=6.2, 2.4 Hz, 2H), 2.82-2.74 (m, 2H), 2.15-2.05 (m, 2H).

3-2: Preparation of 3-chloro-5,6-dihydropyridin-2(1H)-one (Compound 3d)

3,3-Dichloropiperidin-2-one (Compound 3f) (4.00 g, 24.04 mmol) prepared in 3-1 above was added into a 50-mL round-bottom flask under argon atmosphere, and charged with dimethyl formamide (12.00 mL). Then, lithium carbonate (3.70 g, 49.30 mmol) was added, followed by stirring with heating at 120° C. for 7 hours. Upon the completion of the reaction, the temperature was lowered to room temperature, and then the mixture was added to ice water. The aqueous solution layer was extracted three times with dichloromethane. The organic layer was washed once with a saturated sodium chloride solution, dried over anhydrous magnesium sulfate, and then separated by silica gel chromatography (ethyl acetate/hexane=1/1.5 to 1/1), to give 3-chloro-5,6-dihydropyridin-2(1H)-one (Compound 3d) (0.55 g, 17.6%) as a brown solid.

1H NMR (400 MHz, Chloroform-d) δ 6.78 (t, J=4.6 Hz, 1H), 6.70 (s, 1H), 3.53-3.43 (m, 2H), 2.48 (td, J=7.1, 4.5 Hz, 2H).

3-3: Preparation of (E)-methyl-5-(3-(3-chloro-2-oxo-5,6-dihydropyridin-1(2H)-yl)-3-oxoprop-1-en-1-yl)-2-methoxybenzoate (Compound 3)

3-Chloro-5,6-dihydropyridin-2 (1H)-one (Compound 3d) (0.10 g, 0.77 mmol) prepared in 3-2 above was added into a 25-mL round-bottom flask under argon atmosphere, and charged with tetrahydrofuran (1.50 mL). Then, the temperature was lowered to −78° C., and LDA (0.40 mL, 0.77 mmol, 2.0 M solution) was added dropwise, followed by stirring for 45 minutes. (E)-methyl-5-(3-chloro-3-oxopro-1-pen-1-yl)-2-methoxybenzoate (Compound 3c) (0.16 g, 0.64 mmol) dissolved in tetrahydrofuran (1.50 mL) was slowly added at −78° C., followed by stirring for 1 hour. Upon the completion of the reaction, the remaining LDA was decomposed by 1 N hydrochloric acid, followed by extraction twice with ethyl acetate. The ethyl acetate layer was washed once with a saturated sodium chloride solution, dried over anhydrous sodium sulfate, evaporated under reduced pressure, and then separated by column chromatography (ethyl acetate/hexane=1/2 to 1/1), to give (E)-methyl-5-(3-(3-chloro-2-oxo-5,6-dihydroxypyridin-1(2H)-yl)-3-oxoprop-1-en-1-yl)-2-methoxybenzoate (Compound 3) (98 mg, 43.8%) as a white solid.

1H NMR (400 MHz, Chloroform-d) δ 8.02 (d, J=2.3 Hz, 1H), 7.74 (d, J=15.3 Hz, 1H), 7.71-7.69 (m, 1H), 7.43 (d, J=15.6 Hz, 1H), 7.09 (t, J=4.6 Hz, 1H), 6.98 (d, J=8.7 Hz, 1H), 4.09 (t, J=6.5 Hz, 2H), 3.95 (s, 3H), 3.91 (s, 3H), 2.57 (td, J=6.5, 4.6 Hz, 2H).

13C NMR (101 MHz, Chloroform-d) δ 168.52, 166.01, 161.46, 160.58, 143.43, 141.09, 133.53, 131.84, 128.29, 127.13, 120.59, 119.91, 112.27, 56.24, 52.23, 41.76, 25.32.

Preparative Example 4: Synthesis of Compound 5

13C NMR (101 MHz, DMSO-d6) δ 167.60, 165.81, 159.23, 142.53, 133.05, 130.48, 126.40, 120.66, 117.98, 112.96, 60.19, 56.08, 52.02.

4-2: Preparation of 1H-pyrrol-2(5H)-one (Compound 5d)

Pyrrole (5.0 mL, 72.0 mmol) and barium carbonate (1.50 g, 7.60 mmol) were added into a round-bottom flask under

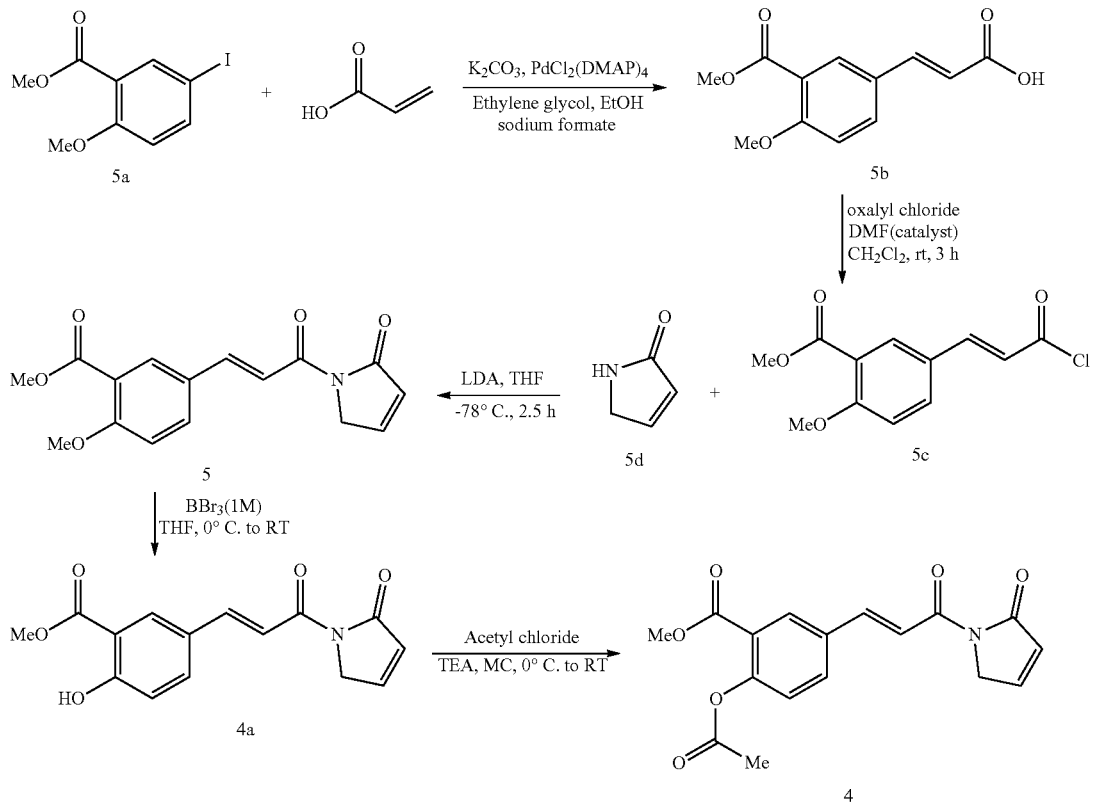

4-1: Preparation of (E)-3-(4-methoxy-3-(methoxycarbonyl)phenyl)acrylic Acid (Compound 5b)

A mixture obtained by stirring a potassium carbonate aqueous solution (1.06 g/2.50 mL distilled water, 7.64 mmol), ethylene glycol (2.50 mL), acrylic acid (0.48 mL, 6.76 mmol), ethanol (0.25 mL), sodium formate (14.0 mg, 0.20 mmol), and PdCl$_2$(DMAP)$_4$ (13.0 mg, 0.02 mmol) was added to methyl-5-iodo-2-methoxybenzoate (Compound 5a) (1.50 g, 5.14 mmol). The mixture was carefully stirred for 5 minutes, and then refluxed until a black palladium precipitate was generated. After the reaction mixture was cooled to room temperature, the pH was adjusted to 1 by using a 1 N hydrochloric acid solution. The produced solid was filtered, washed three times with water, and then dried, to give (E)-3-(4-methoxy-3-(methoxycarbonyl)phenyl)acrylic acid (Compound 5b) (1.02 g, 83.4%) as a white solid.

1H NMR (400 MHz, DMSO-d6) δ 12.30 (s, 1H), 7.94-7.87 (m, 2H), 7.56 (d, J=16.0 Hz, 1H), 7.20 (d, J=8.7 Hz, 1H), 6.45 (d, J=15.9 Hz, 1H), 3.86 (s, 3H), 3.80 (s, 3H), 2.09 (s, 1H).

argon atmosphere, and then charged with distilled water (0.30 mL). Thereafter, 30% hydrogen peroxide (9.0 mL) was added dropwise. The flask was equipped with a condenser, and then refluxing was conducted for 5 hours. Then, the temperature was lowered to room temperature, and the remaining hydrogen peroxide was removed using a 10% sodium nitrite solution. After stirring was conducted until bubbles stopped, the solvent filtered by a filter bed was evaporated under reduced pressure. The dark red solid was dissolved in 1,4-dioxane (50.0 mL), again filtered by a filter paper, washed with 1,4-dioxane (50.0 mL), dried over anhydrous sodium sulfate, and then evaporated under reduced pressure, to give 1H-pyrrol-2 (5H)-one (Compound 5d) (1.42 g, 23.9%) as a dark red liquid.

1H NMR (400 MHz, CDCl3): δ 9.27 (1H, br s), 7.16-7.19 (1H, dt, J=6.0, 1.8 Hz), 6.17-6.19 (1H, d, J=6.0 Hz). 4.50 (2H, d, J=1.8 Hz).

13C NMR (101 MHz, CDCl3): δ 175.5, 146.2, 127.8, 49.2.

4-3: Preparation of (E)-methyl-2-methoxy-5-(3-oxo-3-(2-oxo-2,5-dihydro-1H-pyrrol-1-yl)prop-1-en-1-yl)benzoate (Compound 5)

1H-pyrrol-2(5H)-one (Compound 5d) (0.21 g, 2.55 mmol) prepared in Preparative Example 4-2 above was added into a 50-mL round-bottom flask under argon atmosphere, and charged with tetrahydrofuran (3.30 mL). Then, the temperature was lowered to −78° C., and LDA (1.30 mL, 2.55 mmol, 2.0 M solution) was added dropwise, followed by stirring for 45 minutes. (E)-methyl-5-(3-chloro-3-oxo-pro-1-pen-1-yl)-2-methoxybenzoate (Compound 5c) (0.54 g, 2.12 mmol) dissolved in tetrahydrofuran (2.70 mL) was slowly added at −78° C., followed by stirring for 1 hour. Upon the completion of the reaction, the remaining LDA was decomposed by 1 N hydrochloric acid, followed by extraction with ethyl acetate. The ethyl acetate layer was washed with a saturated sodium chloride solution, dried over anhydrous sodium sulfate, evaporated under reduced pressure, and then separated by column chromatography (ethyl acetate/hexane=1/2 to 1/1), to give (E)-methyl-2-methoxy-5-(3-oxo-3-(2-oxo-2,5-dihydro-1H-pyrrol-1-yl)prop-1-en-1-yl)benzoate (Compound 5) (75 mg, 30.0%) as a yellow solid.

1H NMR (400 MHz, CDCl3) δ 8.06 (d, J=2.3 Hz, 1H), 7.96 (d, J=15.7 Hz, 1H), 7.86 (d, J=15.7 Hz, 1H), 7.78 (dd, J=8.7, 2.3 Hz, 1H), 7.35 (dt, J=6.0, 2.1 Hz, 1H), 7.01 (d, J=8.8 Hz, 1H), 6.22 (dt, J=6.0, 1.9 Hz, 1H), 4.54 (t, J=2.0 Hz, 2H), 3.96 (s, 3H), 3.92 (s, 3H).

13C NMR (101 MHz, Chloroform-d) δ 170.21, 166.02, 165.20, 160.68, 146.84, 144.71, 133.49, 132.25, 127.87, 127.16, 120.56, 117.39, 112.32, 56.25, 52.25, 51.11.

Preparative Example 5: Synthesis of Compound 4

5-1: Preparation of (E)-methyl-2-hydroxy-5-(3-oxo-3-(2-oxo-2,5-dihydro-1H-pyrrol-1-yl)prop-1-en-1-yl)benzoate (Compound 4a)

(E)-methyl-2-methoxy-5-(3-oxo-3-(2-oxo-2,5-dihydro-1-pyrrol-1-en-1-yl)prop-1-en-1-yl)benzoate (Compound 5) (70 mg, 0.23 mmol) prepared in Preparative Example 4 and tetrahydrofuran (4.0 mL) were added into a round-bottom flask under argon atmosphere, and the temperature was lowered to 0° C. After 10 minutes, a tribromoborane solution (1.0 M dichloromethane solution, 0.70 mL, 0.69 mmol) was slowly added, followed by stirring for 4 hours, and then the reaction temperature was gently adjusted to room temperature. The presence or absence of the reaction was checked by TLC. Upon the completion of the reaction, the reaction temperature was again adjusted to 0° C., and the reaction was terminated using 0.50 mL of a 1 N hydrochloric acid solution. The stirring was further conducted at the same temperature for 10 minutes, followed by extraction three times with dichloromethane. The organic layer was washed once with a saturated sodium chloride solution, dried over anhydrous sodium sulfate, evaporated under reduced pressure, and then separated by silica gel chromatography (ethyl acetate/hexane=1/2 to 1/1), to give (E)-methyl-2-hydroxy-5-(3-oxo-3-(2-oxo-2,5-dihydro-1H-pyrrol-1-yl) prop-1-en-1-yl)benzoate (Compound 4a) (10 mg, 15.2%) as a brown solid.

1H NMR (400 MHz, Chloroform-d) δ 11.05 (s, 1H), 8.11 (d, J=2.3 Hz, 1H), 7.95 (d, J=15.8 Hz, 1H), 7.85 (d, J=15.8 Hz, 1H), 7.80 (dd, J=8.7, 2.3 Hz, 1H), 7.35 (dt, J=6.0, 2.1 Hz, 1H), 7.03 (d, J=8.7 Hz, 1H), 6.22 (dt, J=6.0, 1.9 Hz, 1H), 4.54 (t, J=1.9 Hz, 2H), 3.99 (s, 3H).

5-2: Preparation of (E)-methyl-2-acetoxy-5-(3-oxo-3-(2-oxo-2,5-dihydro-1H-pyrrol-1-yl)prop-1-en-1-yl)benzoate (Compound 4)

(E)-methyl-2-hydroxy-5-(3-oxo-3-(2-oxo-2,5-dihydro-1H-pyrrol-1-yl)prop-1-en-1-yl)benzoate (Compound 4a) (10 mg, 0.04 mmol) prepared in Preparative Example 5-1 above and dichloromethane (1.0 mL) were added into a round-bottom flask under argon atmosphere, and the temperature was lowered to 0° C. After 10 minutes, triethyl amine (11.2 μL, 0.08 mmol) was added, followed by stirring for 5 minutes. Acetate chloride (5.70 μL, 0.08 mmol) was slowly added at the same temperature, followed by stirring for 1 hour while the temperature was continuously maintained at 0° C. The presence or absence of the reaction was checked by TLC. Upon the completion of the reaction, the reaction was terminated by 1.0 mL of distilled water, followed by extraction three times with dichloromethane. The organic layer was washed once with a saturated sodium chloride solution, dried over anhydrous sodium sulfate, evaporated under reduced pressure, and then separated by silica gel chromatography (ethyl acetate/hexane=1/2 to 1/1), to give (E)-methyl-2-acetoxy-5-(3-oxo-3-(2-oxo-2,5-dihydro-1H-pyrrol-1-yl)prop-1-en-1-yl)benzoate (Compound 4) (5.0 mg, 43.5%) as a yellow solid.

1H NMR (400 MHz, Chloroform-d) δ 8.24 (d, J=2.2 Hz, 1H), 8.05 (d, J=15.8 Hz, 1H), 7.89 (d, J=15.8 Hz, 1H), 7.85 (dd, J=8.4, 2.3 Hz, 1H), 7.37 (dt, J=6.2, 2.1 Hz, 1H), 7.16 (d, J=8.4 Hz, 1H), 6.23 (dt, J=6.1, 1.9 Hz, 1H), 4.55 (t, J=2.0 Hz, 2H), 3.91 (s, 3H), 2.37 (s, 3H).

Preparative Example 6: Synthesis of (E)-methyl-5-(3-acetamido-3-oxoprop-1-en-1-yl)-2-methoxybenzoate (Compound 6)

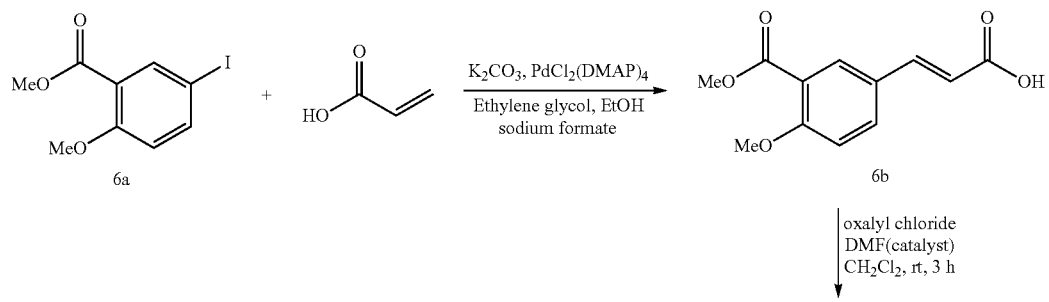

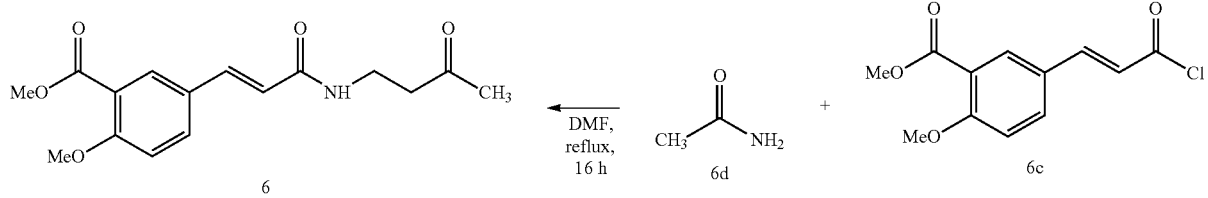
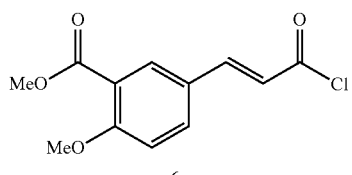

(E)-methyl-5-(3-chloro-3-oxopro-1-pen-1-yl)-2-methoxybenzoate (Compound 6c) (0.22 g, 0.85 mmol) was added into a 25-mL round-bottom flask under argon atmosphere, and charged with dimethyl formamide (12.00 mL). Then, acetamide (0.06 mL, 1.23 mmol) was added, followed by stirring under reflux for 16 hours. Upon the completion of the reaction, the temperature was lowered to room temperature, and the mixture was evaporated under reduced pressure to remove the solvent, and then separated by silica gel chromatography (ethyl acetate/hexane=1/2 to 1/1), to give (E)-methyl-5-(3-acetamide-3-oxoprop-1-en-1-yl)-2-methoxybenzoate (Compound 6) (30 mg, 12.7%) as a white solid.

1H NMR (400 MHz, Chloroform-d) δ 8.11 (s, 1H), 8.03 (d, J=2.4 Hz, 1H), 7.77 (d, J=15.6 Hz, 1H), 7.68 (dd, J=8.8, 2.5 Hz, 1H), 7.01 (d, J=8.7 Hz, 1H), 6.79 (d, J=15.7 Hz, 1H), 3.96 (s, 3H), 3.92 (s, 3H), 2.45 (s, 3H).

Preparative Example 7: Synthesis of (E)-methyl-5-(3-(allylamino)-3-oxoprop-1-en-1-yl)-2-methoxybenzoate (Compound 7)

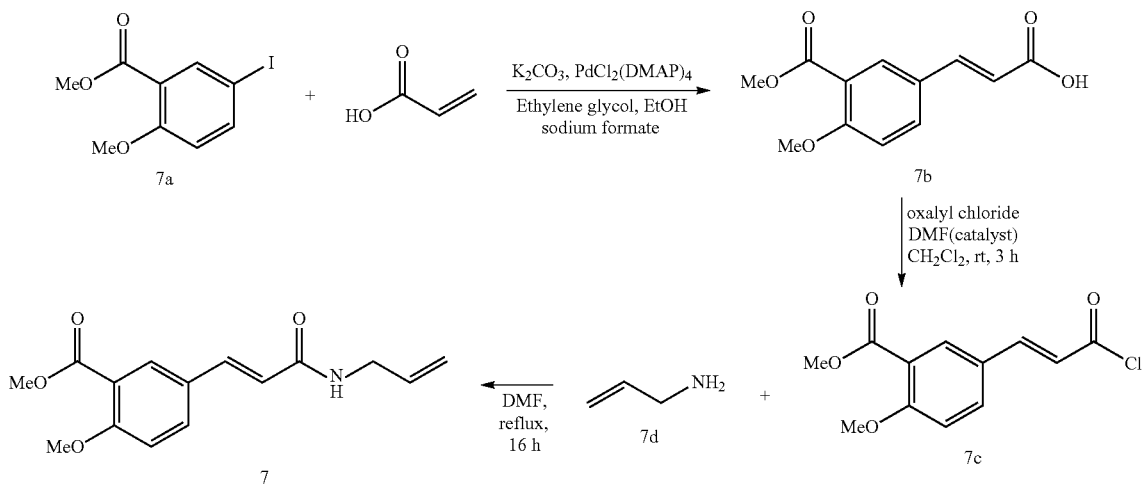

(E)-methyl-5-(3-chloro-3-oxopro-1-pen-1-yl)-2-methoxybenzoate (Compound 7c) (0.22 g, 0.85 mmol) was added into a 25-mL round-bottom flask under argon atmosphere, and charged with diethyl ether (2.50 mL). Then, the temperature was lowered to 0° C., and an allyl amine (7d) (0.64 mL, 8.50 mmol) was slowly added, followed by stirring at the same temperature for 10 minutes. Upon the completion of the reaction, the mixture was evaporated under reduced pressure to remove the solvent, and then separated by silica gel chromatography (ethyl acetate/hexane=1/3 to 1/2), to give (E)-methyl-5-(3-(allylamino)-3-oxoprop-1-en-1-yl)-2-methoxybenzoate (Compound 7) (172 mg, 73.5%) as a white solid.

1H NMR (400 MHz, Chloroform-d) δ 7.99 (d, J=2.4 Hz, 1H), 7.63-7.56 (m, 2H), 6.98 (d, J=8.7 Hz, 1H), 6.34 (d, J=15.6 Hz, 1H), 5.90 (ddt, J=17.1, 10.2, 5.6 Hz, 1H), 5.63 (s, 1H), 5.29-5.13 (m, 2H), 4.03 (tt, J=5.8, 1.5 Hz, 2H), 3.94 (s, 3H), 3.91 (s, 3H).

Preparative Example 8: Synthesis of (E)-methyl-2-methoxy-5-(3-oxo-3-(2-oxopiperidin-1-yl)prop-1-en-1-yl)benzoate (Compound 8)

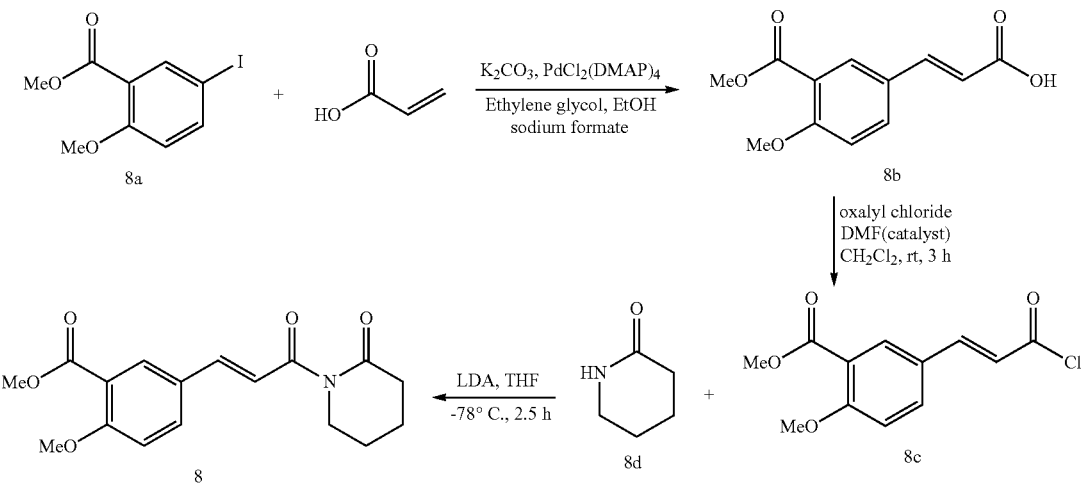

2-Piperidinone (Compound 8d) (0.15 g, 1.53 mmol) was added into a 25-mL round-bottom flask under argon atmosphere, and charged with tetrahydrofuran (2.00 mL). Then, the temperature was lowered to −78° C., and LDA (0.80 mL, 1.53 mmol, 2.0 M solution) was added dropwise, followed by stirring for 45 minutes. (E)-methyl-5-(3-chloro-3-oxo-pro-1-pen-1-yl)-2-methoxybenzoate (Compound 8c) (0.32 g, 1.27 mmol) dissolved in tetrahydrofuran (1.60 mL) was slowly added at −78° C., followed by stirring for 1 hour. Upon the completion of the reaction, the remaining LDA was decomposed by 1 N hydrochloric acid, followed by extraction twice with ethyl acetate. The ethyl acetate layer was washed once with a saturated sodium chloride solution, dried over anhydrous sodium sulfate, evaporated under reduced pressure, and then separated by column chromatography (ethyl acetate/hexane=1/2.5 to 1/2), to give (E)-methyl-2-methoxy-5-(3-oxo-3-(2-oxopiperidin-1-yl)prop-1-en-1-yl)benzoate (Compound 8) (215 mg, 53.5%) as a white solid.

$^1$H NMR (400 MHz, Chloroform-d) δ 8.00 (d, J=2.3 Hz, 1H), 7.69-7.64 (m, 2H), 7.36 (d, J=15.6 Hz, 1H), 6.98 (d, J=8.7 Hz, 1H), 3.94 (s, 3H), 3.90 (s, 3H), 3.80 (td, J=5.2, 4.2, 2.2 Hz, 2H), 2.65-2.57 (m, 2H), 1.95-1.84 (m, 4H).

Preparative Example 9: Synthesis of Compound 9

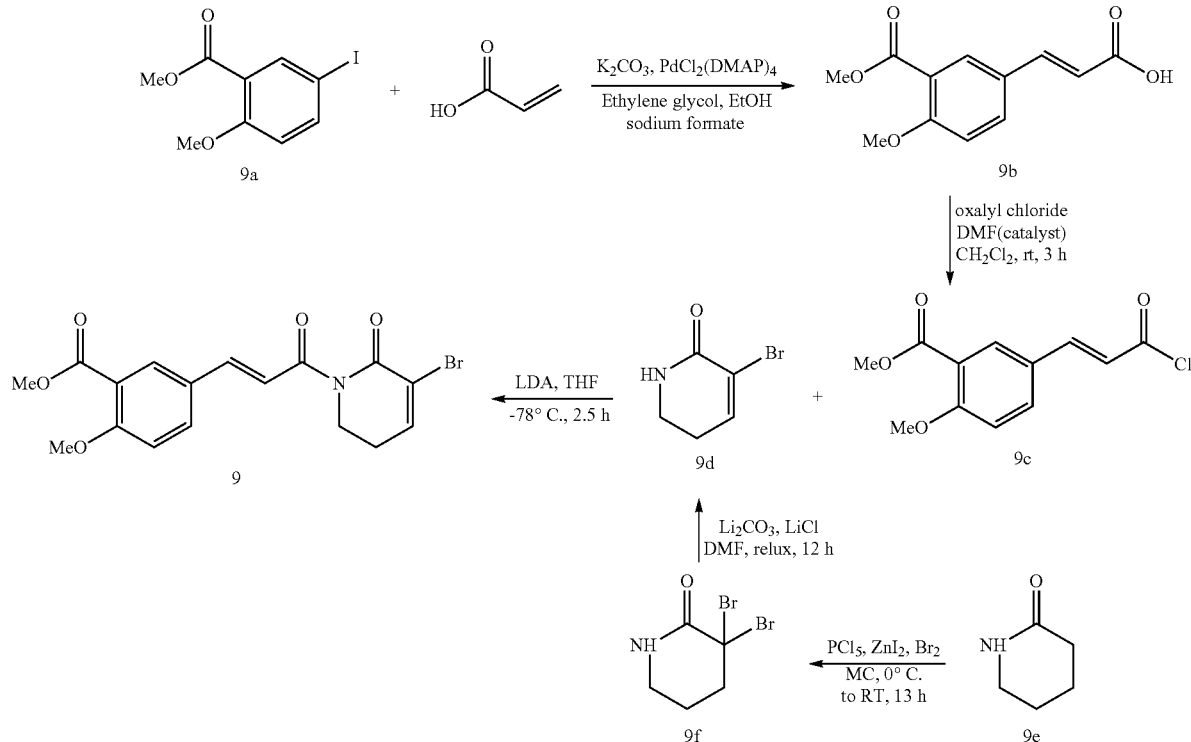

9-1: Preparation of 3,3-dibromopiperidin-2-one (Compound 9f)

Piperidin-2-one (Compound 9e) (2.00 g, 20.18 mmol) was added into a 100-mL round-bottom flask under argon atmosphere, and charged with dichloromethane (40.00 mL). Then, the temperature was lowered to 0° C., and phosphorus pentachloride (8.40 g, 40.36 mmol) was slowed added for 5 minutes, followed by stirring for 5 minutes. Zinc iodide (0.20 g, 0.61 mmol) was added at the same temperature, and then the temperature was raised to room temperature, followed by stirring for 1 hour. After 1 hour, diatomic bromine (2.20 mL, 40.36 mmol) dissolved in dichloromethane (20.00 mL) was slowly added, followed by stirring at the same temperature for 12 hours. Upon the completion of the reaction, the temperature was lowered to room temperature, and then the mixture was added to ice water. The aqueous solution layer was extracted five times with dichloromethane. The organic layer was washed once with a saturated sodium chloride solution, dried over anhydrous magnesium sulfate, evaporated under reduced pressure to remove the solvent of the mixture, and then separated by silica gel chromatography (ethyl acetate/hexane=1/2.5 to 1/1), to give 3,3-dibromopiperidin-2-one (Compound 9f) (1.32 g, 25.5%) as a white solid.

1H NMR (400 MHz, Chloroform-d) δ 6.17 (s, 1H), 3.47 (td, J=6.2, 2.4 Hz, 2H), 3.02-2.95 (m, 2H), 2.08-2.01 (m, 2H).

9-2: Preparation of 3-bromo-5,6-dihydropyridin-2(1H)-one (Compound 9d)

3,3-diboromopiperidin-2-one (Compound 9f) (1.32 g, 5.14 mmol) prepared in Preparative Examples 9-1 above was added into a 50-mL round-bottom flask under argon atmosphere, and charged with dimethyl formamide (10.00 mL). Then, lithium carbonate (0.72 g, 9.80 mmol) and lithium chloride (0.22 g, 5.24 mmol) were added, followed by stirring with heating at 120° C. for 13 hours. Upon the completion of the reaction, the temperature was lowered to room temperature, and then the mixture was added to ice water. The aqueous solution layer was extracted three times with dichloromethane. The organic layer was washed once with a saturated sodium chloride solution, dried over anhydrous magnesium sulfate, and then separated by silica gel chromatography (ethyl acetate/hexane=1/1.5 to 1/1), to give 3-boromo-5,6-dihydropyridin-2(1H)-one (Compound 9d) (0.36 g, 39.9%) as a bright brown solid.

1H NMR (400 MHz, Chloroform-d) δ 7.05 (t, J=4.6 Hz, 1H), 6.96 (s, 1H), 3.49 (td, J=7.1, 2.8 Hz, 2H), 2.43 (td, J=7.1, 4.5 Hz, 2H)

9-3: Preparation of (E)-methyl-5-(3-(3-bromo-2-oxo-5,6-dihydropyridin-1(2H)-yl)-3-oxoprop-1-en-1-yl)-2-methoxybenzoate (Compound 9)

3-Bromo-5,6-dihydropyridin-2 (1H)-one (Compound 9d) (0.14 g, 0.77 mmol) prepared in Preparative Example 9-2 above was added into a 25-mL round-bottom flask under argon atmosphere, and charged with tetrahydrofuran (1.50 mL). Then, the temperature was lowered to −78° C., and LDA (0.40 mL, 0.77 mmol, 2.0 M solution) was added dropwise, followed by stirring for 45 minutes. (E)-methyl-5-(3-chloro-3-oxopro-1-pen-1-yl)-2-methoxybenzoate (Compound 9c) (0.16 g, 0.64 mmol) dissolved in tetrahydrofuran (1.50 mL) was slowly added at −78° C., followed by stirring for 1 hour. Upon the completion of the reaction, the remaining LDA was decomposed by 1 N hydrochloric acid, followed by extraction twice with ethyl acetate. The ethyl acetate layer was washed once with a saturated sodium chloride solution, dried over anhydrous sodium sulfate, evaporated under reduced pressure, and then separated by column chromatography (ethyl acetate/hexane=1/2 to 1/1), to give (E)-methyl-5-(3-(3-boromo-2-oxo-5,6-dihydroxy-pyridin-1(2H)-yl)-3-oxoprop-1-en-1-yl)-2-methoxybenzoate (Compound 9) (91 mg, 36.1%) as a white solid.

1H NMR (400 MHz, Chloroform-d) δ 8.01 (d, J=2.3 Hz, 1H), 7.77-7.68 (m, 2H), 7.42 (d, J=15.6 Hz, 1H), 7.36 (t, J=4.6 Hz, 1H), 6.98 (d, J=8.7 Hz, 1H), 4.10 (t, J=6.5 Hz, 2H), 3.95 (s, 3H), 3.91 (s, 3H), 2.53 (td, J=6.5, 4.5 Hz, 2H).

Preparative Example 10: Synthesis of (E)-methyl-5-(3-(3-bromo-2-oxo-5,6-dihydropyridin-1(2H)-yl)-3-oxoprop-1-en-1-yl)-2-hydroxybenzoate (Compound 10)

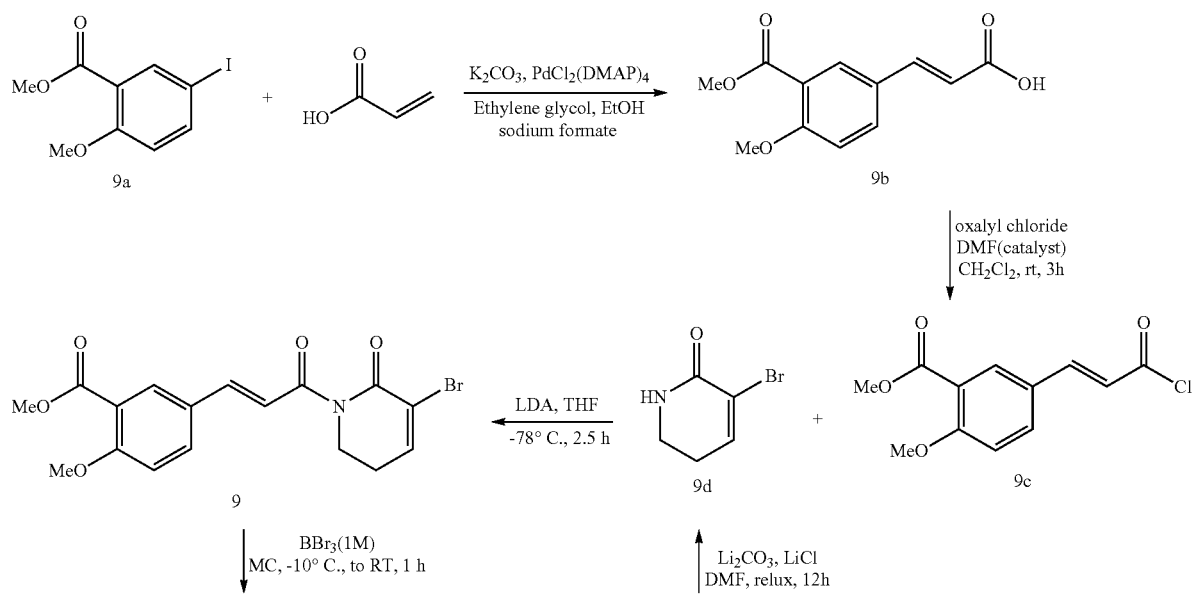

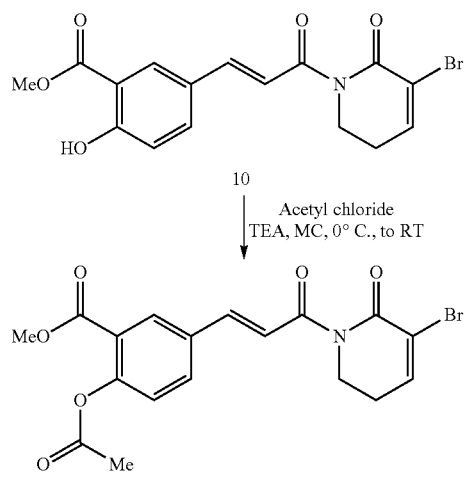
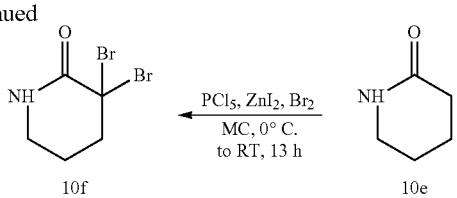

E)-methyl-5-(3-(3-bromo-2-oxo-5,6-dihydropyridin-1(2H)-yl)-3-oxoprop-1-en-1-yl)-2-methoxybenzoate (Compound 9) (220 mg, 0.56 mmol) prepared in Preparative Example 9 above and tetrahydrofuran (10.0 mL) were added into a round-bottom flask under argon atmosphere, and the temperature was lowered to −10° C. After 10 minutes, a tribromoborane solution (1.0 M dichloromethane solution, 1.60 mL, 1.67 mmol) was slowly added, followed by stirring for 1 hours, and then the reaction temperature was gently adjusted to room temperature. The presence or absence of the reaction was checked by TLC. Upon the completion of the reaction, the reaction temperature was again adjusted to 0° C., and the reaction was terminated using 1.50 mL of a 1 N hydrochloric acid solution. Stirring was further conducted at the same temperature for 10 minutes, and then extraction was three times conducted with dichloromethane. The organic layer was washed once with a saturated sodium chloride solution, dried over anhydrous sodium sulfate, evaporated under reduced pressure, and then separated by silica gel chromatography (ethyl acetate/hexane=1/3 to 1/2), to give (E)-methyl-5-(3-(3-bromo-2-oxo-5,6-dihydropyridin-1(2H)-yl)-3-oxoprop-1-en-1-yl)-2-hydroxybenzoate (Compound 10) (76.5 mg, 35.9%) as a white solid.

$^1$H NMR (400 MHz, Chloroform-d) δ 11.03 (s, 1H), 8.07 (d, J=2.3 Hz, 1H), 7.76-7.68 (m, 2H), 7.41 (d, J=15.6 Hz, 1H), 7.36 (t, J=4.6 Hz, 1H), 7.00 (d, J=8.6 Hz, 1H), 4.10 (t, J=6.5 Hz, 2H), 3.99 (s, 3H), 2.53 (td, J=6.5, 4.6 Hz, 2H).

Preparative Example 11: Synthesis of (E)-methyl-2-acetoxy-5-(3-(3-bromo-2-oxo-5,6-dihydropyridin-1(2H)-yl)-3-oxoprop-1-en-1-yl)benzoate (Compound 11)

(E)-methyl-5-(3-(3-bromo-2-oxo-5,6-dihydropyridin-1(2H)-yl)-3-oxoprop-1-en-1-yl)-2-hydroxybenzoate (Compound 10) (30 mg, 0.08 mmol) prepared in Preparative Example 10 and dichloromethane (2.0 mL) were added into a round-bottom flask under argon atmosphere, and the temperature was lowered to 0° C. After 10 minutes, triethyl amine (20.3 μL, 0.16 mmol) was added, followed by stirring for 5 minutes. Acetate chloride (11.4 μL, 0.16 mmol) was slowly added at the same temperature, and stirring was conducted for 1 hour while the temperature was continuously maintained at 0° C. The presence or absence of the reaction was checked by TLC, and after the reaction, the reaction was terminated by 2.0 mL of distilled water. Thereafter, extraction was three times conducted with dichloromethane. The organic layer was washed once with a saturated sodium chloride solution, dried over anhydrous sodium sulfate, evaporated under reduced pressure, and then separated by silica gel chromatography (ethyl acetate/hexane=1/3 to 1/2), to give (E)-methyl-2-acetoxy-5-(3-(3-bromo-2-oxo-5,6-dihydropyridin-1(2H)-yl)-3-oxoprop-1-en-1-yl)benzoate (Compound 11) (34.0 mg, 87.4%) as a yellow solid.

$^1$H NMR (400 MHz, Chloroform-d) δ 8.20 (d, J=2.2 Hz, 1H), 7.78 (dd, J=8.5, 2.4 Hz, 1H), 7.74 (d, J=15.7 Hz, 1H), 7.49 (d, J=15.6 Hz, 1H), 7.37 (t, J=4.6 Hz, 1H), 7.13 (d, J=8.4 Hz, 1H), 4.11 (t, J=6.5 Hz, 2H), 3.90 (s, 3H), 2.54 (td, J=6.4, 4.5 Hz, 2H), 2.36 (s, 3H).

Preparative Example 12: Synthesis of (E)-methyl-5-(3-(3-chloro-2-oxo-5,6-dihydropyridin-1(2H)-yl)-3-oxoprop-1-en-1-yl)-2-hydroxybenzoate (Compound 12)

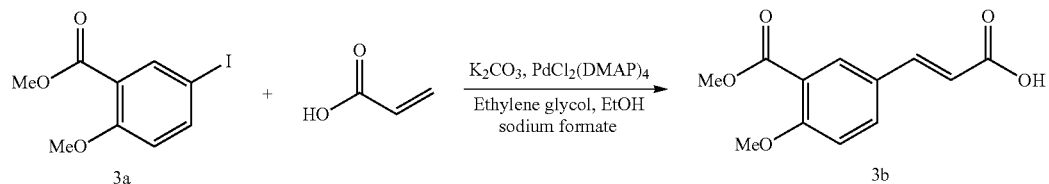

-continued

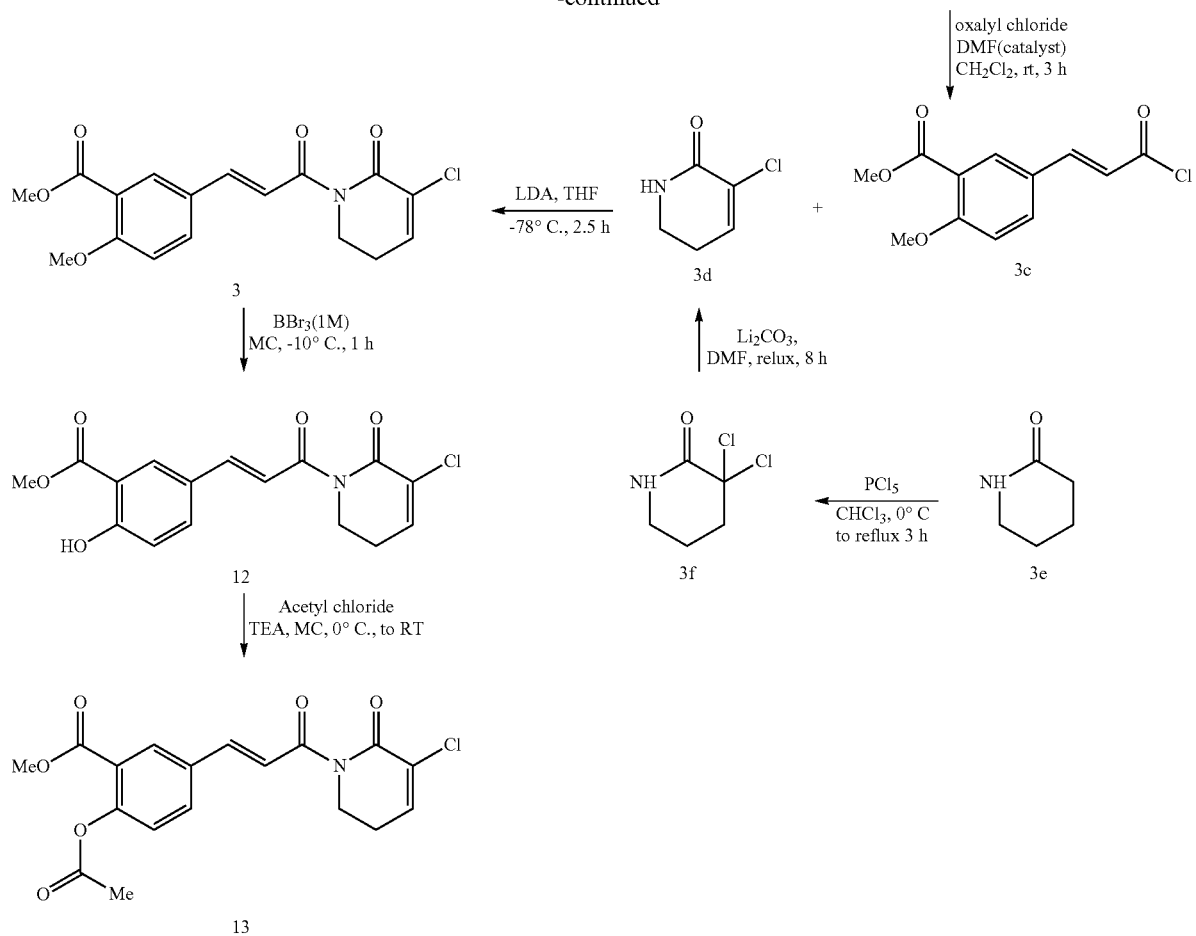

(E)-methyl-5-(3-(3-chloro-2-oxo-5,6-dihydroxypyridin-1(2H)-yl)-3-oxoprop-1-en-1-yl)-2-methoxybenzoate (Compound 3) (240 mg, 0.69 mmol) prepared in Preparative Example 3 above and tetrahydrofuran (13.0 mL) were added into a round-bottom flask under argon atmosphere, and the temperature was lowered to −10° C. After 10 minutes, a triboromoboron solution (1.0 M dichloromethane solution, 2.06 mL, 2.06 mmol) was slowly added, followed by stirring for 1 hour, and the reaction temperature was gently adjusted to room temperature. The presence or absence of the reaction was checked by TLC. Upon the completion of the reaction, the reaction temperature was again adjusted to 0° C., and the reaction was terminated using 1.50 mL of a 1 N hydrochloride acid solution. Stirring was further conducted at the same temperature for 10 minutes, and then extraction was three times conducted with dichloromethane. The organic layer was washed once with a saturated sodium chloride solution, dried over anhydrous sodium sulfate, evaporated under reduced pressure, and then separated by silica gel chromatography (ethyl acetate/hexane=1/3 to 1/2), to give (E)-methyl-5-(3-(3-chloro-2-oxo-5,6-dihydropyridin-1(2H)-yl)-3-oxoprop-1-en-1-yl)-2-hydroxybenzoate (Compound 12) (55.7 mg, 24.1%) as a white solid.

$^1$H NMR (400 MHz, Chloroform-d) δ 11.03 (s, 1H), 8.08 (d, J=2.5 Hz, 1H), 7.76-7.69 (m, 2H), 7.42 (d, J=15.6 Hz, 1H), 7.10 (t, J=4.6 Hz, 1H), 7.00 (d, J=8.6 Hz, 1H), 4.09 (t, J=6.5 Hz, 2H), 3.99 (s, 3H), 2.57 (td, J=6.5, 4.6 Hz, 2H).

Preparative Example 13: Synthesis of (E)-methyl-2-acetoxy-5-(3-(3-chloro-2-oxo-5,6-dihydropyridin-1(2H)-yl)-3-oxoprop-1-en-1-yl)benzoate (Compound 13)

(E)-methyl-5-(3-(3-chloro-2-oxo-5,6-dihydropyridin-1(2H)-yl)-3-oxoprop-1-en-1-yl)-2-hydroxybenzoate (Compound 12) (41 mg, 0.12 mmol) prepared in Preparative Example 12 above and dichloromethane (2.0 mL) were added into a round-bottom flask under argon atmosphere, and the temperature was lowered to 0° C. After 10 minutes, triethyl amine (33.5 μL, 0.24 mmol) was added, followed by stirring for 5 minutes. Acetate chloride (17.1 μL, 0.24 mmol) was slowly added at the same temperature, and stirring was conducted for 1 hour while the temperature was continuously maintained at 0° C. The presence or absence of the reaction was checked by TLC, and after the reaction was completed, the reaction was terminated by 2.0 mL of distilled water. Thereafter, extraction was three times conducted with dichloromethane. The organic layer was washed once with a saturated sodium chloride solution, dried over anhydrous sodium sulfate, evaporated under reduced pressure, and then separated by silica gel chromatography (ethyl acetate/hexane=1/3 to 1/2), to give (E)-methyl-2-acetoxy-5-(3-(3-chloro-2-oxo-5,6-dihydropyridin-1(2H)-yl)-3-oxo-prop-1-en-1-yl)benzoate (Compound 13) (30.0 mg, 66.2%) as a yellow solid.

$^1$H NMR (400 MHz, Chloroform-d) δ 8.20 (d, J=2.2 Hz, 1H), 7.81-7.71 (m, 2H), 7.50 (d, J=15.6 Hz, 1H), 7.15-7.09 (m, 2H), 4.10 (t, J=6.5 Hz, 2H), 3.90 (s, 3H), 2.59 (td, J=6.4, 4.6 Hz, 2H), 2.36 (s, 3H).

Preparative Example 14: Synthesis of Compound 14

$^1$H NMR (400 MHz, CDCl$_3$+CD$_3$OD): δ 8.28 (1H, t, J=1.6 Hz), 8.14 (1H, ddd, J=8.4, 2.4, 1.2 Hz), 7.76 (1H, dt, J=8.0, 1.6 Hz), 7.62 (1H, d, J=16.0 Hz), 7.50 (1H, t, J=8.0 Hz), 6.46 (1H, d, J=16.0 Hz).

14-2: Preparation of (E)-1-(3-(3-nitrophenyl)acryloyl)-1H-pyrrol-2(5H)-one (Compound 14)

1H-pyrrol-2(5H)-one (Compound 14d) (0.11 g, 1.25 mmol) was added into a 50-mL round-bottom flask under argon atmosphere, and charged with tetrahydrofuran (1.50

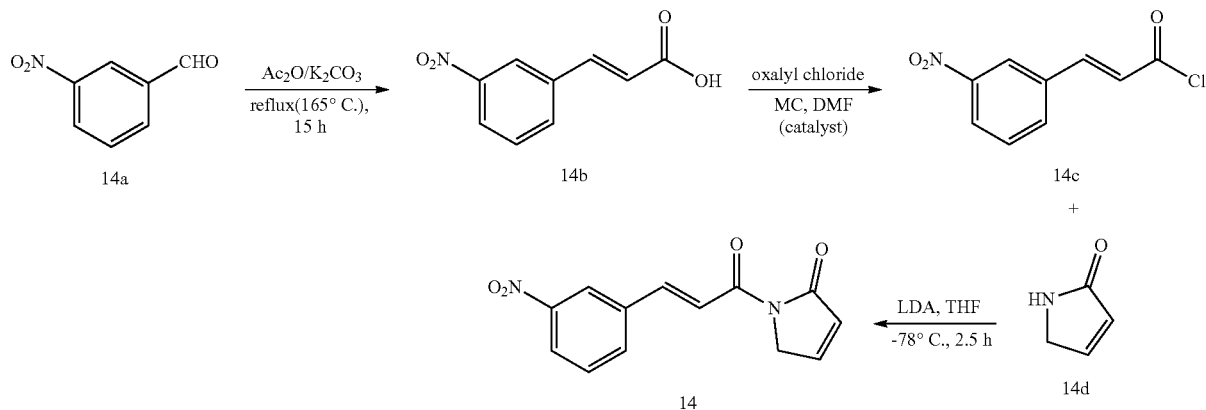

14-1: Preparation of (E)-3-(3-nitrophenyl)acrylic Acid (Compound 14b)

Anhydrous acetic acid (8.0 mL, 84.6 mmol) was slowly added at 0° C. to a round-bottom flask containing potassium carbonate (3.32 g, 24.0 mmol) under argon atmosphere, and the temperature was gently raised to room temperature, followed by stirring for 5 minutes, and then 3-nitrobenzaldehyde (Compound 14a) (3.02 g, 20.0 mmol) was slowly added. The reaction mixture was stirred under reflux at 165° C. for 165 hours. Upon the completion of the reaction, the temperature was lowered to room temperature, and ice water was added. Thereafter, solids were filtered by using a filtration device, washed several times with water, and then dried. The obtained solid mixture was dissolved in an ethyl acetate solvent (30.0 mL), and washed twice with a saturated sodium bicarbonate aqueous solution (20.0 mL), and then the ethyl acetate layer was discarded. The sodium bicarbonate aqueous solution layer was acidified with an aqueous solution of 3 N hydrogen chloride, and then extracted twice with an ethyl acetate solvent. The organic layer was washed once with a saturated sodium chloride solution, dried over anhydrous sodium sulfate, evaporated under reduced pressure, and then sufficiently dried, to give (E)-3-(3-nitrophenyl)acrylic acid (Compound 14b) (2.20 g, 56.8%) as a beige solid.

mL). Then, the temperature was lowered to −78° C., and LDA (0.63 mL, 1.25 mmol, 2.0 M solution) was added dropwise, followed by stirring for 45 minutes. (E)-3-(3-nitrophenyl)acryloyl chloride (Compound 14c) (0.22 g, 1.04 mmol) dissolved in tetrahydrofuran (2.0 mL) was slowly added at −78° C., followed by stirring for 1 hour. Upon the completion of the reaction, the remaining LDA was decomposed by 1 N hydrochloric acid, followed by extraction with ethyl acetate. The ethyl acetate layer was washed with a saturated sodium chloride solution, dried over anhydrous sodium sulfate, evaporated under reduced pressure, and then separated by column chromatography (ethyl acetate/hexane=1/3 to 1/2), to give (E)-1-(3-(3-nitrophenyl) acryloyl)-1H-pyrrol-2 (5H)-one (Compound 14) (81 mg, 30.2%) as a pale brown solid.

$^1$H NMR (400 MHz, Chloroform-d) δ 8.39 (t, J=2.0 Hz, 1H), 8.23 (ddd, J=8.2, 2.3, 1.1 Hz, 1H), 7.83 (dt, J=7.8, 1.4 Hz, 1H), 7.71 (d, J=16.0 Hz, 1H), 7.59 (t, J=7.9 Hz, 1H), 6.57 (d, J=16.0 Hz, 1H), 4.24 (t, J=6.7 Hz, 2H).

$^{13}$C NMR (100 MHz, CDCl$_3$): δ 170.3, 164.6, 148.9, 147.4, 143.0, 136.8, 133.9, 130.1, 127.9, 124.8, 123.4, 121.9, 51.2.

Preparative Example 15: Synthesis of Compound 15

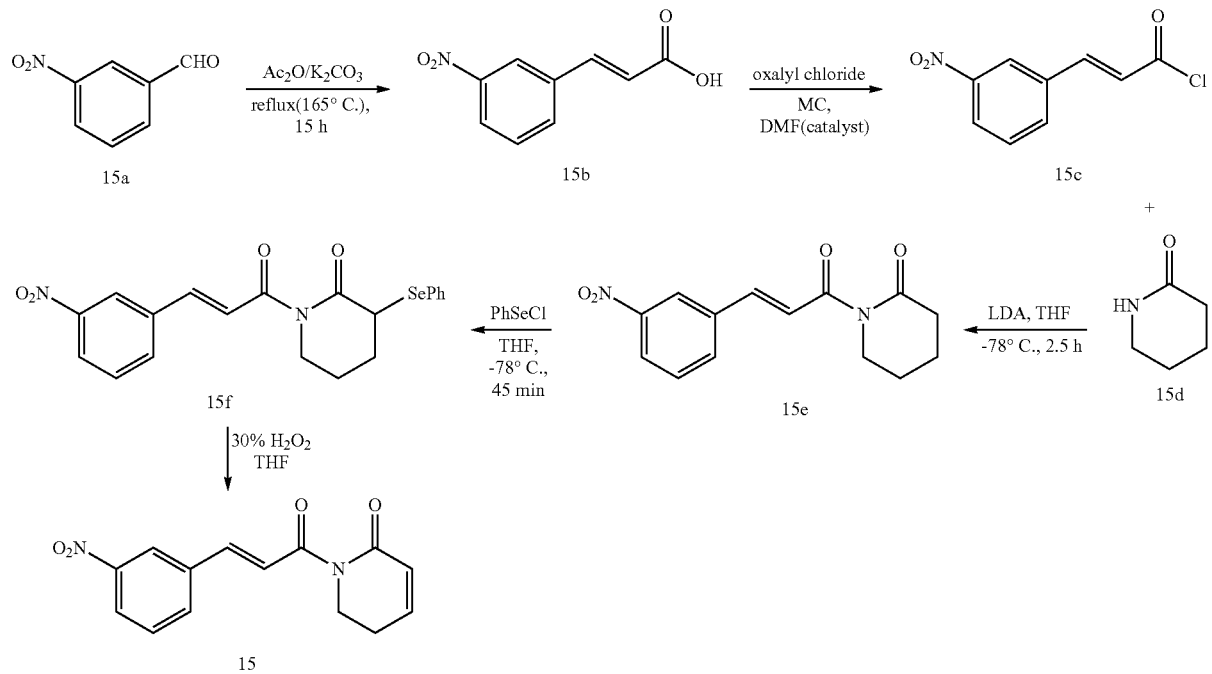

15-1: (E)-1-(3-(3 nitrophenyl)acryloyl)piperidin-2-one (Compound 15e)

2-Piperidinone (Compound 15d) (0.14 g, 1.40 mmol) was added into a 25-mL round-bottom flask under argon atmosphere, and charged with tetrahydrofuran (1.50 mL). Then, the temperature was lowered to −78° C., and LDA (0.70 mL, 1.40 mmol, 2.0 M solution) was added dropwise, followed by stirring for 45 minutes. (E)-3-(3-nitrophenyl)acryloyl chloride (Compound 15c) (0.25 g, 1.16 mmol) dissolved in tetrahydrofuran (1.80 mL) was slowly added at −78° C., followed by stirring for 1 hour. Upon the completion of the reaction, the remaining LDA was decomposed by 1 N hydrochloric acid, followed by extraction twice with ethyl acetate. The ethyl acetate layer was washed once with a saturated sodium chloride solution, dried over anhydrous sodium sulfate, evaporated under reduced pressure, and then separated by column chromatography (ethyl acetate/hexane=1/2 to 1/1), to give (E)-1-(3-(3-nitrophenyl)acryloyl)piperidin-2-one (Compound 15e) (165 mg, 52.1%) as a white solid.
$^1$H NMR (400 MHz, Chloroform-d) δ 8.39 (t, J=2.0 Hz, 1H), 8.20 (ddd, J=8.1, 2.2, 1.0 Hz, 1H), 7.86 (dt, J=7.8, 1.4 Hz, 1H), 7.67 (d, J=15.7 Hz, 1H), 7.56 (t, J=8.0 Hz, 1H), 7.50 (d, J=15.6 Hz, 1H), 3.82 (ddd, J=6.4, 4.2, 1.5 Hz, 2H), 2.67-2.59 (m, 2H), 1.95-1.86 (m, 4H).

15-2: Preparation of (E)-1-(3-(3-nitrophenyl)acryloyl)-3-(phenylselanyl)piperidin-2-one (Compound 15f)

(E)-1-(3-(3-nitrophenyl)acryloyl)piperidin-2-one (Compound 15e) (0.16 g, 0.60 mmol) prepared in Preparative Example 15-1 above was added into a 25-mL round-bottom flask under argon atmosphere, and charged with tetrahydrofuran (3.50 mL). Then, the temperature was lowered to −78° C., and LDA (0.40 mL, 0.78 mmol, 2.0 M solution) was added dropwise, followed by stirring for 45 minutes. Phenylselenyl chloride (0.13 g, 0.66 mmol) dissolved in tetrahydrofuran (3.50 mL) was slowly added at −78° C., followed by stirring for 4 hours. Upon the completion of the reaction, the remaining LDA was decomposed by addition of water, followed by additional stirring at 0° C. for 15 minutes and extraction twice with dichloromethane. The organic layer was washed once with a saturated sodium chloride solution, dried over anhydrous sodium sulfate, evaporated under reduced pressure, and then separated by silica gel chromatography (ethyl acetate/hexane=1/4 to 1/3), to give (E)-1-(3-(3-nitrophenyl)acryloyl)-3-(phenylselanyl)piperidin-2-one (Compound 15f) (30 mg, 11.7%) as a white solid.
$^1$H NMR (400 MHz, Chloroform-d) δ 8.33 (t, J=2.0 Hz, 1H), 8.21 (ddd, J=8.2, 2.3, 1.0 Hz, 1H), 7.78 (dt, J=7.8, 1.4 Hz, 1H), 7.72-7.69 (m, 2H), 7.65 (d, J=15.6 Hz, 1H), 7.56 (t, J=8.0 Hz, 1H), 7.43-7.34 (m, 3H), 7.10 (d, J=15.6 Hz, 1H), 4.13 (ddd, J=5.2, 4.2, 1.0 Hz, 1H), 4.08-3.95 (m, 1H), 3.70 (ddd, J=14.0, 9.7, 4.6 Hz, 1H), 2.46-2.28 (m, 1H), 2.25-2.05 (m, 2H), 1.90 (dt, J=14.3, 5.1 Hz, 1H).

15-3: Preparation of (E)-1-(3-(3-nitrophenyl)acryloyl)-5,6-dihydropyridin-2(1H)-one (Compound 15)

(E)-1-(3-(3-nitrophenyl) acryloyl)-3-(phenylselanyl)piperidin-2-one (Compound 15f) (28 mg, 0.07 mmol) prepared in Preparative Example 15-2 was added into a 25-mL round-bottom flask under argon atmosphere, and charged with tetrahydrofuran (1.00 mL). Then, the temperature was lowered to 0° C., and hydrogen peroxide (20 μL, 0.18 mmol, 30% solution) was added dropwise, followed by stirring for 15 minutes. Thereafter, the temperature was raised to room temperature, followed by additional stirring for 30 minutes. Upon the completion of the reaction, a saturated sodium bicarbonate solution was added, followed by extraction twice with dichloromethane. The organic layer was washed once with a saturated sodium chloride solution, dried over anhydrous sodium sulfate, evaporated under reduced pressure, and then separated by silica gel chromatography (ethyl acetate/hexane=1/2), to give (E)-1-(3-(3-nitrophenyl)acryloyl)-5,6-dihydropyridin-2(1H)-one (Compound 15) (7.10 mg, 37.4%) as a white solid.

¹H NMR (400 MHz, Chloroform-d) δ 8.41 (t, J=2.0 Hz, 1H), 8.21 (ddd, J=8.1, 2.2, 1.0 Hz, 1H), 7.88 (d, J=7.7 Hz, 1H), 7.73 (d, J=15.7 Hz, 1H), 7.60-7.54 (m, 2H), 7.03-6.94 (m, 1H), 6.07 (dt, J=9.7, 1.9 Hz, 1H), 4.06 (t, J=6.5 Hz, 2H), 2.51 (tdd, J=6.4, 4.2, 1.9 Hz, 2H).

Preparative Example 16: Synthesis of (E)-3-chloro-1-(3-(3-nitrophenyl) acryloyl)-5,6-dihydropyridin-2(1H)-one (Compound 16)

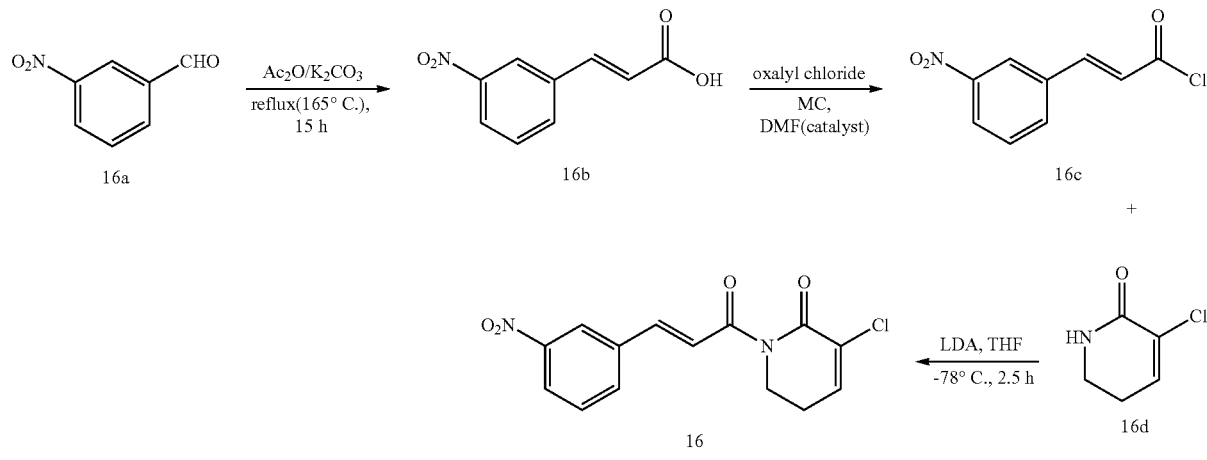

3-Chloro-5,6-dihydropyridin-2 (1H)-one (Compound 16d) (0.17 g, 1.31 mmol) was added into a 25-mL round-bottom flask under argon atmosphere, and charged with tetrahydrofuran (2.0 mL). Then, the temperature was lowered to −78° C., and LDA (0.70 mL, 1.31 mmol, 2.0 M solution) was added dropwise, followed by stirring for 45 minutes. (E)-3-(3-nitrophenyl)acryloyl chloride (Compound 16c) (0.23 g, 1.09 mmol) dissolved in tetrahydrofuran (1.50 mL) was slowly added at −78° C., followed by stirring for 1 hour. Upon the completion of the reaction, the remaining LDA was decomposed by 1 N hydrochloric acid, followed by extraction twice with ethyl acetate. The ethyl acetate layer was washed once with a saturated sodium chloride solution, dried over anhydrous sodium sulfate, evaporated under reduced pressure, and then separated by column chromatography (ethyl acetate/hexane=1/2 to 1/1), to give (E)-3-chloro-1-(3-(3-nitrophenyl)acryloyl)-5,6-dihydropyridin-2(1H)-one (Compound 16) (135 mg, 40.7%) as a pale yellow solid.

¹H NMR (400 MHz, Chloroform-d) δ 8.40 (t, J=2.0 Hz, 1H), 8.23 (ddd, J=8.2, 2.3, 1.0 Hz, 1H), 7.90 (d, J=7.7 Hz, 1H), 7.75 (d, J=15.7 Hz, 1H), 7.61-7.53 (m, 2H), 7.13 (t, J=4.6 Hz, 1H), 4.11 (t, J=6.5 Hz, 2H), 2.60 (td, J=6.5, 4.6 Hz, 2H).

Preparative Example 17: Synthesis of (E)-3-bromo-1-(3-(3-nitrophenyl) acryloyl)-5,6-dihydropyridin-2(1H)-one (Compound 17)

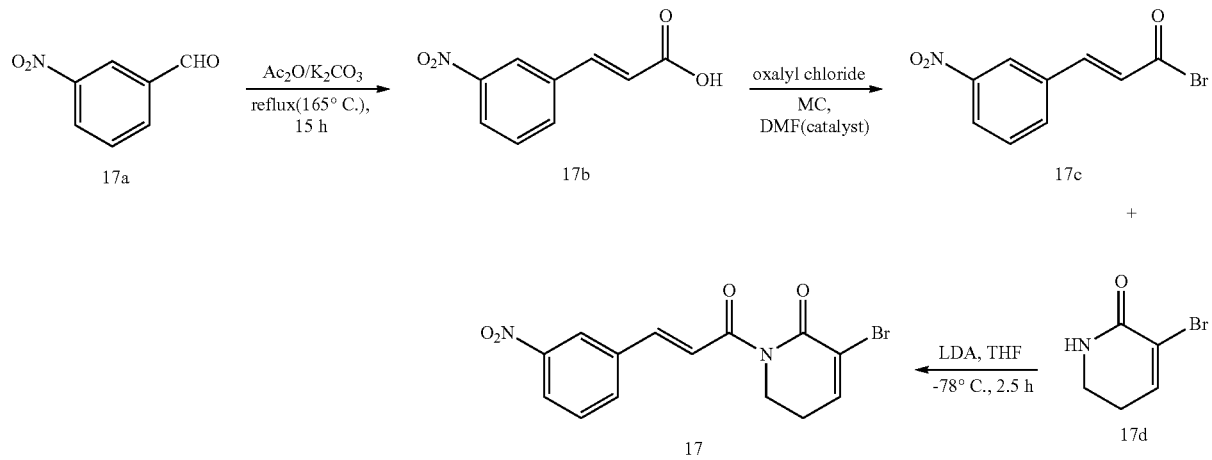

3-Bromo-5,6-dihydropyridin-2 (1H)-one (Compound 17d) (0.22 g, 1.25 mmol) was added into a 25-mL round-bottom flask under argon atmosphere, and charged with tetrahydrofuran (2.0 mL). Then, the temperature was lowered to −78° C., and LDA (0.63 mL, 1.25 mmol, 2.0 M solution) was added dropwise, followed by stirring for 45 minutes. (E)-3-(3-nitrophenyl)acryloyl chloride (Compound 17c) (0.22 g, 1.04 mmol) dissolved in tetrahydrofuran (1.50 mL) was slowly added at −78° C., followed by stirring for 1 hour. Upon the completion of the reaction, the remaining LDA was decomposed by 1 N hydrochloric acid, followed by extraction twice with ethyl acetate. The ethyl acetate layer was washed once with a saturated sodium chloride solution, dried over anhydrous sodium sulfate, evaporated under reduced pressure, and then separated by column chromatography (ethyl acetate/hexane=1/2.5 to 1/2), to give (E)-3-bromo-1-(3-(3-nitrophenyl)acryloyl)-5,6-dihydro-pyridin-2(1H)-one (Compound 17) (110 mg, 30.1%) as a pale yellow solid.

$^1$H NMR (400 MHz, Chloroform-d) δ 8.40 (t, J=2.0 Hz, 1H), 8.22 (ddd, J=8.1, 2.3, 1.0 Hz, 1H), 7.90 (d, J=7.6 Hz, 1H), 7.75 (d, J=15.6 Hz, 1H), 7.62-7.53 (m, 2H), 7.39 (t, J=4.6 Hz, 1H), 4.12 (t, J=6.5 Hz, 2H), 2.56 (td, J=6.4, 4.6 Hz, 2H).

Preparative Example 18: Synthesis of Compound 18 the ethyl acetate layer was discarded. The sodium bicarbonate aqueous solution layer was acidified with an aqueous solution of 3N hydrogen chloride and then extracted twice with an ethyl acetate solvent. The organic layer was washed once with a saturated sodium chloride solution, dried over anhydrous magnesium sulfate, evaporated under reduced pressure, and then sufficiently dried, to give (E)-3-(2,3-dehydrobenzo[b][1,4]dioxin-6-yl)acrylic acid (Compound 18b) (0.48 g, 38.9%) as a white solid.

$^1$H NMR (400 MHz, CDCl$_3$): δ 7.67 (1H, d, J=16.0 Hz), 7.08 (1H, d, J=2.0 Hz), 7.06 (1H, dd, J=8.4, 2.0 Hz), 6.88 (1H, d, J=8.4 Hz), 6.29 (1H, d, J=15.6 Hz), 4.31-4.26 (4H, m).

18-2: Preparation of (E)-1-(3-(2,3-dihydrobenzo[b][1,4]dioxin-6-yl)acryloyl)-1H-pyrrol-2(5H)-one (Compound 18)

1H-pyrrol-2(5H)-one (Compound 18d) (58 mg, 0.69 mmol) was added into a 50-mL round-bottom flask under argon atmosphere, and charged with tetrahydrofuran (1.0 mL). Then, the temperature was lowered to −78° C., and LDA (0.35 mL, 0.69 mmol, 2.0 M solution) was added dropwise, followed by stirring for 45 minutes. (E)-3-(2,3-

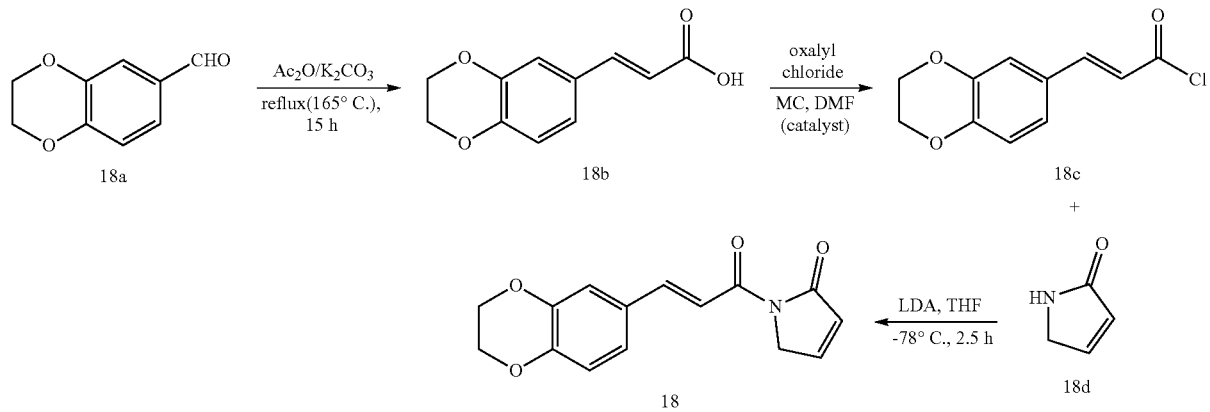

18-1: Preparation of (E)-3-(2,3-dihydrobenzo[b][1,4]dioxin-6-yl)acrylic Acid (Compound 18b)

Anhydrous acetic acid (4.0 mL, 42.2 mmol) was slowly added at 0° C. to a round-bottom flask containing potassium carbonate (1.04 g, 7.54 mmol) under argon atmosphere, and the temperature was gently raised to room temperature, followed by stirring for 5 minutes, and then 2,3-dehydrobenzo[b][1,4]dioxin-6-carbaldehyde (Compound 18a) (0.99 g, 6.03 mmol) was slowly added. The reaction mixture was stirred under reflux at 165° C. for 15 hours. Upon the completion of the reaction, the temperature was lowered to room temperature (solid generating within 1 hour), and ice water was added. Thereafter, solids were filtered by using a filtration device, washed several times with water, and then dried. The obtained solid mixture was dissolved in an ethyl acetate solvent (30.0 mL), and washed twice with a saturated sodium bicarbonate aqueous solution (20.0 mL), and then dehydrobenzo[b][1,4]dioxin-6-yl) acryloyl chloride (Compound 18c) (120 mg, 0.58 mmol) dissolved in tetrahydrofuran (1.2 mL) was slowly added at −78° C., followed by stirring for 1 hour. Upon the completion of the reaction, the remaining LDA was decomposed by 1 N hydrochloric acid, followed by extraction with ethyl acetate. The ethyl acetate layer was washed with a saturated sodium chloride solution, dried over anhydrous magnesium sulfate, evaporated under reduced pressure, and then separated by column chromatography (ethyl acetate/hexane=1/2 to 1/1), to give (E)-1-(3-(2,3-dehydrobenzo[b][1,4]dioxin-6-yl)acryloyl)-1H-pyrrol-2(5H)-one (Compound 18) (10 mg, 10.1%) as a white solid.

$^1$H NMR (400 MHz, Chloroform-d) δ 7.90 (d, J=15.7 Hz, 1H), 7.80 (d, J=15.7 Hz, 1H), 7.33 (dt, J=6.1, 2.0 Hz, 1H), 7.21-7.13 (m, 2H), 6.87 (d, J=8.3 Hz, 1H), 6.21 (dt, J=6.1, 1.9 Hz, 1H), 4.52 (t, J=2.0 Hz, 2H), 4.31-4.26 (m, 4H).

$^{13}$C NMR (101 MHz, Chloroform-d) δ 170.21, 165.50, 146.74, 145.99, 145.90, 143.75, 128.68, 128.01, 122.72, 117.74, 117.44, 116.84, 64.68, 64.28, 51.18.

Preparative Example 19: Synthesis of Compound 19
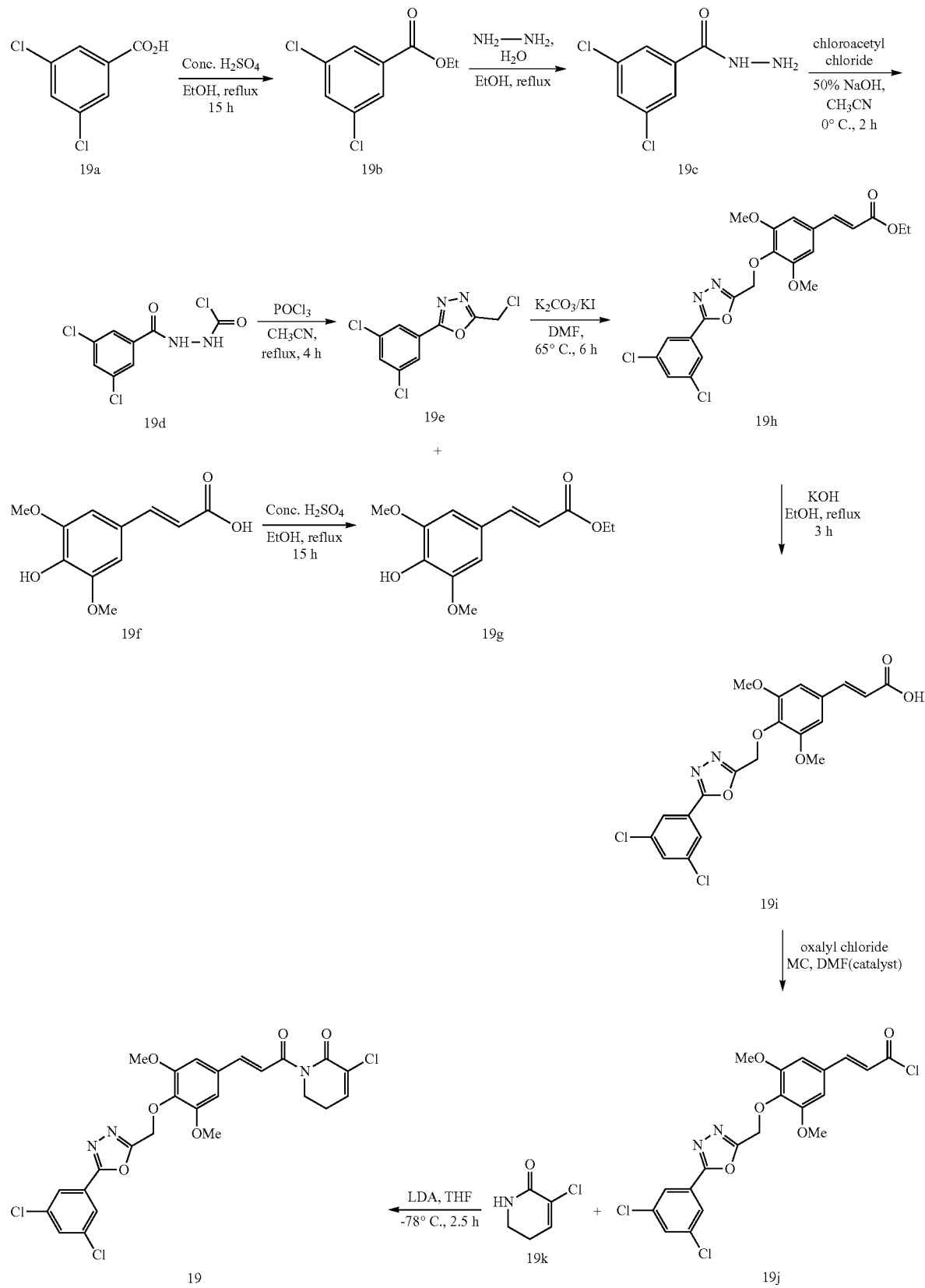

19-1: Preparation of ethyl-3,5-dichlorobenzoate (Compound 19b)

Concentrated sulfuric acid (0.29 mL) was slowly added at 0° C. to 3,5-dichlorobenzoic acid (Compound 19a) (1.05 g, 5.50 mmol) dissolved in an anhydrous ethanol solvent (11.0 mL) under argon atmosphere. The reaction mixture was stirred under reflux at 80° C. for 15 hours. Upon the completion of the reaction, the temperature was lowered to room temperature, and the solvent was all removed by evaporation under reduced pressure. Thereafter, the mixture was dissolved in an ethyl acetate (80.0 mL) solvent, washed twice with a saturated sodium bicarbonate aqueous solution (15.0 mL), twice with water (20.0 mL), and once with a saturated sodium chloride solution (20.0 mL), dried over anhydrous magnesium sulfate, evaporated under reduced pressure, and then sufficiently dried, to give ethyl-3,5-dichlorobenzoate (Compound 19b) (1.15 g, 95.2%) as a solid.

$R_f$=0.75 (ethyl acetate/hexane=1/5)

19-2: Preparation of 3,5-dichlorobenzohydrazide (Compound 19c)

Hydrazine hydrate (0.38 mL, 7.85 mmol) was added to ethyl-3,5-dichlorobenzoate (Compound 19b) (1.15 g, 5.24 mmol) dissolved in anhydrous ethanol solvent (12.0 mL) under argon atmosphere at 0° C. The reaction mixture was stirred under reflux at 80° C. for 15 hours. Upon the completion of the reaction, the temperature was lowered to room temperature, and the solvent was all removed by evaporation under reduced pressure. Ice water was added to the mixture, and then solids were filtered by a filtration device, washed several times with water and hexane, and then sufficiently dried, to give 3.5-dichlorobenzohydrazide (Compound 19c) (0.98 g, 90.4%) as a white solid. The obtained compound was used for a next reaction without purification.

$R_f$=0.21 (ethyl acetate/hexane=1/1)

$^1$H NMR (400 MHz, DMSO-$d_6$): δ 10.00 (1H, br s), 7.83 (2H, d, J=1.6 Hz), 7.79 (1H, t, J=1.6 Hz), 4.59 (2H, br s).

19-3: Preparation of 2-(3,5-dichlorobenzoyl)hydrazinecarbonyl chloride (Compound 19d)

Chloroacetyl chloride (0.45 mL, 5.68 mmol) was added at 0° C. to 3.5-dichlorobenzohydrazide (Compound 19c) (0.98 g, 4.73 mmol) dissolved in an anhydrous acetonitrile solvent (18.0 mL) under argon atmosphere, and immediately, a 40% sodium hydroxide aqueous solution (1.5 eq) was slowly added, followed by further stirring for 2 hours. Upon the completion of the reaction, ice water (20.0 mL) was added, and solids were filtered by a filtration device, washed several times with water, and then sufficiently dried. To completely dry the solid compound, the solids were dissolved in ethyl acetate (200.0 mL), dried over anhydrous magnesium sulfate, and then evaporated under reduced pressure, to give 2-(3,5-dichlorobenzoyl)hydrazine carbonyl chloride (Compound 19d) (0.93 g, 70.0%). The obtained compound was used for a next reaction without other purification.

$R_f$=0.54 (ethyl acetate/hexane=1/1)

19-4: Preparation of 2-(chloromethyl)-5-(3,5-dichlorophenyl)-1,3,4-oxadiazole (Compound 19e)

Phosphoryl chloride (0.62 mL, 6.63 mmol) was added at room temperature to 2-(3,5-dichlorobenzoyl) hydrazinecarbonyl chloride (Compound 19d) (0.93 g, 3.31 mmol) dissolved in anhydrous acetonitrile (18.0 mL) under argon atmosphere, followed by stirring under reflux at 90° C. for 4 hours. Upon the completion of the reaction, the temperature was lowered to room temperature, and the solvent was all removed by evaporation under reduced pressure. A saturated sodium bicarbonate aqueous solution (15.0 mL) was added to the mixture. Thereafter, the resultant mixture was washed three times with an ethyl acetate solvent (50.0 mL), three times with water (30.0 mL), and once with a saturated sodium chloride solution (30.0 mL), dried over anhydrous magnesium sulfate, evaporated under reduced pressure, and then separated by column chromatography (ethyl acetate/hexane=1/10), to give 2-(chloromethyl)-5-(3, 5-dichlorophenyl)-1,3,4,-oxadizole (Compound 19e) (0.68 g, 77.7%) as a white solid.

$R_f$=0.48 (ethyl acetate/hexane=1/5)

$^1$H NMR (400 MHz, CDCl3): δ 7.98 (2H, d, J=2.0 Hz), 7.56 (1H, t, J=2.0 Hz), 4.79 (2H, s)

$^{13}$C NMR (100 MHz, CDCl$_3$): δ 164.1, 163.0, 136.4, 132.3, 126.1, 125.6, 33.0.

19-5: Preparation of (E)-ethyl-3-(4-hydroxy-3,5-dimethoxyphenyl)acrylate (Compound 19g)

Five drops of concentrated sulfuric acid were slowly added to (E)-3-(4-hydroxy-3,5-dimethoxyphenyl)acrylic acid (Compound 19f) (0.45 g, 2.0 mmol) dissolved in an anhydrous ethanol solvent (10.0 mL) under argon atmosphere at 0° C. The reaction mixture was stirred under reflux at 80° C. for 15 hours. Upon the completion of the reaction, the temperature was lowered to room temperature, and the solvent was all removed by evaporation under reduced pressure. Thereafter, water (20.0 mL) was added to the mixture, followed by extraction three times with ethyl acetate (35.0 mL). The organic layer was washed once with a saturated sodium bicarbonate aqueous solution (25.0 mL), three times with water (30.0 mL), and once with a saturated sodium chloride solution (30.0 mL), dried over anhydrous magnesium sulfate, evaporated under reduced pressure, and then separated by column chromatography (ethyl acetate/hexane=1/10), to give (E)-ethyl-3-(4-hydroxy-3,5-dimethoxyphenyl)acrylate (Compound 19g) (0.47 g, 92.9%).

$R_f$=0.52 (ethyl acetate/hexane=2/3)

19-6: Preparation of (E)-ethyl-3-(4-((5-(3,5-dichlorophenyl)-1,3,4-oxadiazol-2-yl)methoxy)-3,5-dimethoxyphenyl) acrylate (Compound 19h)

Potassium carbonate was added at room temperature to (E)-ethyl-3-(4-hydroxy-3,5-dimethoxyphenyl)acrylate (Compound 19g) (0.23 g, 0.91 mmol) dissolved in an anhydrous dimethyl formamide solvent (3.0 mL) under argon atmosphere for 5 minutes. 2-(Chloromethyl)-5-(3,5-dichlorophenyl)-1,3,4-oxadiazole (Compound 19e) (0.24 g, 0.91 mmol) dissolved in an anhydrous dimethylformamide solvent (3.0 mL) and potassium iodide (0.02 g, 0.09 mmol) were slowly added to the above mixture (compound 19g). The reaction mixture was stirred at 65° C. for 6 hours. Upon the completion of the reaction, the temperature was lowered to room temperature, and solids were filtered using a filtration device, and washed with ethyl acetate (25.0 mL) and water (20.0 mL). Water (20.0 mL) was added to the filtered liquid, followed by extraction twice with an ethyl acetate solvent (50.0 mL). The organic layer was washed three times with water (25.0 mL) and once with a saturated sodium chloride solution (250 mL), dried over anhydrous magnesium sulfate, evaporated under reduced pressure, and then separated by column chromatography (ethyl acetate/hexane=1/4 to 1/3), to give (E)-ethyl-3-(4-((5-(3,5-dichlorophenyl)-1,3,4-oxadiazole-2-yl)methoxy)-3,5-dimethoxyphenyl)acrylate (Compound 19h) (0.40 g, 91.8%) as a white soft hair solid.

R$_f$=0.45 (ethyl acetate/hexane=1/2)

$^1$H NMR (400 MHz, CDCl$_3$): δ 8.00 (2H, d, J=2.0 Hz), 7.58 (1H, d, J=16.0 Hz), 7.55 (1H, t, J=2.0 Hz), 6.73 (2H, s), 6.35 (1H, d, J=16.0 Hz), 5.29 (2H, s), 4.27 (2H, q, J=7.2 Hz), 1.34 (3H, t, J=7.2 Hz)

$^{13}$C NMR (100 MHz, CDCl$_3$): δ 166.9, 163.7, 163.6, 153.6, 144.3, 137.0, 136.3, 132.0, 131.7, 126.4, 125.5, 118.5, 105.0, 63.7, 60.8, 56.3, 14.5.

19-7: Preparation of (E)-3-(4-((5-(3,5-dichlorophenyl)-1,3,4-oxadiazol-2-yl)methoxy)-3,5-dimethoxyphenyl)acrylic Acid (Compound 19i)

Potassium hydroxide (0.12 g, 2.09 mmol) was added at room temperature to (E)-ethyl-3-(4-((5-(3,5-dichlorophenyl)-1,3,4-oxadiazol-2-yl)methoxy)-3,5-dimethoxyphenyl)acrylate (Compound 19h) (0.40 g, 0.83 mmol) dissolved in anhydrous ethanol (7.0 mL) under argon atmosphere, followed by stirring under reflux at 80° C. for 3 hours. Upon the completion of the reaction, the temperature was lowered to room temperature, and the solvent was all removed by evaporation under reduced pressure. Thereafter, ice water (10.0 mL) was added to the mixture, and acidified with 1 N hydrochloric acid, and then solids were filtered using a filtration device. The solid compound was washed several times with water, and sufficiently dried, to give (E)-3-(4-((5-(3,5-dichlorophenyl)-1,3,4-oxadizaol-2-yl)methoxy)-3,5-dimethoxyphenyl)acrylic acid (Compound 19i) (0.29 g, 77.5%) as a yellow solid.

$^1$H NMR (400 MHz, DMSO-d$_6$): δ 10.10 (1H, br s), 7.90 (2H, d, J=2.0 Hz), 7.88 (1H, t, J=2.0 Hz), 7.53 (1H, d, J=16.0 Hz), 7.09 (2H, s), 6.58 (1H, d, J=16.0 Hz), 4.51 (2H, s), 3.86 (6H, s)

$^{13}$C NMR (100 MHz, DMSO-d$_6$): δ 167.9, 167.0, 162.5, 152.4, 143.4, 137.3, 135.6, 134.4, 131.3, 130.6, 126.4, 6.9, 163.7, 163.6, 153.6, 144.3, 137.0, 136.3, 132.0, 131.7, 126.3, 119.6, 105.7, 70.8, 56.2.

19-8: Synthesis of (E)-3-chloro-1-(3-(4-((5-(3,5-dichlorophenyl)-1,3,4-oxadiazol-2-yl)methoxy)-3,5-dimethoxyphenyl)acryloyl)-5,6-dihydropyridin-2(1H)-one (Compound 19)

3-Chloro-5,6-dihydropyridin-2 (1H)-one (Compound 19k) (25 mg, 0.19 mmol) was added into a 25-mL round-bottom flask under argon atmosphere, and charged with tetrahydrofuran (1.0 mL). Then, the temperature was lowered to −78° C., and LDA (0.10 mL, 0.19 mmol, 2.0 M solution) was added dropwise, followed by stirring for 45 minutes. (E)-3-(4-((5-(3,5-dichlorophenyl)-1,3,4-oxadiazol-2-yl)methoxy)-3,5-dimethoxyphenyl)acryl chloride (Compound 19j) (76 mg, 0.16 mmol) dissolved in tetrahydrofuran (1.0 mL) was slowly added at −78° C., followed by stirring for 1 hour. Upon the completion of the reaction, the remaining LDA was decomposed by 1 N hydrochloric acid, followed by extraction twice with ethyl acetate. The ethyl acetate layer was washed once with a saturated sodium chloride solution, dried over anhydrous sodium sulfate, evaporated under reduced pressure, and then separated by column chromatography (ethyl acetate/hexane=1/4 to 1/3), to give (E)-3-chloro-1-(3-(4-((5-(3,5-dichlorophenyl)-1,3,4-oxadiazol-2-yl)methoxy)-3,5 dimethoxyphenyl)acryloyl)-5,6-dihydropyridin-2(1H)-one (Compound 19) (8.90 mg, 9.90%) as a pale brown solid.

$^1$H NMR (400 MHz, Chloroform-d) δ 8.00 (d, J=1.9 Hz, 2H), 7.69 (d, J=15.6 Hz, 1H), 7.55 (t, J=1.9 Hz, 1H), 7.44 (d, J=15.5 Hz, 1H), 7.10 (t, J=4.6 Hz, 1H), 6.68 (s, 2H), 5.28 (s, 2H), 4.10 (t, J=6.5 Hz, 2H), 3.81 (s, 6H), 2.58 (td, J=6.4, 4.5 Hz, 2H).

Test Example 1: Inhibition of Nitrogen Monoxide (NO) Production

The nitrogen monoxide (NO) production inhibitory ability of the piperlongumine-based compounds of the present disclosure was evaluated.

In the present test example, the NO production inhibitory ability was evaluated using a Griess reagent (Sigma-Aldrich), which measures the amount of nitrite as a metabolite of nitrogen monoxide (NO). Specifically, Raw264.7 cells were dispensed in a 96-well plate, pre-treated with each compound (1 μg/mL) of Compounds 1-19 and treated with a lipopolysaccharide (LPS, 1 μg/mL) 2 hours later, and then cultured for 24 hours. The culture after completing the reaction was mixed with an equal amount of a Griess reagent, followed by reaction for 10 minutes, and within 30 minutes thereafter, the absorbance was measured at 540 nm by a spectrometer. To obtain a standard curve, sodium nitrate (Promega) was used in serial dilutions from a concentration of 100 μM.

As shown in FIG. 1, among the piperlongumine-based compounds according to the present disclosure, Compounds 1, 3-6, and 8-19 showed significant (p<0.01–0.001) nitrogen monoxide production inhibitory activity, and especially, Compounds 3, 9-15, and 18-19 showed remarkably excellent NO production inhibitory activity.

Test Example 2: Antioxidative Effect—Hydroxyl Radical Scavenging

To investigate the antioxidative effects of the piperlongumine-based compounds of the present disclosure, the hydroxyl radical scavenging ability was evaluated therefor as below.

Figure 2:
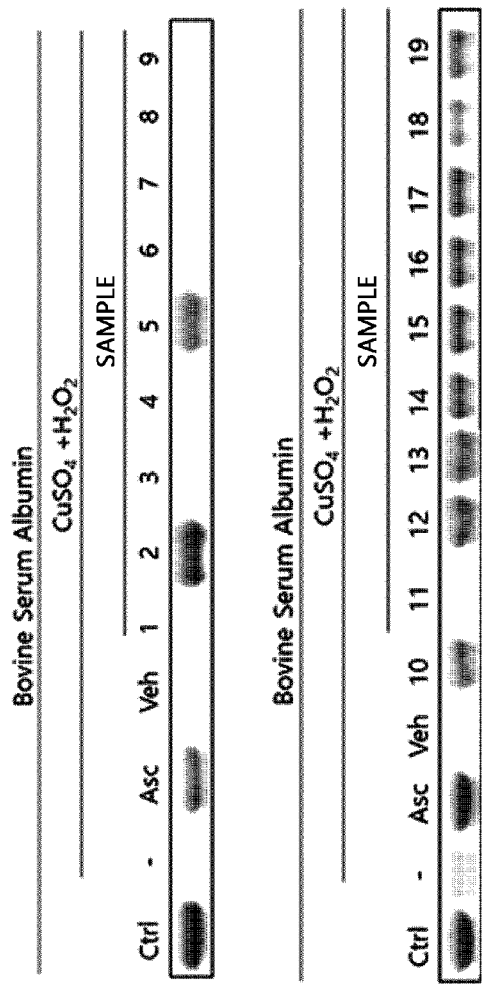
FIG. 2 shows graphs of the results of hydroxy radical inhibition through the use of piperlongumine-based compounds according to the present disclosure.

In the present test example, a bovine serum albumin (BSA, Sigma-Aldrich) degradation method was used to investigate the effects of antioxidants protecting proteins or enzymes from the damage by reactive oxygen species (ROS) through metal ion catalytic reactions. Specifically, the concentration of the target protein BSA was 8 μg/mL, and Cu$^{2+}$ (100 μM) and H$_2$O$_2$ (2.5 mM) were added to generate hydroxide radicals in the primary reaction, which were then mixed with BSA and each compound (1 μg/mL) of Compounds 1-19, followed by secondary reaction. Each group after completing the reaction was electrophoresed on 10% sodium dodecyl sulfate (SDS)-polyacrylamide gel to investigate the BSA protein degradation inhibitory level by each compound, and the results are shown in FIG. 2. Ascorbic acid (150 μM) having excellent antioxidative effect was used as a positive control.

As a result of observing the protein degradation level by the reactive oxygen species (hydroxyl radicals) generated after the primary reaction, the protein was completely destructed in a group with reactive oxygen species alone, a solvent treatment group, and groups treated with piperlongumine-based compounds 1, 3-4, 6-9, and 11, indicating no protein protective ability against reactive oxygen species. However, piperlongumine-based compounds 2, 5, 10, and 12-19 according to the present disclosure were observed to show hydroxyl radical scavenging ability equivalent to or higher than that of the antioxidant ascorbic acid, and the resultant protein protective ability (see FIG. 2).

Test Example 3: Evaluation of Inflammatory Cytokine Inhibitory Effect

The inhibition of inflammatory cytokine expression was investigated by the following method.

3-1: Investigation of Inhibition of Inflammatory Cytokine Expression

Excessive signals by cytokines are known to cause various diseases. Therefore, the inhibition of inflammatory cytokine expression by the compounds of the present disclosure was investigated as follows.

First, the mouse macrophage cell line Raw264.7 for use in the test was cultured in a $CO_2$ incubator adjusted to 37° C. and 5% $CO_2$ using Dulbecco's Modified Eagle Medium (DMEM) or RPMI1640 media containing 10% fetal bovine serum. The cells were used for the test to be described later when the cells reached 90% of confluence, and the cells were adjusted not to exceed 20 passages. The cells cultured as described above were suspended in 0.25% trypsin-EDTA, and counted by a hemocytometer. As for gene expression testing, the cells were dispensed at $1.5 \times 10^6$ cells/well in 6-well plates, previously cultured for 2 hours, and then treated with Compounds 1-19 along with LPS, followed by culture for 20 hours. After the reaction, total RNA was extracted from the cultured Raw264.7 cells by using Trizol reagent (Invitrogen). Specifically, the cells were lysed by addition of 1 mL of Trizol reagent and left at room temperature for 5 minutes, and then 200 µL of chloroform was added, followed by centrifugation at 13,500 rpm for 15 minutes. After 500 µL of the transparent supernatant was taken and transferred to a new tube, an equal amount of isopropyl alcohol was added, followed by centrifugation at 13,500 rpm for 10 minutes, thereby precipitating RNA. The RNA precipitate was washed with 0.75 mL of 70% ethanol diluted with distilled water treated with diethyl pyrocarbonate (DEPC, Sigma-Aldrich), dried in air, and then used as a sample for reverse transcription. The first-strand cDNA synthesis was performed using 1 µg of total RNA, and reverse transcription was performed using the Improm-II reverse transcription system (Promega) and oligo-dT primer. The qPCR assay was performed using the Rotor-Gene 6000 (Qiagen, CA, USA). The expression of genes was quantitatively measured using the primers in Table 1, and the relative levels normalized to β-actin were compared and analyzed.

TABLE 1

| Gene | Primer | Nucleotide sequence | SEQ ID NO |
|---|---|---|---|
| β-actin | forward | 5'-TACAGCTTCACCACCACAGC | SEQ ID NO: 1 |
| | reverse | 5'-AAGGAAGGCTGGAAAAGAGC | SEQ ID NO: 2 |
| IL-1 β | forward | 5'-AGCTGTGGCAGCTACCTGTG | SEQ ID NO: 3 |
| | reverse | 5'-GCTCTGCTTGTGAGGTGCTG | SEQ ID NO: 4 |
| IL-2 | forward | 5'-CACTTCAAGCTCCACTTCAA | SEQ ID NO: 5 |
| | reverse | 5'-AGTCAAATCCAGAACATGCC | SEQ ID NO: 6 |
| IL-4 | forward | 5'-CCTCCAAGAACACAACTGAG | SEQ ID NO: 7 |
| | reverse | 5'-TCCTTCACAGGACAGGAATT | SEQ ID NO: 8 |
| IL-6 | forward | 5'-TTCCATCCAGTTGCCTTCTT | SEQ ID NO: 9 |
| | reverse | 5'-GTTGGGAGTGGTATCCTCTG | SEQ ID NO: 10 |
| IL-10 | forward | 5'-ACAATAACTGCACCCACTTC | SEQ ID NO: 11 |
| | reverse | 5'-CCACTGCCTTGCTCTTATTT | SEQ ID NO: 12 |
| IL-17a | forward | 5'-CTCCAGAATGTGAAGGTCAA | SEQ ID NO: 13 |
| | reverse | 5'-AACAGAATTCATGTGGTGGT | SEQ ID NO: 14 |
| IFNγ | forward | 5'-TGAAAATCCTGCAGAGCCAG | SEQ ID NO: 15 |
| | reverse | 5'-TGGACCTGTGGGTTGTTGAC | SEQ ID NO: 16 |
| TNFα | forward | 5'-GATTATGGCTCAGGGTCCAA | SEQ ID NO: 17 |
| | reverse | 5'-GAGACAGAGGCAACCTGACC | SEQ ID NO: 18 |

Figure 3:
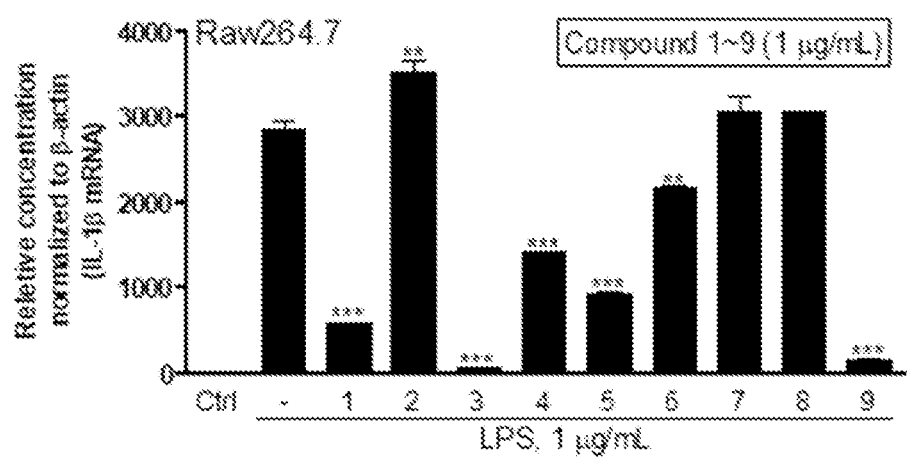
FIGS. 3 to 5 show graphs depicting the results of inhibition of inflammatory cytokine gene expression through the use of piperlongumine-based compounds according to the present disclosure.
Figure 3:
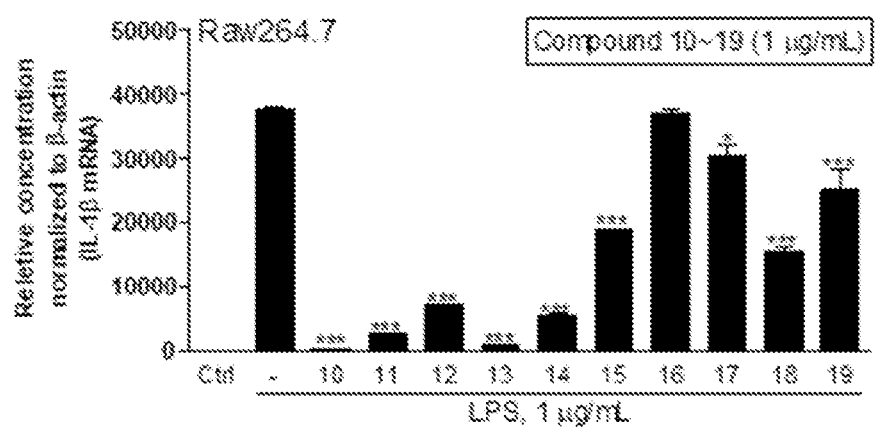
Figure 4:
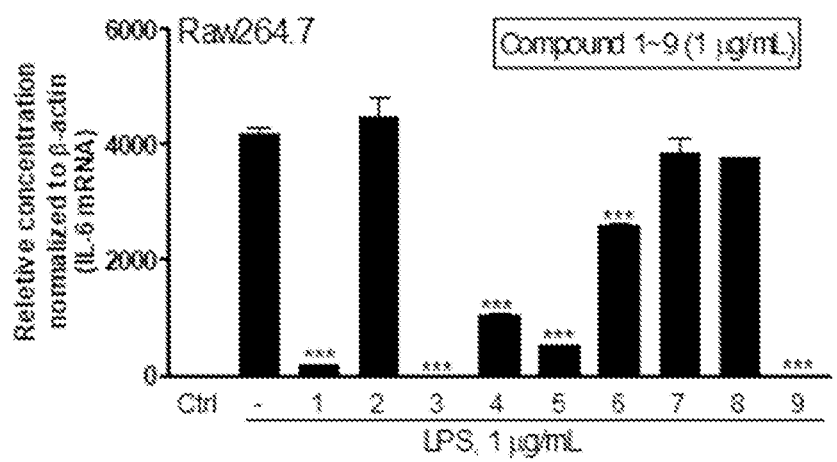
Figure 4:
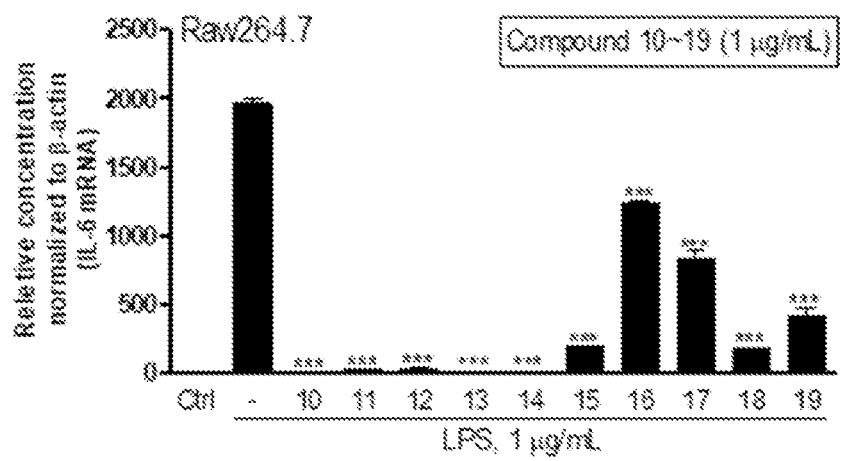
Figure 5:
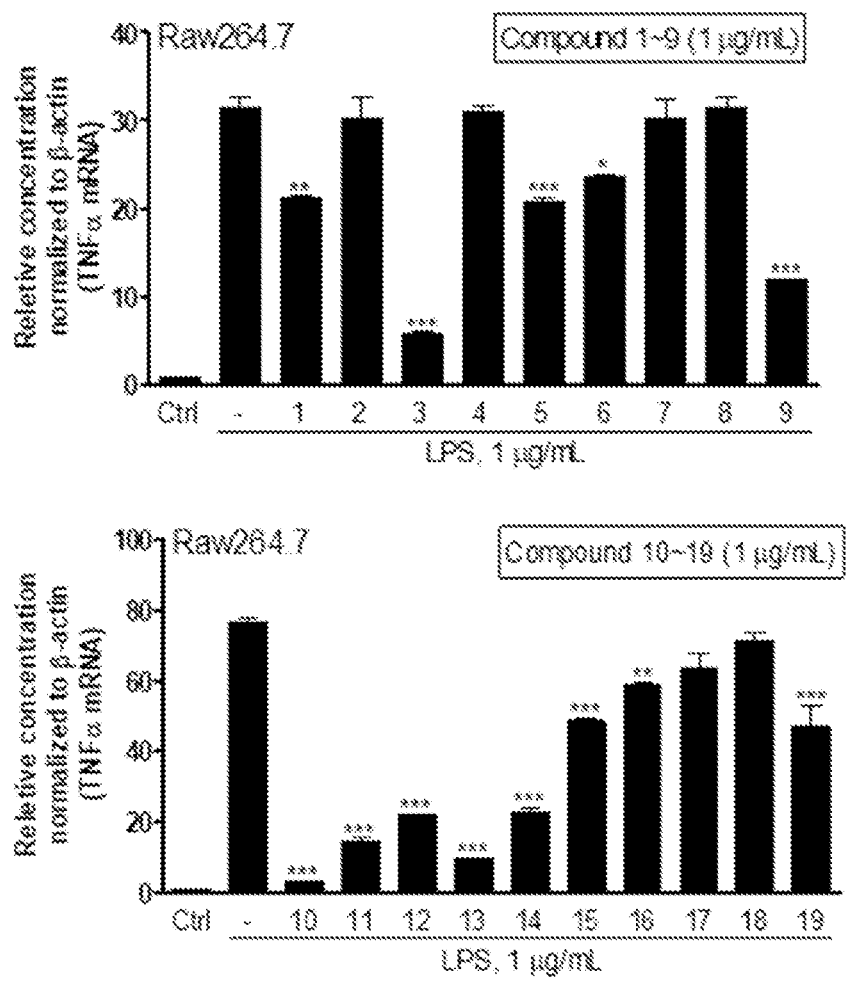

As shown in FIGS. 3 to 5, among the piperlongumine-based compounds according to the present disclosure, Compounds 1, 3-6, 9-15, and 17-19 showed the cytokine IL-1β gene expression inhibitory activity and Compounds 1, 3-6, and 9-19 showed the IL-6 gene expression inhibitory activity. In addition, Compounds 1, 3, 5-6, 9-16, and 19 inhibited the TNF-α gene expression, indicating effective anti-inflammatory activity.

3-2: Investigation of T Cell-Dependent Cytokine Gene Expression Inhibition

In the present test example, Balb/c mouse splenocytes were isolated, and the immune cell activity inhibitory ability of Compounds 1-19, which are piperlongumine-based compounds, was investigated in ex-vivo conditions, through analysis of expression of T cell-dependent cytokines, for example, Th1 cytokines (IL-2 and IFNγ), Th2 cytokines (IL-4 and IL-10), and Th17 cytokine (IL-17a) genes. To induce T cell-dependent stimulation, Balb/c mouse splenocytes were treated with CD3 monoclonal antibody to stimulate the T cell receptor complexes and activate T cells, and under the same conditions, the T cell activity inhibitory ability of Compounds 1-19 as the piperlongumine-based compounds was analyzed by the same method as in Example 3-1. The results are shown in FIGS. 6 to 10, respectively.

Figure 6:
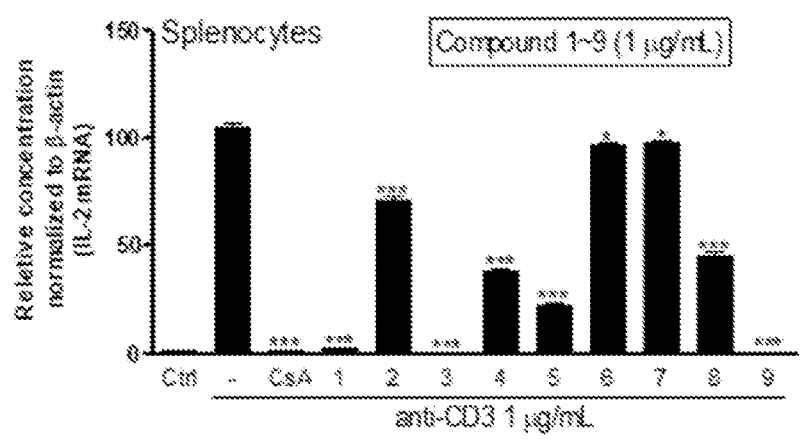
FIGS. 6 to 10 show graphs depicting the results of inhibition of T cell-dependent cytokine gene expression through the use of piperlongumine-based compounds according to the present disclosure.
Figure 6:
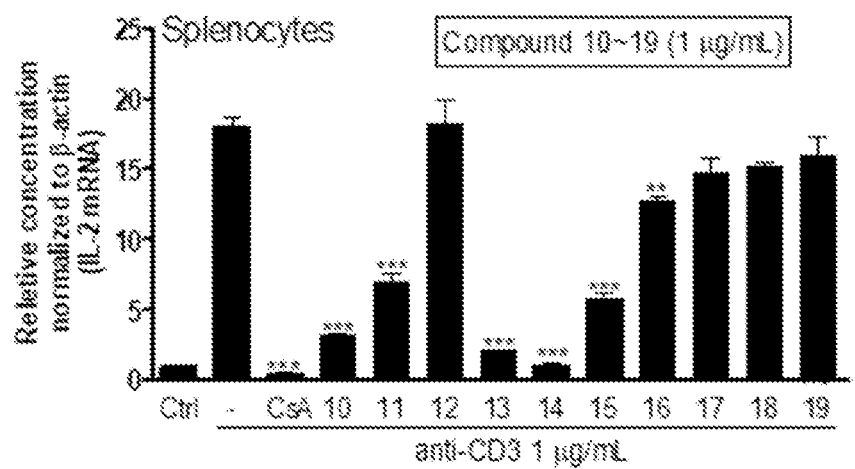
Figure 7:
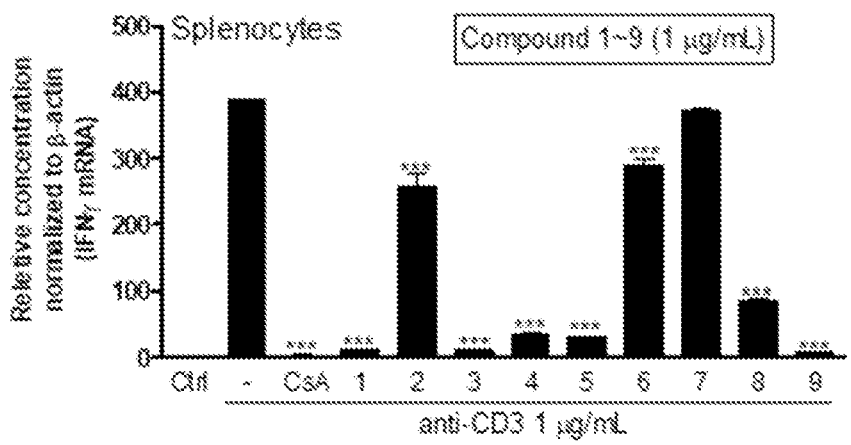
Figure 7:
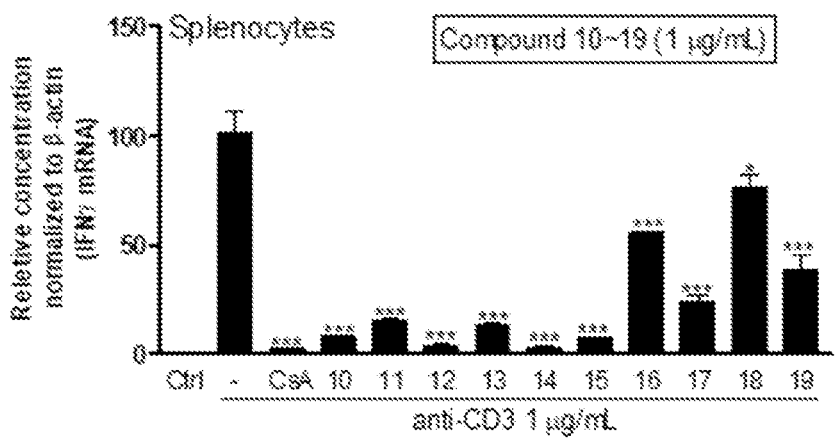

FIGS. 6 and 7 show graphs of the inhibition of expression of Th1 cytokine-derived IL-2 and IFNγ genes among T-cell dependent cytokines. As shown in FIG. 6, among the piperlongumine-based compounds of the present disclosure, Compounds 1-11 and 13-16 showed IL-2 gene expression inhibitory activity, and especially, Compounds 1, 3, and 9 were observed to show IL-2 gene expression inhibitory activity at a significant level equal to or greater than that of cyclosporine (CsA, immunosuppressant) as a control substance.

As shown in FIG. 7, among the piperlongumine-based compounds of the present disclosure, Compounds 1-6 and 8-19 showed inhibitory ability on Th1-derived IFNγ expression, and especially, Compounds 1, 3-5, 9, 12, and 14 showed very high inhibitory ability.

Figure 8:
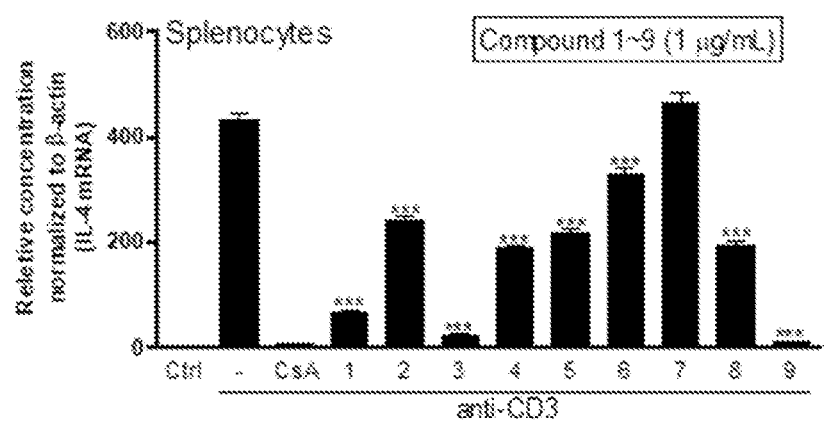
Figure 8:
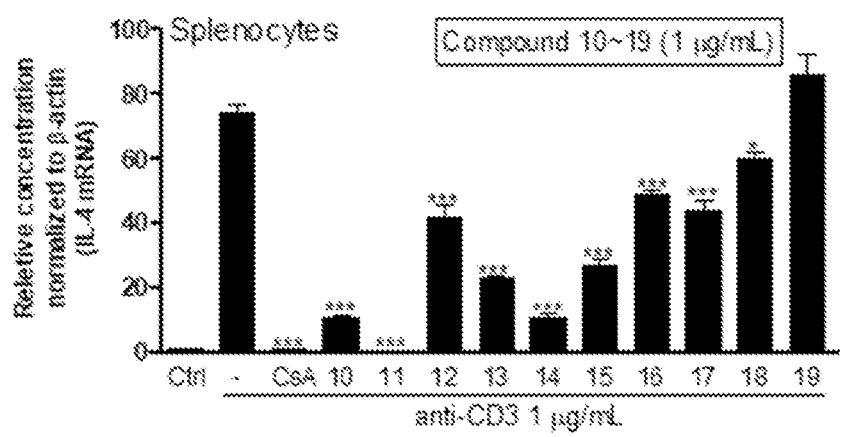
Figure 9:
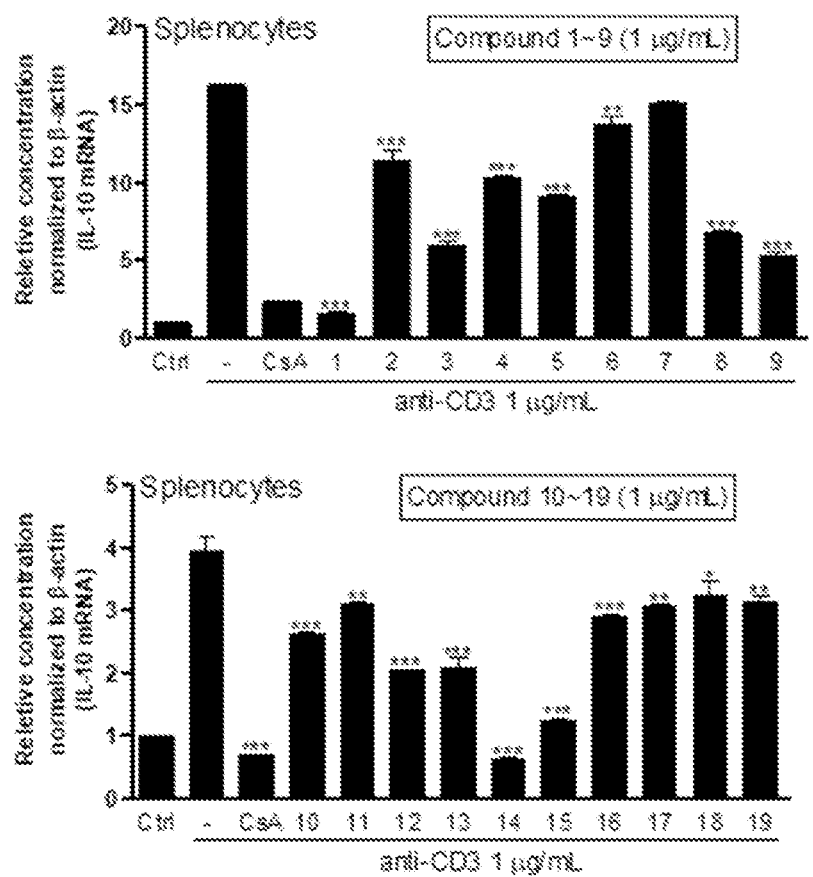

FIGS. 8 and 9 show graphs of the inhibition of expression of Th2 cytokine-derived IL-4 and IL-10 genes among T cell-dependent cytokines. As shown in FIG. 8, among the piperlongumine-based compounds of the present disclosure, Compounds 1-6 and 8-18 were proved to show IL-4 gene expression inhibitory activity, and especially, Compounds 1, 3, 9, and 11 showed IL-4 gene expression inhibitory activity at a significant level equal to or greater than that of cyclosporine (CsA, immunosuppressant) as a control substance.

As shown in FIG. 9, Compounds 1-6 and 8-19, which are piperlongumine-based compounds of the present disclosure, significantly inhibited the expression of IL-10.

Figure 10:
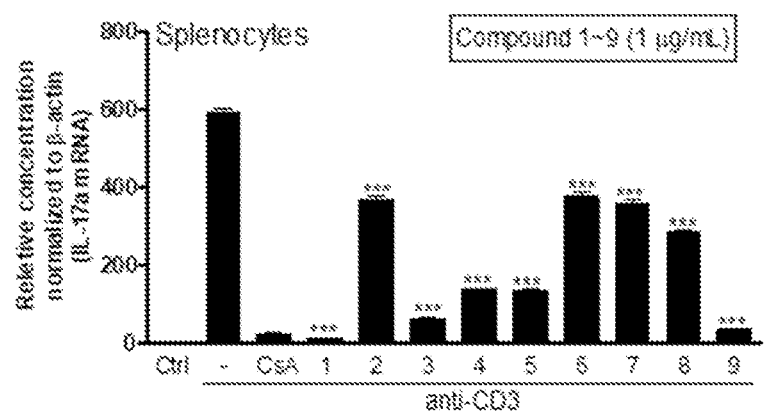
Figure 10:
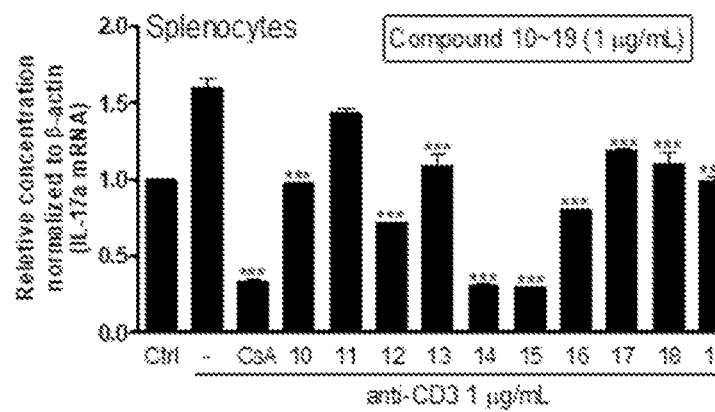

FIG. 10 shows graphs of the inhibition of expression of Th17 cytokine-derived IL-17a gene among T cell-dependent cytokines. As shown in FIG. 10, among the piperlongumine-based compounds of the present disclosure, Compounds 1-10 and 12-19 showed IL-17a gene expression inhibitory activity, and especially, Compounds 1, 3-5, 9, and 14-15 were observed to show higher activity. Especially, Compounds 1, which is the piperlongumine-based compound of the present disclosure, not only showed excellent IL-17a expression inhibitory activity compared with cyclosporine (CSA, immunosuppressant) as the control, and unlike in IL-2 and IL-4, showed at least 6-fold and at least 3-fold higher gene expression inhibitory activity compared with Compounds 3 and 9, respectively.

From the above-described results, the piperlongumine-based compounds of the present disclosure, especially, Compounds 1, 3, and 9, are determined to be novel compounds that effectively inhibit IL-2, IL-4, and IFNγ. In particular, all the piperlongumine-based compounds of the present disclosure, except for Compound 7, had the activity to control IL-10 overexpressed by Th2 (helper T-2 cells), and could also be sufficiently identified to have a potential as an immuno regulator through the effective inhibition of IL-17a, which helps the axis of cytokine IL-23.

Test Example 4: Evaluation of Immune Cell Signaling Inhibitory Activity

To investigate intracellular signaling of immune regulation-related genes and activity inhibitory ability, analysis was conducted using a reporter gene expression analysis system as follows.

In the present test example, THP1-Lucia NF-κB, HEK-Lucia RIG-1, HEK-Blue-IL-4/IL-13, and HEK-Blue IL-10 cell lines were purchased from InVivoGen, and evaluated for inhibitory activity on immune cell signaling, and the analysis was performed according to the manufacturer's analysis method. Specifically, the four types of cell lines were treated with each of test substances, which are the piperlongumine-based compounds 1 to 19, and then treated with each of promoter stimulants (LPS, 3p-hpRNA, interleukin-4, and interleukin-10). The response was induced according to the guidelines, and then the activity inhibitory ability was analyzed. The results are shown in FIGS. 11 to 14.

Figure 11:
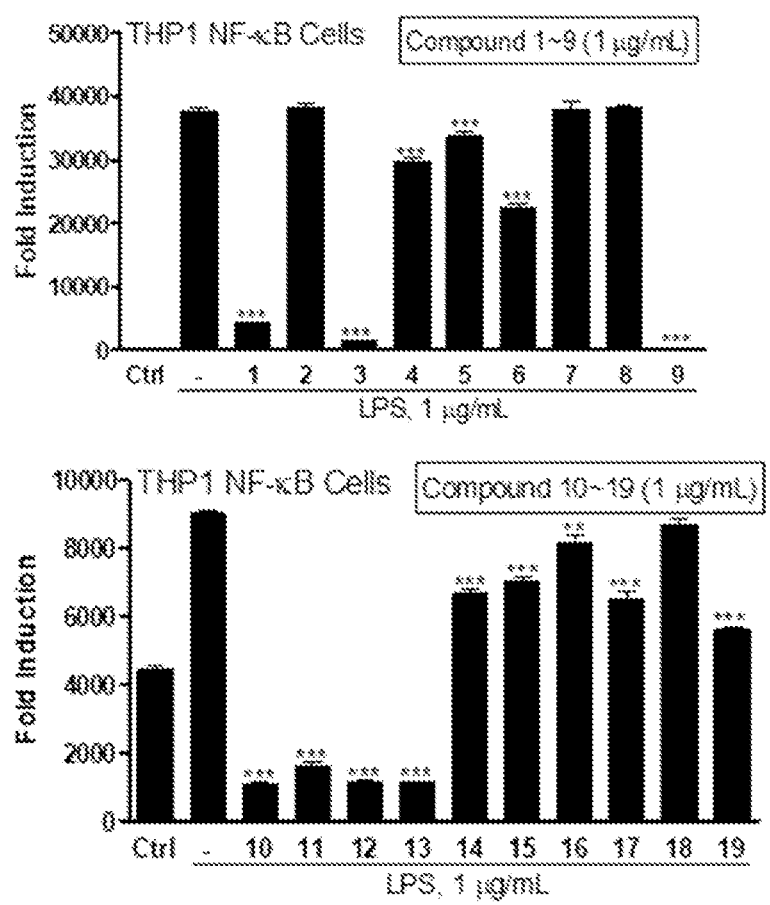
FIGS. 11 to 14 show graphs depicting the results of inhibition of reporter gene expression through the use of piperlongumine-based compounds according to the present disclosure.

FIG. 11 shows graphs analyzing the NF-κB signaling pathway modulation of each of the piperlongumine-based compounds modulated after the cells stimulated with a lipopolysaccharide (LPS) were treated with the compounds. As shown in FIG. 11, among the piperlongumine-based compounds of the present disclosure, Compounds 1, 3-6, 9-17, and 19 were observed to show the NF-κB activity inhibitory effect, and especially, Compounds 1, 3, and 9 were identified to show very high NF-κB activity inhibitory ability.

Figure 12:
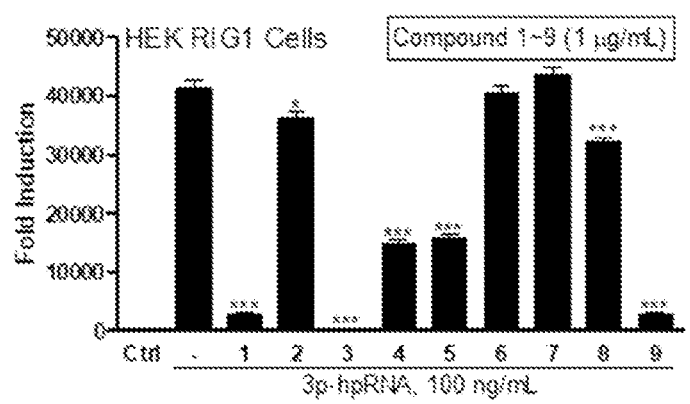
Figure 12:
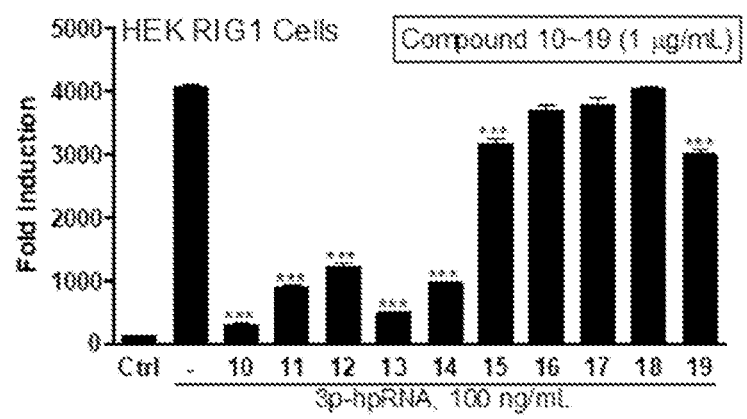

FIG. 12 shows graphs analyzing the RIG1 activity inhibition of the piperlongumine-based compounds through the HEK RIG1 system.

As shown in FIG. 12, among the piperlongumine-based compounds of the present disclosure, Compounds 1-5, 8-15, and 19 showed the RIG1 activity inhibitory effect, and especially, Compounds 1, 3, 9, and 10 were identified to have very high RIG1 activity inhibitory ability.

Figure 13:
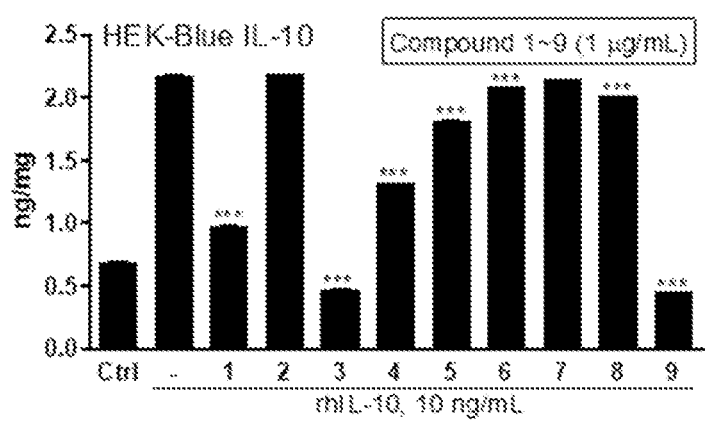
Figure 13:
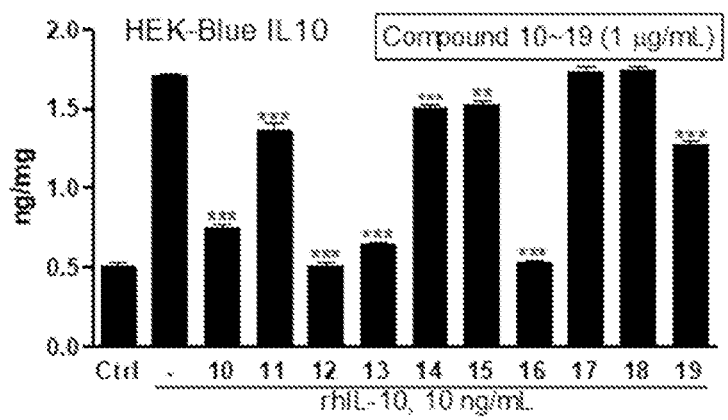

FIG. 13 shows graphs analyzing the STAT3 signaling modulation of the piperlongumine-based compounds through the HEK Blue IL-10 system.

STAT3 is an important transcription factor that transmits signals from the cytoplasm to the nucleus after cytokine stimulation. As shown in FIG. 13, among the piperlongumine-based compounds of the present disclosure, Compound 1, 3-6, 8-16, and 19 showed the STAT3 activity inhibitory effect, and especially, Compounds 1, 3, 9-10, 12-13, and 16 were identified to have very high STAT3 activity inhibitory ability.

Figure 14:
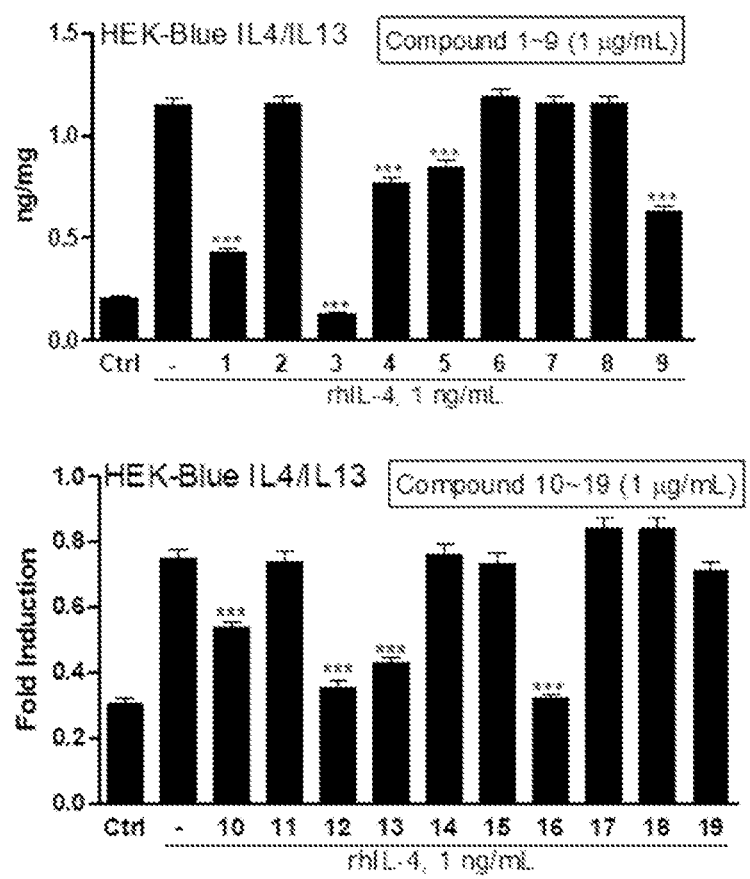

FIG. 14 shows graphs analyzing the STAT6 signaling modulation of the piperlongumine-based compounds through the HEK Blue IL4/IL-13 system. STAT6 is a transcription factor that plays a role in modulating the expression of various cytokines, hormones, and growth factors by signals coming from the outside. IL-4/IL-13 and STAT6 are also important modulator of Th2. As shown in FIG. 14, among the piperlongumine-based compounds of the present disclosure, Compounds 1, 3-5, 9-10, 12-13, and 16 showed the STAT6 activity inhibitory effect, and especially, Compounds 1, 3, 12-13, and 16 were identified to have very high STAT6 activity inhibitory ability.

It could be identified from the above-described results that the piperlongumine-based compounds of the present disclosure had excellent inhibitory activity on immune cell signaling of NF-κB, RIG1, STAT3, STAT6, or the like, and thus the piperlongumine-based compounds of the present disclosure can be helpfully applied as an immuno regulator.

What is claimed is:

1. A compound represented by any one of chemical formulas 2 to 5 below, or a pharmaceutically acceptable salt or solvate thereof:

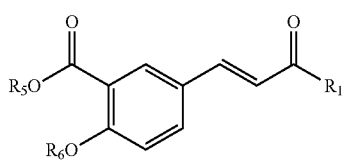

[Chemical Formula 2]

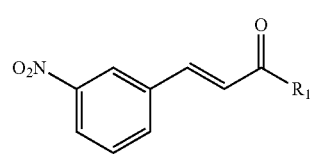

[Chemical Formula 3]

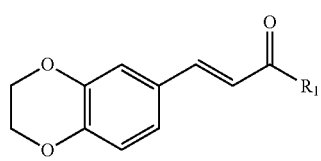

[Chemical Formula 4]

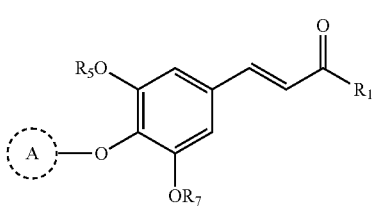

[Chemical Formula 5]

wherein, in chemical formulas 2 to 5, $R_5$ to $R_7$ are the same or different from each other and are each independently selected from the group consisting of hydrogen, deuterium, halogen, a nitro group, a hydroxyl group, an amino group, a $C_1$-$C_{40}$ alkyl group, a $C_2$-$C_{40}$ alkenyl group, a $C_2$-$C_{40}$ alkynyl group, a $C_3$-$C_{40}$ cycloalkyl group, a heterocycloalkyl group having 3 to 40 ring atoms, a $C_1$-$C_{20}$ alkoxy group, a $C_1$-$C_{20}$ ketone group, a $C_1$-$C_{20}$ ester group, a $C_6$-$C_{20}$ aryl group, a heteroaryl group having 5 to 20 ring atoms, and a $C_6$-$C_{20}$ aryloxy group, and ring A is selected from the group consisting of a cycloalkyl ring, a heterocycloalkyl ring, an aryl ring, and a heteroaryl ring each having 20 or less carbon atoms, wherein ring A may be substituted with at least one substituent selected from the group consisting of deuterium, halogen, a cyano group, a nitro group, a $C_1$-$C_{40}$ alkyl group, a $C_6$-$C_{40}$ aryl group, and a heteroaryl group having 5 to 40 ring atoms, $R_1$ is a substituent selected from the following structures:

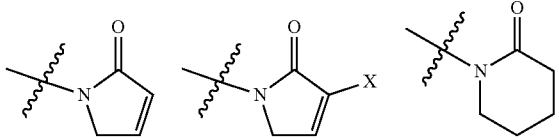

-continued

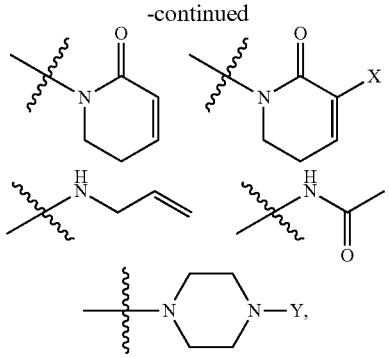

wherein,

X is a halogen atom selected from the group consisting of F, Cl, Br, and I, and

Y is a $C_1$-$C_{10}$ alkyl group, wherein the alkyl group, ketone group, ester group, aryl group, and heteroaryl group of $R_5$ to $R_7$ may be each independently substituted with at least one substituent selected from the group consisting of deuterium, halogen, a cyano group, a nitro group, a $C_1$-$C_{40}$ alkyl group, a $C_2$-$C_{40}$ alkenyl group, a $C_2$-$C_{40}$ alkynyl group, a $C_6$-$C_{40}$ aryl group, a heteroaryl group having 5 to 40 ring atoms, a $C_6$-$C_{40}$ aryloxy group, a $C_1$-$C_{40}$ alkyloxy group, a $C_6$-$C_{40}$ aryl amine group, a $C_3$-$C_{40}$ cycloalkyl group, a heterocycloalkyl group having 3 to 40 ring atoms, a $C_1$-$C_{40}$ alkyl silyl group, a $C_1$-$C_{40}$ alkylboron group, a $C_6$-$C_{40}$ arylboron group, a $C_6$-$C_{40}$ aryl phosphine group, a $C_6$-$C_{40}$ aryl phosphine oxide group, and a $C_6$-$C_{40}$ aryl silyl group, and when the number of substituents is plural, the substituents may be the same or different from each other, with the proviso that:

(i) the compound of Chemical Formula 3, in which $R_1$ is

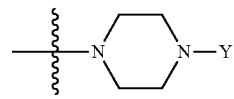

or

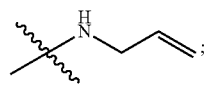 [SMILES: *NCC=C]

and (ii) the compound of Chemical Formula 4 in which $R_1$ is

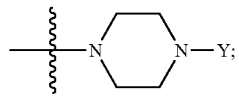

are excluded.

2. The compound of claim 1, or a pharmaceutically acceptable salt or solvate thereof, wherein $R_1$ has a substituent selected from the following structures:

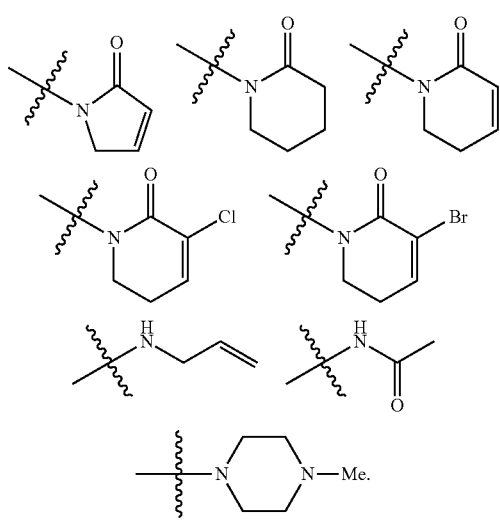

3. The compound of claim 1, or a pharmaceutically acceptable salt or solvate thereof,
wherein
R$_5$ to R$_7$ are the same or different from each other and are each independently selected from the group consisting of hydrogen, a hydroxyl group, a C$_1$-C$_6$ alkyl group, a C$_1$-C$_6$ alkoxy group, a C$_1$-C$_6$ ketone group, and a C$_1$-C$_6$ ester group.

4. The compound of claim 1, or a pharmaceutically acceptable salt or solvate thereof, wherein the compound represented by chemical formulas 2-5 is selected from the group of compounds represented by the following formulas:

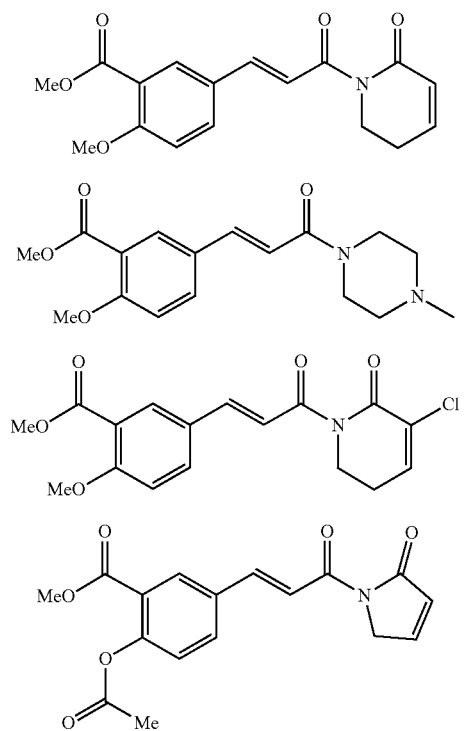

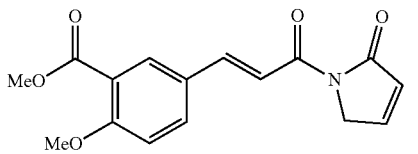

5

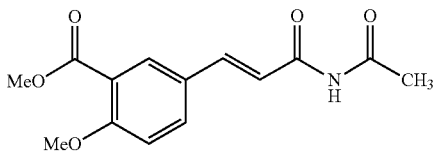

6

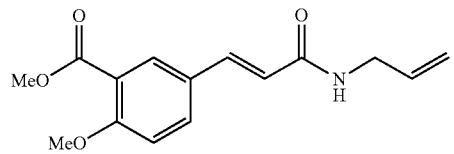

7

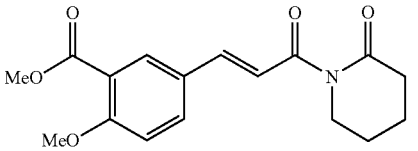

8

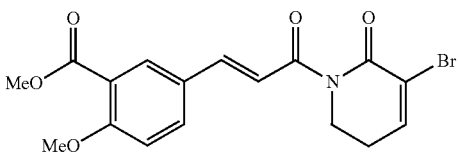

9

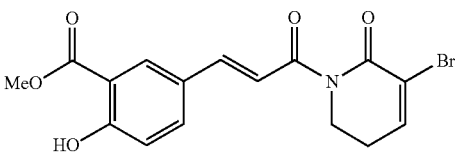

10

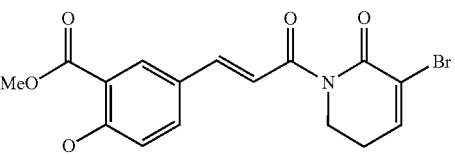

11

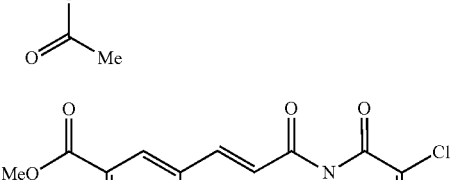

12

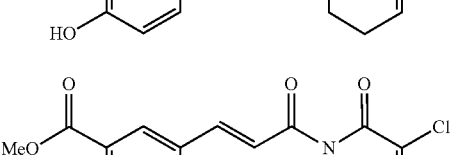

13

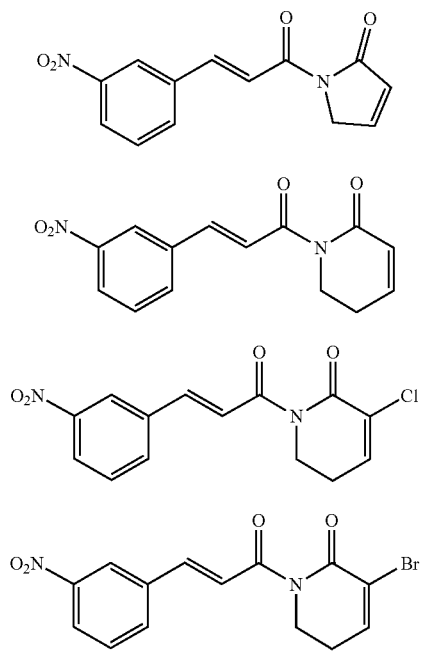
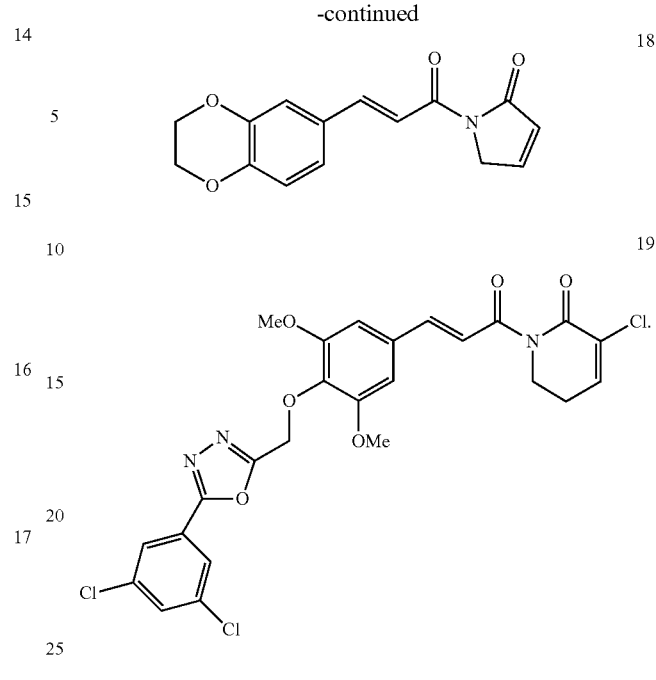
\* \* \* \* \*